US012595247B2

(12) United States Patent
Vakalopoulos et al.

(10) Patent No.: US 12,595,247 B2
(45) Date of Patent: *Apr. 7, 2026

(54) SUBSTITUTED PYRAZOLO PIPERIDINE CARBOXYLIC ACIDS

(71) Applicant: Bayer Aktiengesellschaft, Leverkusen (DE)

(72) Inventors: Alexandros Vakalopoulos, Hilden (DE); Marie-Pierre Collin-Kröpelin, Weil am Rhein (DE); Nuria Ortega Hernandez, Wuppertal (DE); Andre Dieskau, Wuppertal (DE); Melissa Boultadakis-Arapinis, Düsseldorf (DE); Lisa Candish, Wuppertal (DE); Timo Stellfeld, Berlin (DE); Ilka Mathar, Düsseldorf (DE); Lucas Hudson Hofmeister, Berlin (DE); Peter Sandner, Wuppertal (DE); Frank Wunder, Wuppertal (DE); Lisa Dietz, Wuppertal (DE); Robert Alan Webster, Berlin (DE); Carsten Schmeck, Mülheim (DE); Thomas Mondritzki, Essen (DE)

(73) Assignee: Bayer Aktiengesellschaft, Leverkusen (DE)

( * ) Notice: Subject to any disclaimer, the term of this patent is extended or adjusted under 35 U.S.C. 154(b) by 1006 days.

This patent is subject to a terminal disclaimer.

(21) Appl. No.: 17/667,410

(22) Filed: Feb. 8, 2022

(65) Prior Publication Data

US 2022/0274958 A1 Sep. 1, 2022

Related U.S. Application Data

(63) Continuation of application No. PCT/EP2021/084980, filed on Dec. 9, 2021.

(30) Foreign Application Priority Data

Dec. 10, 2020 (EP) .................................... 20213016

(51) Int. Cl.
*C07D 401/14* (2006.01)
*C07D 401/04* (2006.01)

(52) U.S. Cl.
CPC ......... *C07D 401/14* (2013.01); *C07D 401/04* (2013.01)

(58) Field of Classification Search
CPC ............................ C07D 401/14; C07D 401/04
See application file for complete search history.

(56) References Cited

U.S. PATENT DOCUMENTS

| | | | | |
|---|---|---|---|---|
| 8,796,335 | B2 | 8/2014 | Hahn et al. | |
| 8,895,583 | B2 * | 11/2014 | Tan | A61K 31/4545 546/194 |
| 12,195,448 | B2 * | 1/2025 | Vakalopoulos | A61P 9/10 |
| 2004/0121994 | A1 | 6/2004 | Anderson et al. | |
| 2004/0192680 | A1 | 9/2004 | Anderson et al. | |
| 2014/0088080 | A1 | 3/2014 | Koga et al. | |
| 2015/0095515 | A1 | 4/2015 | Krithivas et al. | |
| 2022/0274958 | A1 * | 9/2022 | Vakalopoulos | A61P 9/10 |

FOREIGN PATENT DOCUMENTS

| | | | |
|---|---|---|---|
| DE | 19830430 | | 1/2000 |
| WO | 0002850 | A2 | 1/2000 |
| WO | 0002851 | A1 | 1/2000 |
| WO | 0006568 | A1 | 2/2000 |
| WO | 0006569 | A1 | 2/2000 |
| WO | 0009496 | A1 | 2/2000 |
| WO | 0027394 | A1 | 5/2000 |
| WO | 0031047 | A1 | 6/2000 |
| WO | 0046241 | A2 | 8/2000 |
| WO | 0119355 | A2 | 3/2001 |
| WO | 0119776 | A2 | 3/2001 |
| WO | 0119778 | A1 | 3/2001 |
| WO | 0119780 | A2 | 3/2001 |
| WO | 0120023 | A2 | 3/2001 |
| WO | 0132604 | A1 | 5/2001 |

(Continued)

OTHER PUBLICATIONS

Extended European Search Report of EP Patent Application No. 20213016.7 (filed by Bayer Aktiengesellschaft, entitled "Substituted Pyrazolo Piperidine Carboxylic Acids"), mailed on Apr. 16, 2021 by the European Patent Office.

Evgenov, O.V. et al., "NO-independent stimulators and activators of soluble guanylate cyclase: discovery and therapeutic potential," Nature Reviews, Drug Discovery, 2006, vol. 5, pp. 755-768.

Parés, S. et al., "European Federation of Medicinal Chemistry—XXV International Symposium on Medicinal Chemistry," Drugs of the Future 2018, 43(10), pp. 784.

Stasch, J-P et al., "NO- and haem-independent activation of soluble guanylyl cyclase: molecular basis and cardiovascular implications of a new pharmacological principle," British Journal of Pharmacology 2002, 136, pp. 773-783.

(Continued)

*Primary Examiner* — Sarah Pihonak
*Assistant Examiner* — Mikhail O'Donnel Robinson

(57) ABSTRACT

The invention relates to substituted pyrazolo piperidine carboxylic acids, their salts and to processes for their preparation, and also to their use for preparing medicaments for the treatment and/or prophylaxis of diseases, in particular cardiovascular and cardiac diseases, preferably heart failure with reduced and preserved ejection fraction (HFrEF, HFmrEF and HFpEF), hypertension (HTN), peripheral arterial diseases (PAD, PAOD), cardio-renal and kidney diseases, preferably chronic and diabetic kidney disease (CKD and DKD), cardiopulmonary and lung diseases, preferable pulmonary hypertension (PH), and other diseases, preferably neurodegenerative diseases and different forms of dementias, fibrotic diseases, systemic sclerosis (SSc), sickle cell disease (SCD), wound healing disorders such as diabetic foot ulcer (DFU).

6 Claims, 3 Drawing Sheets
(3 of 3 Drawing Sheet(s) Filed in Color)

(56) References Cited

FOREIGN PATENT DOCUMENTS

| | | | |
|---|---|---|---|
| WO | 0242301 | A1 | 5/2002 |
| WO | 02070462 | A1 | 9/2002 |
| WO | 02070510 | A2 | 9/2002 |
| WO | 03009545 | A2 | 1/2003 |
| WO | 03076408 | A2 | 9/2003 |
| WO | 03090870 | A1 | 11/2003 |
| WO | 2005011727 | A1 | 2/2005 |
| WO | 2005042022 | A2 | 5/2005 |
| WO | 2009032249 | A1 | 3/2009 |
| WO | 2009068652 | A1 | 6/2009 |
| WO | 2009071504 | A1 | 6/2009 |
| WO | 2009123316 | A1 | 10/2009 |
| WO | 2010015652 | A2 | 2/2010 |
| WO | 2010015653 | A1 | 2/2010 |
| WO | 2010065275 | A1 | 6/2010 |
| WO | 2010099054 | A2 | 9/2010 |
| WO | 2010105770 | A1 | 9/2010 |
| WO | 2011104322 | A1 | 9/2011 |
| WO | 2011115804 | A1 | 9/2011 |
| WO | 2011119518 | A1 | 9/2011 |
| WO | 2011147809 | A1 | 12/2011 |
| WO | 2011149921 | A1 | 12/2011 |
| WO | 2012003405 | A1 | 1/2012 |
| WO | 2012004258 | A1 | 1/2012 |
| WO | 2012028647 | A1 | 3/2012 |
| WO | 2012058132 | A1 | 5/2012 |
| WO | 2012059549 | A1 | 5/2012 |
| WO | 2012064559 | A1 | 5/2012 |
| WO | 2012122340 | A1 | 9/2012 |
| WO | 2012139888 | A1 | 10/2012 |
| WO | 2013025425 | A1 | 2/2013 |
| WO | 2013101830 | A1 | 7/2013 |
| WO | 2014039434 | A1 | 3/2014 |
| WO | 2014047111 | A1 | 3/2014 |
| WO | 2014047325 | A1 | 3/2014 |
| WO | 2015095515 | A1 | 6/2015 |
| WO | 2016071212 | A1 | 5/2016 |
| WO | 2020245342 | A1 | 12/2020 |
| WO | 2022122913 | A1 | 6/2022 |

OTHER PUBLICATIONS

Stasch, J-P et al., "Targeting the heme-oxidized nitric oxide receptor for selective vasodilatation of diseased blood vessels," The Journal of Clinical Investigation, 2006, 116(9), pp. 2552-2561.

Weiskopf, R.B. et al., "Hemoglobin-Based Oxygen Carriers: Compassionate Use and Compassionate Clinical Trials," Anesthesia & Analgesia, 2010, 110(3), pp. 659-662.

Artursson P, Karlsson J., "Correlation between oral drug absorption in humans and apparent drug permeability coefficients in human intestinal epithelial (Caco-2) cells," Biochem Biophys Res Commun. Mar. 29, 1991;175(3):880-5.

Berry, S. et al., "Nonarteritic anterior ischemic optic neuropathy: cause, effect, and management," Eye and Brain 2017, 9, pp. 23-28.

Blumberg, D. et al., "Emerging risk factors for glaucoma onset and progression," Progress in Brain Research 2015, vol. 221, pp. 81-101.

Bolinger, M.T. et al., "Moving Past Anti-VEGF: Novel Therapies for Treating Diabetic Retinopathy," Int. J. Mol. Sci. 2016, 17, 1498, 23 pages.

Buchwald S.L. et al., "Design and preparation of new palladium precatalysts for C—C and C—N cross-coupling reactions," Chem. Sci., 2013, 4, 916-920.

Buys, E. et al., "New Insights into the Role of Soluble Guanylate Cyclase in Blood Pressure Regulation," Current Opinion in Nephrology Hypertension 2014, 135-142, 23(2).

Buys, E.S. et al., "Discovery and development of next generation sGC stimulators with diverse multidimensional pharmacology and broad therapeutic potential," Nitric Oxide 2018, 78, pp. 72-80.

Charziralli, I.P. et al., "The Role of Glycemic Control and Variability in Diabetic Retinopathy," Diabetes Ther. 2018, 9, pp. 431-434.

Coyle, J.T. et al., "Oxidative stress, glutamate, and neurodegenerative disorders," Science 1993, 262(5134), pp. 589-695.

De Groef, L. et al., "Differential visual system organization and susceptibility to experimental models of optic neuropathies in three commonly used mouse strains," Experimental Eye Research 2016, 145, pp. 235-247.

Douglas, RM et al., "Independent visual threshold measurements in the two eyes of freely moving rats and mice using a virtual-reality optokinetic system, " Visual Neuroscience 2005, 22, pp. 677-684.

Duh, E.J. et al., "Diabetic retinopathy: current understanding, mechanisms, and treatment strategies," JCI Insight 2017, 2(14): e93751.

Ehara, T. et al., "The Discovery of (S)-1-(6-(3-((4-{1-{Cyclopropanecarbonyl)piperidin-4-yl)-2-methylphenyl)amino)-2,3-dihydro-1 H-inden-4-yl)pyridin-2-yl)-5-methyl-1 H-pyrazole-4-carboxylic Acid, a Soluble Guanylate Cyclase Activator Specifically Designed for Topical Ocular Delivery as a Therapy for Glaucoma," J. Med. Chem. 2018, 61, pp. 2252-2570.

ETDRS (Early Treatment Diabetic Retinopathy Study Research Group), "Fundus Photographic Risk Factors for Progression of Diabetic Retinopathy, ETDRS Report No. 12," Opthalmology, May 1991, vol. 19 (Supplement), pp. 823-833.

Gardner, T.W. et al., "The neurovascular unit and the pathophysiologic basis of diabetic retinopathy," Graefes Arch Clin Exp Ophthalmol 2017, 255, pp. 1-6.

Giannakaki-Zimmermann, H. et al., "Optical Coherence Tomography Angiography in Mice: Comparison with Confocal Scanning Laser Microscopy and Fluorescein Angiography," TVST 2016, 5(4), Article 11, 9 pages.

Gross, J.G. et al., "Five-Year Outcomes of Panretinal Photocoagulation vs Intravitreous Ranibizumab for Proliferative Diabetic Retinopathy, A Randomized Clinical Trial," JAMA Opthalmol. 2018, 136(10), pp. 1138-1148.

Gupta, V.B. et al., "Etiopathogenesis of cataract: An appraisal," Indian Journal of Ophthalmology 2014, 62(2), pp. 103-110.

Hassan J. et al., "Aryl-Aryl Bond Formation One Century after the Discovery of the Ullmann Reaction," Chemical Reviews 2002 102 (5), 1359-1470.

Hayreh, S.S., "Controversies on neuroprotection therapy in non-arteritic anterior ischaemic optic neuropathy," Br J Ophthalmol 2020, 104, pp. 153-156.

Hoenicka, M. et al., "Purified soluble guanylyl cyclase expressed in a baculovirus/Sf9 system: stimulation by YC-1, nitric oxide, and carbon monoxide," J Mol Med 1999, 77, pp. 14-23.

Hoeper et al., "Diagnosis, Assessment, and Treatment of Non-Pulmonary Arterial Hypertension Pulmonary Hypertension," Journal of the American College of Cardiology, Jun. 2009, 54(1 Suppl. S), pp. S85-S96.

Huang, W. et al., "Application of electroretinography (ERG) in early drug development for assessing retinal toxicity in rats," Toxicology and Applied Pharmacology 2015, 289, pp. 525-533.

Inoue et al., 2020, vol. 5 No. 19, pp. 10633-10640.

International Search Report and Written Opinion of PCT/EP2021/084986 (filed on Dec. 9, 2021 by Applicant: Bayer Aktiengesellschaft), search completed on Feb. 7, 2022, mailed by the European Patent Office on Mar. 3, 2022, 12 pages.

International Search Report and Written Opinion of PCT/EP2021/084987 (filed on Dec. 9, 2021 by Applicant: Bayer Aktiengesellschaft), search completed on Jan. 25, 2022, mailed by the European Patent Office on Feb. 7, 2022, 16 pages.

International Search Report and Written Opinion of PCT/EP2021/084989 (filed on Dec. 9, 2021 by Applicant: Bayer Aktiengesellschaft), search completed on Feb. 7, 2022, mailed by the European Patent Office on Feb. 23, 2022, 12 pages.

International Search Report of PCT/EP2021/084991 (filed on Dec. 9, 2021 by Bayer Aktiengesellschaft), search completed on Mar. 23, 2022 and mailed on Mar. 31, 2022 by the European Patent Office.

Kolb, H. et al., "Webvision: The Organization of the Retina and Visual System" [Internet] 1995, Salt Lake City (UT): University of Utah Health Sciences Center; PMID: 21413389.

Le Gall, et al., "Autosomal dominant polycystic kidney disease", The Lancet, Mar. 2, 2019, vol. 393, pp. 919-935.

(56) References Cited

OTHER PUBLICATIONS

Li, Q. et al., "Diabetic eNOS-Knockout Mice Develop Accelerated Retinopathy," Investigative Opth– thalmology Visual Science (IVOS), 2010, 51(10), pp. 5240-5246.
Li, Q. et al., "Early Retinal Damage in Experimental Diabetes: Electroretinographical and Morphological Observations," Exp. Eye Res. 2002, 74, pp. 615-625.
Maher, P. et al., "The Molecular Basis of Oxidative Stress-Induced Cell Death in an Immortalized Retinal Ganglion Cell Line," IOVS 2005, 46(2), pp. 749-757.
Mcculloch, D.L., et al., "ISCEV Standard for full-field clinical electroretinography," Doc Opththalmol 2015, 130, pp. 1-12.
Metea, M.R. et al., "Signalling within the neurovascular unit in the mammalian retina," Exp. Physiol. 2007, 92(4), pp. 535-640.
Meyer, C.H. et al., "Nutritional Supplementation to Prevent Cataract Formation," Dev Ophthalmol. Basel, Karger 2005, vol. 38, pp. 103-119.
Newman, N.J. et al., "Hereditary optic neuropathies," Eye 2004, 18, pp. 1144-1160.
Nucci, C. et al., "Neuroprotective agents in the management of glaucoma," Eye 2018, 32, pp. 938-945.
O'Neill, E.C. et al., "The optic nerve head in acquired optic neuropathies," Nat. Rev. Neurol. 2010, 6, pp. 221-236.
Pollreisz, A. et al., "Diabetic Cataract—Pathogenesis, Epidemiology and Treatment," Journal of Ophthalmology 2010, Article ID 608751, 8 pages.
Prasad, S. et al., "Anatomy and physiology of the afferent visual system," Handbook of Clinical Neurology 2011, vol. 102 (3rd series), pp. 3-19.
Prasanna, G. et al., "A Novel Selective Soluble Guanylate Cyclase Activator, MGV354, Lowers Intraocular Pressure in Preclinical Models, Following Topical Ocular Dosing," IOVS 2018, 59(5), pp. 1704-1716.
Prusky, G.T. et al., "Rapid Quantification of Adult Developing Mouse Spatial Vision Using a Virtual Optomotor System," IOVS 2004, 45(12), pp. 4611-4616.
Robinson, W. G. et al., "Diabetic-like Retinopathy Ameliorated with the Aldose Reductase Inhibitor WAY-121, 509," IOVS 1996, 37(6), pp. 1149-1156.
Sandner, P. et al., "Soluble Guanylate Cyclase Stimulators and Activators, " Handbook of Experimental Pharmacology, 2018, eds. H.H.H.W. Schmidt et al., Reactive Oxygen Species, pp. 355-394.
Schaefer, S. et al., "Aberrant Utilization of Nitric Oxide and Regulation of Soluble Guanylate Cyclase in Rat Diabetic Retinopathy," Antioxidants Redox Signaling 2003, 5(4), pp. 457-465.
Schmidt et al., "NO-and Haem-Independent Soluble Guanylate Cyclase Activators," Handbook of Experimental Pharmacology, Springer Verlag (publisher), Berlin and Heidelberg Germany, 2009, vol. 191, pp. 309-339.
Shahsuvaryan, M., "Glaucomatous Optic Neuropathy Management: the Role of Neuroprotective Agents," Mehdi Opththalmol 2013, 2(2), pp. 41-46.
Sivaprasad, S. et al., "Clinical efficacy of intravitreal aflibercept versus panretinal photocoagulation for best corrected visual acuity in patients with proliferative diabetic retinopathy at 52 weeks (Clarity): a multicentre, single-blinded, randomised, controlled, phase 2b, non-inferiority trial," Lancet 2017, 389, pp. 2193-2203.
Solomon, S.D. et al., "Diabetic Retinopathy: A Position Statement by the American Diabetic Association," Diabetes Care 2017, 40, pp. 412-418.
Stacy, R. et al., "A Randomized, Controlled Phase I/II Study to Evaluate Safety and Efficacy of MGV354 for Ocular Hypertension or Glaucoma," Am. J. of Ophthalm. 2018, 192, pp. 113-123.
Stasch JP, Dembowsky K, Perzborn E, Stahl E, Schramm M. "Cardiovascular actions of a novel NO-independent guanylyl cyclase stimulator," BAY 41-8543: in vivo studies. Br J Pharmacol. Jan. 2002; 135(2):344-55.
Tabin, G. et al., "Cataract surgery for the developing world," Current Opinion in Ophthalmology 2008, 19, pp. 55-59.
Van den Buuse M., "Circadian rhythms of blood pressure, heart rate, and locomotor activity in spontaneously hypertensive rats as measured with radio-telemetry," Physiol Behav. Apr. 1994;55(4):783-7.
Van Hove, I. et al., "MMP-3 Deficiency Alleviates Endotoxin-Induced Acute Inflammation in the Posterior Eye Segment," Int. J. Mol. Sci. 2016, 17, 1825, 23 pages.
Witte K., et al., "Experimental heart failure in rats: effects on cardiovascular circadian rhythms and on myocardial ß-adrenergic signaling," Cardiovasc Res 47 (2): 203-405, 2000.
Wunder F., et al., "A cell-based cGMP assay useful for ultra-high-throughput screening and identification of modulators of the nitric oxide/cGMP pathway," Anal Biochem. Apr. 1, 2005;339(1):104-12.
Zhao, W. et al., "Diabetes-induced biochemical changes in rat lens: attenuation of cataractogenesis by pyruvate," Diabetes, Obesity and Metabolism 2000, 2, pp. 165-174.
Zhao, Y. et al., "The role of anti-vascular endothelial growth factor (anti-VEGF) in the management of proliferative diabetic retinopathy," Drugs in Context 2018, 7: 212532, 10 pages.
Altaweel, Best Disease: Treatment & Medication, www.emedicine.com, Feb. 11, 2010, printed from http://emedicine.medscape.com/ article/1227128-treatment, 2 pages.
Mayo Clinic, Stargardt's disease: Can it be treated?, 2006, printed May 27, 2008, MayoClinic.com, http://www.mayoclinic.com/print/stargardts-disease/AN00846/METHOD=print, 2 pages.
Merck Manuals, Retinitis Pigmentosa, 2005, http://www.merck.com/mmpe/print/sec09/ch106/ch106h.html, printed May 27, 2008, 2 pages.
Northwestern Medicine, Causes and Diagnoses of Diabetic Retinopathy, Mar. 27, 2024, www.nm.org, printed from https:// www.nm.org/conditions-and-care-areas/ophthalmology/diabetic-retinopathy/causes-and-diagnoses, 2 pages.
University of Rochester Medical Center, Diabetic Retinopathy, Mar. 27, 2024, www.urme.rochester.edu, printed from https:// www.urmc.rochester.edu/encyclopedia/content.aspx?contenttypeid=85&contentid=P00497, 7 pages.
Wermuth, The Practice of Medicinal Chemistry—Molecular Variations Based on Isosteric Replacements, 1996, Academic Press Limited, pp. 203 and 226-228 (Year: 1996).

* cited by examiner

Fig. 1: Ortep-Plot (50 %) with labeling scheme (without disorder), example 4
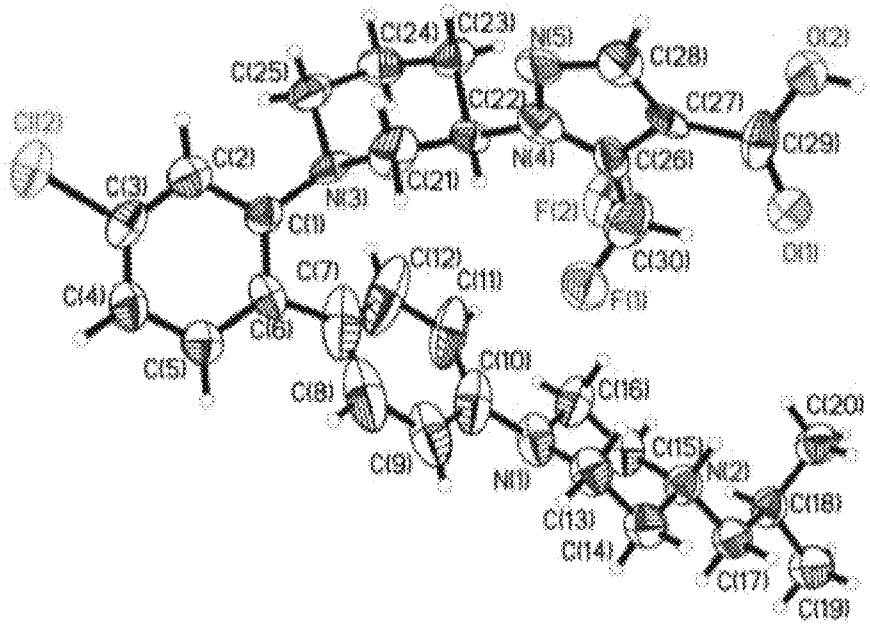

Fig. 2: Independent molecules in the asymmetric unit (with disorder), example 4
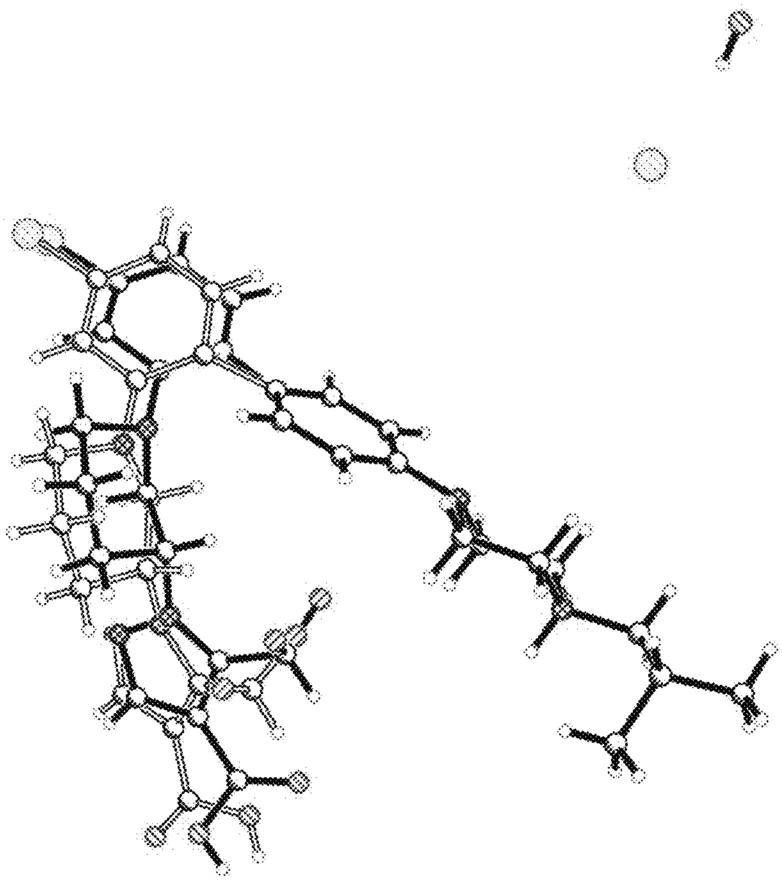

Fig.3: Configuration of C22, example 4
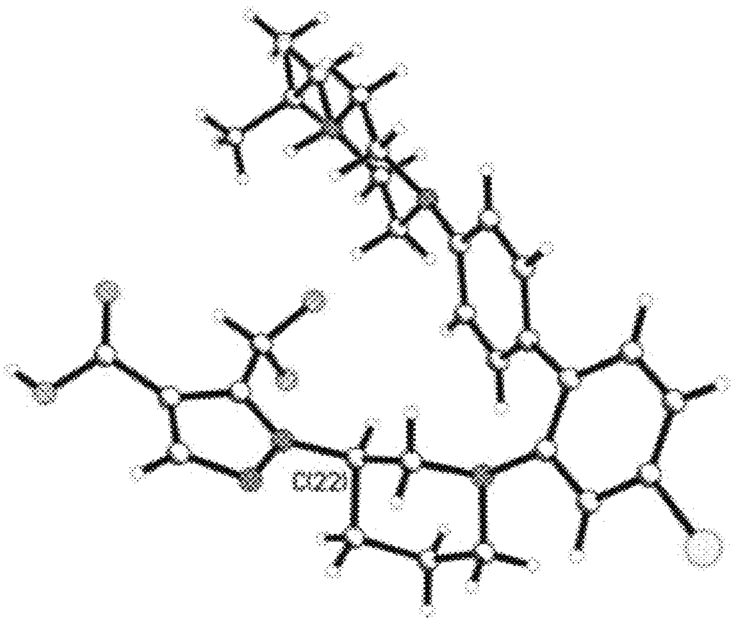

SUBSTITUTED PYRAZOLO PIPERIDINE CARBOXYLIC ACIDS

This application is a U.S. continuation patent application of International PCT Patent Application No. PCT/EP2021/084980, filed Dec. 9, 2021, which is incorporated herein by reference in its entirety, which claims benefit of priority to European Patent Application No. 20213016.7, filed Dec. 10, 2020.

The invention relates to substituted pyrazolo piperidine carboxylic acids, their salts and to processes for their preparation, and also to their use for preparing medicaments for the treatment and/or prophylaxis of diseases, in particular cardiovascular and cardiac diseases, preferably heart failure with reduced and preserved ejection fraction (HFrEF, HFmrEF and HFpEF), hypertension (HTN), peripheral arterial diseases (PAD, PAOD), cardio-renal and kidney diseases, preferably chronic and diabetic kidney disease (CKD and DKD), cardiopulmonary and lung diseases, preferable pulmonary hypertension (PH), and other diseases, preferably neurodegenerative diseases and different forms of dementias, fibrotic diseases, systemic sclerosis (SSc), sickle cell disease (SCD), wound healing disorders such as diabetic foot ulcer (DFU).

In addition, the same above-mentioned pathophysiological mechanisms are effective when blood transfusions (for example by storage etc. with an elevated concentration of free Hb) are administered to patients having a transfusion indication.

Furthermore, in the future the combination of an sGC activator with a synthetic Hb-based oxygen carrier may mitigate the side effects hitherto observed [Weiskopf, Anaesthesia & Analgesia, 110:3; 659-661, 2010] which are caused by reduced availability of NO, thus allowing clinical application.

One of the most important cellular transmission systems in mammalian cells is cyclic guanosine monophosphate (cGMP). Together with nitric oxide (NO), which is released from the endothelium and transmits hormonal and mechanical signals, it forms the NO/cGMP system. Guanylate cyclases catalyse the biosynthesis of cGMP from guanosine triphosphate (GTP). The representatives of this family disclosed to date can be divided both according to structural features and according to the type of ligands into two groups: the particulate guanylate cyclases which can be stimulated by natriuretic peptides, and the soluble guanylate cyclases which can be stimulated by NO. The soluble guanylate cyclases consist of two subunits and very probably contain one haem per heterodimer, which is part of the regulatory site. The latter is of central importance for the mechanism of activation. NO is able to bind to the iron atom of haem and thus markedly increase the activity of the enzyme. Haem-free preparations cannot, by contrast, be stimulated by NO. Carbon monoxide (CO) is also able to attach to the central iron atom of haem, but the stimulation by CO is distinctly less than that by NO.

Through the production of cGMP and the regulation, resulting therefrom, of phosphodiesterases, ion channels and protein kinases, guanylate cyclase plays a crucial part in various physiological processes, in particular in the relaxation and proliferation of smooth muscle cells, in platelet aggregation and adhesion and in neuronal signal transmission, and in disorders caused by an impairment of the aforementioned processes. Under pathophysiological conditions, the NO/cGMP system may be suppressed, which may lead for example to high blood pressure, platelet activation, increased cellular proliferation and fibrosis, endothelial dysfunction, atherosclerosis, angina pectoris, heart failure, thromboses, stroke and myocardial infarction.

A possible way of treating such disorders which is independent of NO and aims at influencing the cGMP signaling pathway in organisms is a promising approach because of the high efficiency and few side effects which are to be expected.

Compounds, such as organic nitrates, whose effect is based on NO have to date been exclusively used for the therapeutic stimulation of soluble guanylate cyclase. NO is produced by bioconversion and activates soluble guanylate cyclase by attaching to the central iron atom of haem. Besides the side effects, the development of tolerance is one of the crucial disadvantages of this mode of treatment [O. V. Evgenov et al., Nature Rev. Drug Disc. 5 (2006), 755].

Substances which directly stimulate soluble guanylate cyclase, i.e. without previous release of NO, have been identified in recent years. The indazole derivative YC-1 was the first NO-independent but haem-dependent sGC stimulator described [Evgenov et al., ibid.]. Based on YC-1, further substances were discovered which are more potent than YC-1 and show no relevant inhibition of phosphodiesterases (PDE). This led to the identification of the pyrazolopyridine derivatives BAY 41-2272, BAY 41-8543, BAY 63-2521 and BAY 102-1189. Together with the recently published structurally different substances CMF-1571 and A-350619, these compounds form the new class of the sGC stimulators [Evgenov et al., ibid.]. A common characteristic of this substance class is a NO-independent and selective activation of the haem-containing sGC. In addition, the sGC stimulators in combination with NO have a synergistic effect on sGC activation based on a stabilization of the nitrosyl-haem complex. The exact binding site of the sGC stimulators at the sGC is still being debated. If the haem group is removed from the soluble guanylate cyclase, the enzyme still has a detectable catalytic basal activity, i.e. cGMP is still being formed. The remaining catalytic basal activity of the haem-free enzyme cannot be stimulated by any of the stimulators mentioned above [Evgenov et al., ibid.].

In addition, NO— and haem-independent sGC activators, with BAY 58-2667 as prototype of this class, have been identified. Common characteristics of these substances are that in combination with NO they only have an additive effect on enzyme activation, and that the activation of the oxidized or haem-free enzyme is markedly higher than that of the haem-containing enzyme [Evgenov et al., ibid.; J. P. Stasch et al., Br. J. Pharmacol. 136 (2002), 773; J. P. Stasch et al., J. Clin. Invest. 116 (2006), 2552].

Spectroscopic studies show that BAY 58-2667 displaces the oxidized haem group which, as a result of the weakening of the iron-histidine bond, is attached only weakly to the sGC. It has also been shown that the characteristic sGC haem binding motif Tyr-x-Ser-x-Arg is absolutely essential both for the interaction of the negatively charged propionic acids of the haem group and for the action of BAY 58-2667. Against this background, it is assumed that the binding site of BAY 58-2667 at the sGC is identical to the binding site of the haem group [J. P. Stasch et al., J. Clin. Invest. 116 (2006), 2552].

The sGC activator Runcaciguat (Hahn et al., Drugs Future 43 (2018), 738, WO 2012/139888) is in clinical development by BAYER (clinicaltrials.gov/NCT04507061). Our understanding of the redox equilibrium of the sGC in health and diseases is limited. Therefore, the treatment potential of sGC activators is not fully clear yet. However, since oxidative stress could render the sGC enzyme heme-free the sGC activators, sGC activators might have an even broader treatment potential which still needs to be identified and proved in the future.

The compounds described in the present invention are now likewise capable of activating the haem-free form of soluble guanylate cyclase. This is also confined by the fact that these novel activators firstly have no synergistic action with NO at the haem-containing enzyme and that secondly their action cannot be blocked by the haem-dependent inhibitor of soluble guanylate cyclase, 1H-1,2,4-oxadiazolo [4,3-a]-quinoxalin-1-one (ODQ), but is even potentiated by this inhibitor [cf. O. V. Evgenov et al., Nature Rev. Drug Disc. 5 (2006), 755; J. P. Stasch et al., J. Clin. Invest. 116 (2006), 2552].

In WO 2012/058132 substituted pyrazolo pyridine carboxylic acids are disclosed as sGC activators. In contrast to the compounds according to the present invention these compounds do have a heteroaromatic pyridine moiety linking the pyrazole carboxylic acid to the rest of the molecule. Furthermore the pyridine nitrogen has another position than the piperidine nitrogen of the compounds according to the present invention. However these compounds do only show mediocre pharmacokinetic properties, like e.g. moderate clearance (CL) and intermediate half-life and mean residence time (MRT) after intraveneous (iv) administration in preclinical pharmacokinetic models.

It is therefore an object of the present invention to provide novel sGC activator compounds for the treatment and/or prophylaxis of diseases, in particular cardiovascular and cardiac diseases, preferably heart failure with reduced and preserved ejection fraction (HFrEF, HFmrEF and HFpEF), hypertension (HTN), peripheral arterial diseases (PAD, PAOD), cardio-renal and kidney diseases, preferably chronic and diabetic kidney disease (CKD and DKD), cardiopulmonary and lung diseases, preferable pulmonary hypertension (PH), and other diseases, preferably neurodegenerative diseases and different forms of dementias, fibrotic diseases, systemic sclerosis (SSc), sickle cell disease (SCD), wound healing disorders such as diabetic foot ulcer (DFU), in humans and animals, which compounds show a good pharmacokinetic behavior with a good pharmacological activity profile as well as beneficial physico chemical properties (e.g. solubility).

Surprisingly, it has now been found that certain substituted pyrazolo piperidine carboxylic acids as well as their corresponding salts represent highly potent sGC activators with good pharmacokinetic behavior with a good pharmacological activity profile as well as beneficial physico chemical properties (e.g. solubility).

The invention provides compounds of the formula (I)

(I)

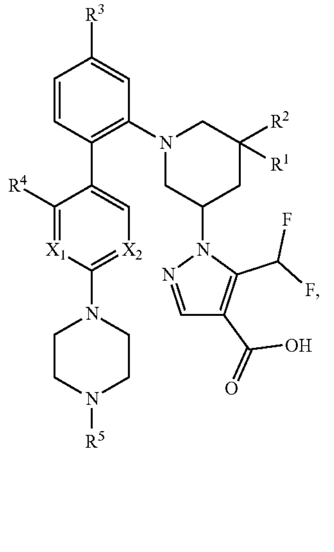

in which $R^1$ represents hydrogen or halogen, $R^2$ represents hydrogen or halogen, $R^3$ represents chloro or trifluoromethyl $R^4$ represents hydrogen or $C_1$-$C_4$-alkyl $R^5$ represents $C_1$-$C_6$-alkyl $X_1$ represents nitrogen or carbon $X_2$ represents nitrogen or carbon and the salts thereof, the solvates thereof and the solvates of the salts thereof.

The term "substituted" means that one or more hydrogen atoms on the designated atom or group are replaced with a selection from the indicated group, provided that the designated atom's normal valence under the existing circumstances is not exceeded. Combinations of substituents and/or variables are permissible.

As used herein, the term "one or more", e.g. in the definition of the substituents of the compounds of general formula (I) of the present invention, means "1, 2, 3, 4 or 5, particularly 1, 2, 3 or 4, more particularly 1, 2 or 3, even more particularly 1 or 2".

In the context of the present invention, unless specified otherwise, the substituents are defined as follows: The term "halogen" or "halogeno" like in combinations e.g. in halogenoalkyl means a fluorine, chlorine, bromine or iodine atom, particularly a fluorine, chlorine or bromine atom, even more particularly fluorine or chlorine.

The term "$C_1$-$C_4$-alkyl", "$C_1$-$C_5$-alkyl" and "$C_1$-$C_6$-alkyl" means a linear or branched, saturated, monovalent hydrocarbon group having 1, 2, 3, or 4 carbon atoms, 1, 2, 3, 4 or 5 carbon atoms, and 1, 2, 3, 4, 5 or 6 carbon atoms, e.g. a methyl, ethyl, propyl, isopropyl, n-butyl, sec-butyl, isobutyl, tert-butyl, pentyl, isopentyl, 2-methylbutyl, 1-methylbutyl, 1-ethylpropyl, 1,2-dimethylpropyl, neo-pentyl, 1,1-dimethylpropyl, hexyl, 1-methylpentyl, 2-methylpentyl, 3-methylpentyl, 4-methylpentyl, 1-ethylbutyl, 2-ethylbutyl, 1,1-dimethylbutyl, 2,2-dimethylbutyl, 3,3-dimethylbutyl, 2,3-dimethylbutyl, 1,2-dimethylbutyl or 1,3-dimethylbutyl group, or an isomer thereof. Particularly, said group has 1, 2, 3 or 4 carbon atoms ("$C_1$-$C_4$-alkyl"), e.g. a methyl, ethyl, propyl, isopropyl, butyl, sec-butyl isobutyl, or tert-butyl group, more particularly 1, 2 or 3 carbon atoms ("$C_1$-$C_3$-alkyl"), e.g. a methyl, ethyl, n-propyl or isopropyl group.

The term "$C_1$-$C_6$-halogenoalkyl", "$C_2$-$C_6$-halogenoalkyl", "$C_1$-$C_4$-halogenoalkyl", "$C_2$-$C_4$-halogenoalkyl", "$C_1$-$C_3$-halogenoalkyl" and "$C_1$-$C_2$-halogenoalkyl" represents a linear or branched, saturated, monovalent hydrocarbon group in which the term "alkyl" is as defined supra, and in which one or more of the hydrogen atoms are replaced, identically or differently, with a halogen atom.

Particularly, said halogen atom is a fluorine atom. Said $C_1$-$C_6$-halogenoalkyl group is, for example fluoromethyl, difluoromethyl, trifluoromethyl, 2-fluoroethyl, 2,2-difluoroethyl, 2,2,2-trifluoroethyl, pentafluoroethyl, 3,3,3-trifluoropropan-1-yl, 1,1,1-trifluoropropan-2-yl, 1,3-difluoropropan-2-yl, 3-fluoropropan-1-yl, 1,1,1-trifluorobutan-2-yl, and 3,3,3-trifluoro-1-methyl-propan-1-yl.

The term "$C_1$-$C_4$-halogenoalkoxy" and "$C_1$-$C_3$-halogenoalkoxy" represents a linear or branched, saturated, monovalent $C_1$-$C_4$-alkoxy or $C_1$-$C_3$-alkoxy group (where alkoxy represents a straight-chain or branched, saturated, monovalent alkoxy radical having 1 to 4 or 1 to 3 carbon atoms, by way of example and with preference methoxy, ethoxy, n-propoxy, isopropoxy), in which one or more of the hydrogen atoms is replaced, identically or differently, with a halogen atom. Particularly, said halogen atom is a fluorine atom. Said $C_1$-$C_3$-halogenoalkoxy group is, for example, fluoromethoxy, difluoromethoxy, trifluoromethoxy, 2,2,2-trifluoroethoxy or pentafluoroethoxy.

The term "$C_3$-$C_6$-cycloalkyl" means a saturated, monovalent, monocyclic hydrocarbon ring which contains 3, 4, 5 or 6 carbon atoms. Said $C_3$-$C_6$-cycloalkyl group is for example a cyclopropyl, cyclobutyl, cyclopentyl or cyclohexyl group.

Compounds according to the invention are the compounds of the formula (I) and the salts, solvates and solvates of the salts thereof, and also the compounds encompassed by formula (I) and specified hereinafter as working example(s), and the salts, solvates and solvates of the salts thereof, to the extent that the compounds encompassed by formula (I) and specified hereinafter are not already salts, solvates and solvates of the salts.

The inventive compounds may, depending on their structure, exist in different stereoisomeric forms, i.e. in the form of configurational isomers or else, if appropriate, of conformational isomers (enantiomers and/or diastereomers, including those in the case of rotamers and atropisomers). The present invention therefore encompasses the enantiomers and diastereomers, and the respective mixtures thereof. The stereoisomerically uniform constituents can be isolated from such mixtures of enantiomers and/or diastereomers in a known manner; chromatography processes are preferably used for this, especially HPLC chromatography on an achiral or chiral phase.

The present invention includes all possible tautomers of the compounds of the present invention as single tautomers, or as any mixture of said tautomers, in any ratio.

In the context of the present invention, the term "enantiomerically pure" is understood to mean that the compound in question with respect to the absolute configuration of the chiral centre is present in an enantiomeric excess of more than 95%, preferably more than 97%. The enantiomeric excess (ee value) is calculated in this case by evaluation of the corresponding HPLC chromatogram on a chiral phase with the aid of the formula below:

$$ee=[E^A(\text{area }\%)-E^B(\text{area }\%)]\times100\%/[E^A(\text{area }\%)+E^B(\text{area }\%)]$$

($E^A$: enantiomer in excess, $E^B$: enantiomer in deficiency)

The present invention also encompasses all suitable isotopic variants of the compounds according to the invention. An isotopic variant of an inventive compound is understood here as meaning a compound in which at least one atom within the inventive compound has been exchanged for another atom of the same atomic number, but with a different atomic mass than the atomic mass which usually or predominantly occurs in nature. Examples of isotopes which can be incorporated into a compound according to the invention are those of hydrogen, carbon, nitrogen, oxygen, phosphorus, sulfur, fluorine, chlorine, bromine and iodine, such as $^2H$ (deuterium), $^3H$ (tritium). $^{13}C$, $^{14}C$, $^{15}N$, $^{17}$, $^{18}O$, $^{32}P$, $^{33}P$, $^{33}S$ $^{34}S$, $^{35}S$, $^{36}S$, $^{18}F$, $^{36}Cl$, $^{82}Br$, $^{123}I$, $^{124}I$ $^{129}I$ and $^{131}I$. Particular isotopic variants of a compound according to the invention, especially those in which one or more radioactive isotopes have been incorporated, may be beneficial, for example, for the examination of the mechanism of action or of the active ingredient distribution in the body; due to comparatively easy preparability and detectability, especially compounds labelled with $^3H$ or $^{14}C$ isotopes are suitable for this purpose. In addition, the incorporation of isotopes, for example of deuterium, may lead to particular therapeutic benefits as a consequence of greater metabolic stability of the compound, for example an extension of the half-life in the body or a reduction in the active dose required; such modifications of the inventive compounds may therefore in some cases also constitute a preferred embodiment of the present invention. Isotopic variants of the compounds according to the invention can be prepared by the processes known to those skilled in the art, for example by the methods described further below and the procedures described in the working examples, by using corresponding isotopic modifications of the respective reagents and/or starting compounds.

Preferred salts in the context of the present invention are physiologically acceptable salts of the compounds according to the invention. However, the invention also encompasses salts which themselves are unsuitable for pharmaceutical applications but which can be used, for example, for the isolation or purification of the compounds according to the invention.

Physiologically acceptable salts of the compounds according to the invention include acid addition salts of mineral acids, carboxylic acids and sulfonic acids, for example salts of hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, trifluoroacetic acid, propionic acid, lactic acid, tartaric acid, malic acid, citric acid, fumaric acid, maleic acid and benzoic acid.

Physiologically acceptable salts of the compounds according to the invention also include salts of conventional bases, by way of example and with preference alkali metal salts (e.g. sodium and potassium salts), alkaline earth metal salts (e.g. calcium and magnesium salts) and ammonium salts derived from ammonia or organic amines having 1 to 16 carbon atoms, by way of example and with preference ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine, N-methylpiperidine and choline.

The present invention includes all possible salts of the compounds according to the invention as single salts, or as any mixture of said salts, in any ratio.

Solvates in the context of the invention are described as those forms of the inventive compounds which form a complex in the solid or liquid state by coordination with solvent molecules. The compounds according to the invention may contain polar solvents, in particular water, methanol or ethanol for example, as structural element of the crystal lattice of the compounds. Hydrates are a specific form of the solvates in which the coordination is with water. It is possible for the amount of polar solvents, in particular water, to exist in a stoichiometric or non-stoichiometric ratio. In the case of stoichiometric solvates, e.g. a hydrate, hemi-, (semi-), mono-, sesqui-, di-, tri-, tetra-, penta- etc. solvates or hydrates, respectively, are possible. The present invention includes all such hydrates or solvates.

Further, the compounds according to the invention can exist as N-oxides, which are defined in that at least one nitrogen of the compounds of the present invention is oxidised in a known manner. The present invention includes all such possible N-oxides.

The present invention additionally also encompasses prodrugs of the inventive compounds. The term "prodrugs" encompasses compounds which for their part may be biologically active or inactive but are converted during their residence time in the body into compounds according to the invention (for example by metabolism or hydrolysis).

Preference is given to compounds of the formula (I) in which $R^1$ represents hydrogen, fluorine $R^2$ represents hydrogen, fluorine $R^3$ represents chloro or trifluoromethyl $R^4$ represents hydrogen or methyl $R^5$ represents $C_1$-$C_5$-alkyl $X_1$ represents nitrogen or carbon $X_2$ represents nitrogen or carbon and the salts thereof, the solvates thereof and the solvates of the salts thereof.

Preference is also given to compounds of the formula (I) in which $R^1$ represents hydrogen, fluorine $R^2$ represents hydrogen, fluorine $R^3$ represents chloro or trifluoromethyl $R^4$ represents hydrogen or methyl $R^5$ represents methyl, ethyl, n-propyl, i-propyl, 2,2,-dimethyl-propyl, isobutyl $X_1$ represents nitrogen or carbon $X_2$ represents nitrogen or carbon and the salts thereof, the solvates thereof and the solvates of the salts thereof.

Preference is also given to compounds of the formula (I) in which $R^1$ represents hydrogen $R^2$ represents hydrogen $R^3$ represents chloro or trifluoromethyl $R^4$ represents hydrogen or methyl $R^5$ represents methyl, ethyl, n-propyl, i-propyl, 2,2,-dimethyl-propyl, isobutyl $X_1$ represents carbon or nitrogen $X_2$ represents carbon and the salts thereof, the solvates thereof and the solvates of the salts thereof.

Preference is also given to compounds of the formula (I) in which $R^1$ represents hydrogen $R^2$ represents hydrogen $R^3$ represents chloro or trifluoromethyl $R^4$ represents hydrogen $R^5$ represents methyl, ethyl, n-propyl, i-propyl, 2,2,-dimethyl-propyl, isobutyl $X_1$ represents carbon $X_2$ represents carbon and the salts thereof, the solvates thereof and the solvates of the salts thereof.

Preference is also given to compounds of the formula (I) in which $R^1$ represents hydrogen $R^2$ represents hydrogen $R^3$ represents chloro $R^4$ represents hydrogen $R^5$ represents isobutyl $X_1$ represents carbon $X_2$ represents carbon and the salts thereof, the solvates thereof and the solvates of the salts thereof.

Preference is also given to compound of the formula

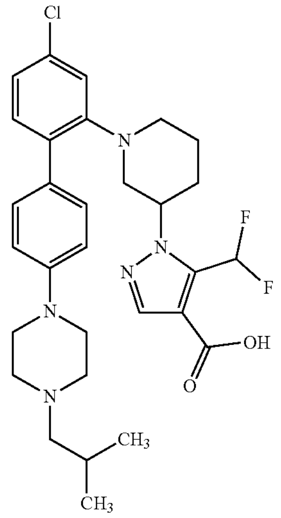

and the salts thereof, solvates thereof or solvates of the salts thereof.

Preference is also given to compound of the formula

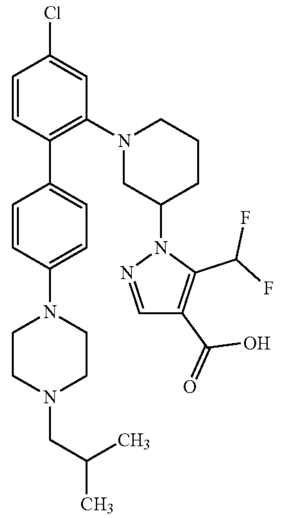 [SMILES: CC(C)CN1CCN(c2ccc(-c3ccc(Cl)cc3N3CCCC(n4ncc(C(=O)O)c4C(F)F)C3)cc2)CC1]

enantiomer 1, and the salts thereof, solvates thereof or solvates of the salts thereof.

Preference is also given to compound of the formula

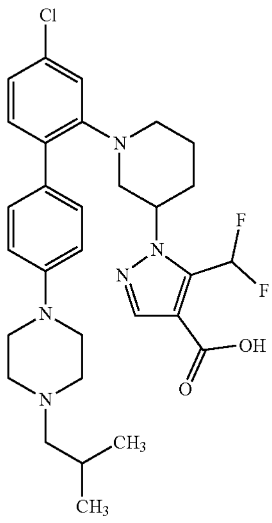 [SMILES: CC(C)CN1CCN(c2ccc(-c3ccc(Cl)cc3N3CCCC(n4ncc(C(=O)O)c4C(F)F)C3)cc2)CC1]

enantiomer 2, and the salts thereof, solvates thereof or solvates of the salts thereof.

Preference is also given to compound of the formula

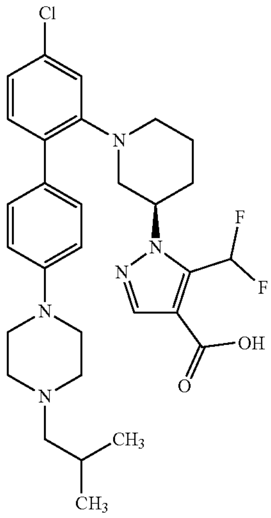

and the salts thereof, solvates thereof or solvates of the salts thereof.

Preference is also given to compound of the formula

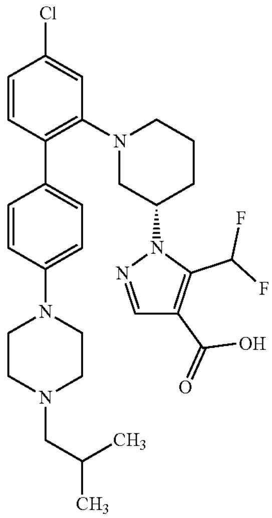 [SMILES: CC(C)CN1CCN(c2ccc(-c3ccc(Cl)cc3N3CCC[C@H](n4ncc(C(=O)O)c4C(F)F)C3)cc2)CC1]

and the salts thereof, solvates thereof or solvates of the salts thereof.

Especially preference is given to compound of formula

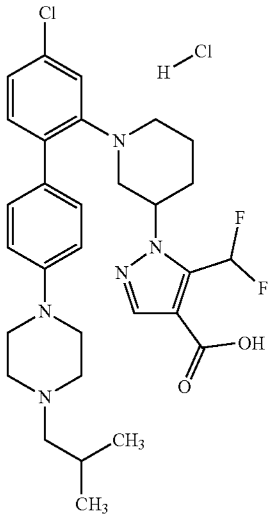

Especially preference is given to compound of formula, enantiomer 1

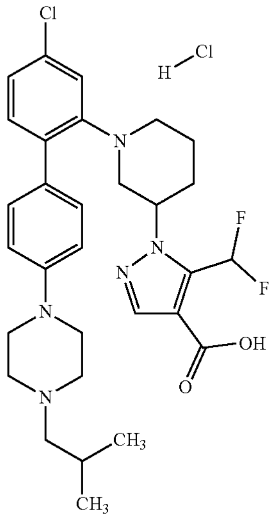

Especially preference is given to compound of formula, enantiomer 2

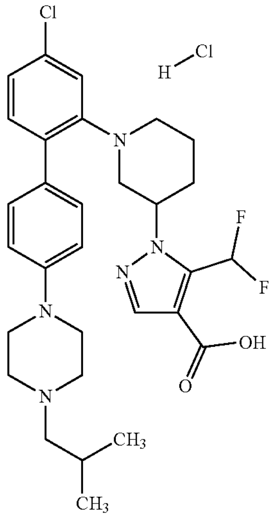

Especially preference is given to compound of formula

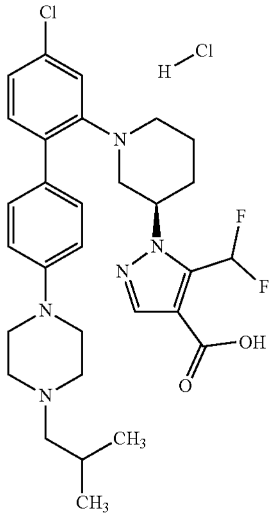

Especially preference is given to compound of formula

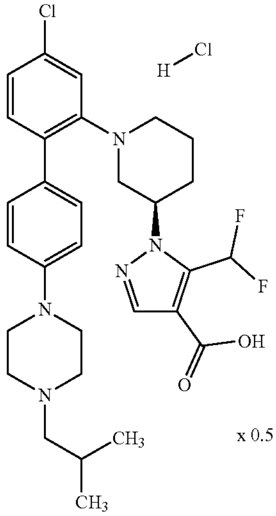

x 0.5 $H_2O$

Especially preference is given to compound of formula

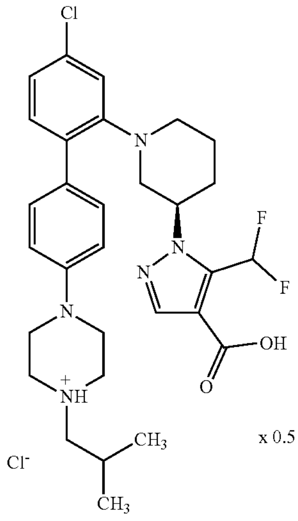

x 0.5 $H_2O$

The invention further provides a process for preparing compounds of the formula (I), or salts thereof, solvates thereof or solvates of the salts thereof, wherein in a first step [B] the compounds of the formula (IV)

(IV)

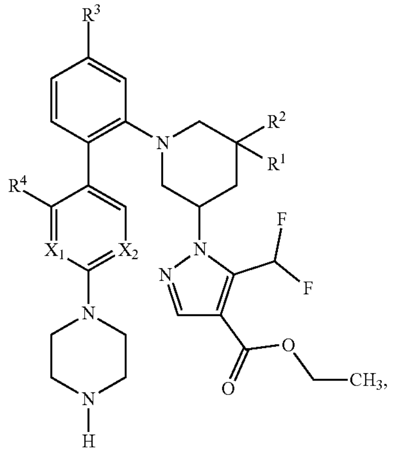

in which $R^1$, $R^2$, $R^3$, $R^4$ and $X_1$ and $X_2$ are defined as above, are reacted with compounds of the formula (III)

$R^{5a}$—CHO (III), in which $R^{5a}$ represents $C_1$-$C_3$-alkyl, preferably isopropyl in the presence of a reducing agent, a suitable base and a suitable solvent to provide compounds of the formula (II)

(II)

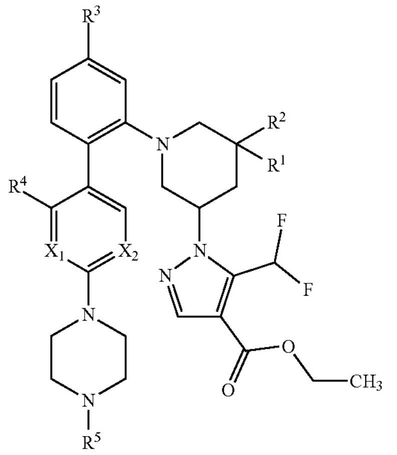

in which $R^1$, $R^2$, $R^3$, $R^4$, $R^5$ and $X_1$ and $X_2$ are defined as above and in a second step [A]

compounds of formula (II)

(II)

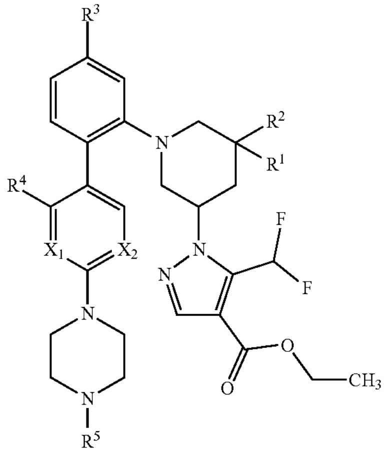

are reacted with a base in a suitable solvent to provide compounds of the formula (I), (I)

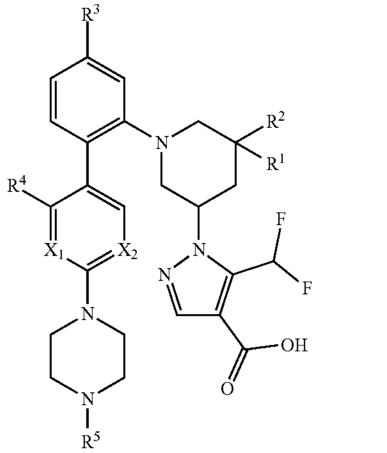

in which $R^1$, $R^2$, $R^3$, $R^4$, $R^5$ and $X_1$ and $X_2$ are defined as above.

Optionally compounds of formula (I) are transferred in a third step [A]* into the corresponding salts of formula (Ia)

(Ia)

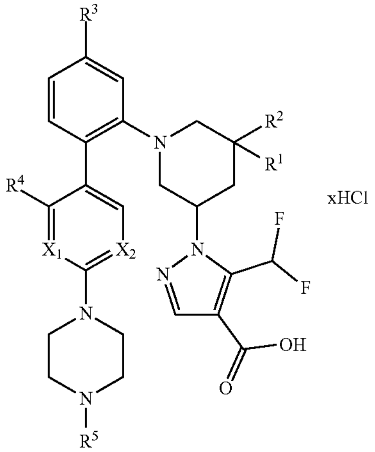

in the presence of a suitable acid in a suitable solvent in which $R^1$, $R^2$, $R^3$, $R^4$, $R^5$ and $X_1$ and $X_2$ are defined as above.

or alternatively in a first step [D] the compounds of the formula (VIII)

(VIII)

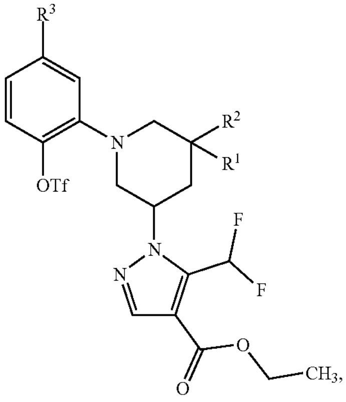

in which $R^1$, $R^2$ and $R^3$ are defined as above, are reacted with compounds of the formula (VII)

(VII)

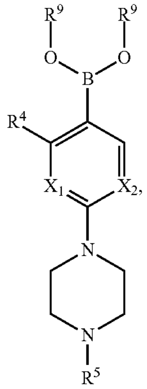

in which $R^4$, $R^5$, and $X_1$ and $X_2$ are defined as above, and in which $R^9$ represents hydrogen, methyl or both $R^9$ form via the adjacent oxygen atoms a 4,4,5,5-tetramethyl-1,3,2-dioxaborolan in the presence of a palladium source, a suitable ligand and a base to provide compounds of the formula (II)

(II)

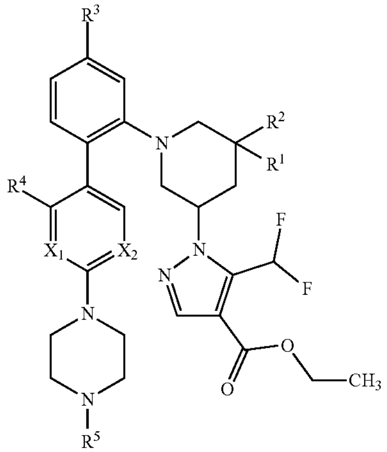

in which $R^1$, $R^2$, $R^3$, $R^4$, $R^5$ and $X_1$ and $X_2$ are defined as above and in a second step [A]

compounds of formula (II)

(II)

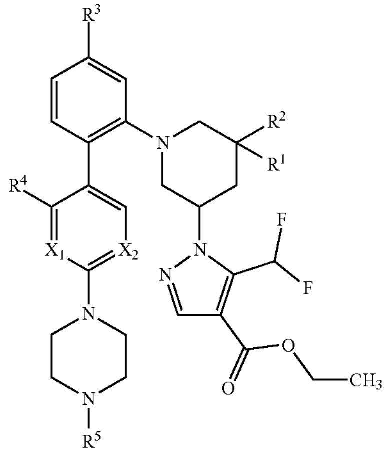

are reacted with a base in a suitable solvent to provide compounds of the formula (I), (I)

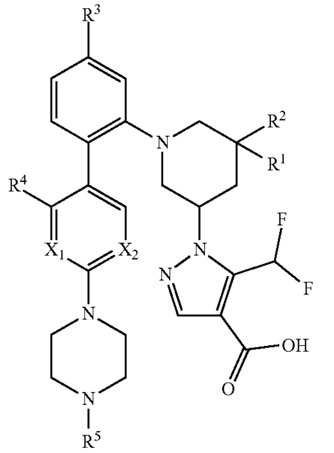

in which $R^1$, $R^2$, $R^3$, $R^4$, $R^5$ and $X_1$ and $X_2$ are defined as above.

Optionally compounds of formula (I) are transferred in a third step [A]* into the corresponding salts of formula (Ia)

(Ia)

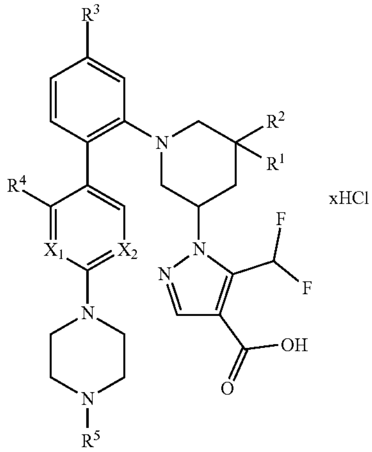

in the presence of a suitable acid in a suitable solvent.

Reaction [A]* (Salt Formation)

The reaction [A]* is generally carried out in inert solvents in the presence of an acid preferably in a temperature range from 0° C. to 60° C. at atmospheric pressure.

Suitable acids for the salt formation are generally sulfuric acid, hydrogen chloride/hydrochloric acid, hydrogen bromide/hydrobromic acid, phosphoric acid, acetic acid, trifluoroacetic acid, toluenesulfonic acid, methanesulfonic acid or trifluoromethanesulfonic acid, or mixtures thereof, optionally with addition of water. Preference is given to hydrogen chloride, hydrogen bromide, toluenesulfonic acid, methanesulfonic acid or sulfuric acid.

Suitable inert solvents for the salt formation are, for example, ethers such as diethyl ether, dioxane, tetrahydrofuran, glycol dimethyl ether or diethylene glycol dimethyl ether, or other solvents such as acetone, ethyl acetate, ethanol, n-propanol, isopropanol, acetonitrile, dimethyl sulphoxide, N,N-dimethylformamide, N,N-dimethylacetamide, N,N'-dimethylpropyleneurea (DMPU) or N-methyl-pyrrolidone (NMP). It is also possible to use mixtures of the solvents mentioned. Preference is given to diethyl ether, dioxane, tetrahydrofuran or mixtures of these solvents.

Reaction [A] (Ester Hydrolyses)

The hydrolysis of the ester group in compounds of formula II is carried out by customary methods, by treating the esters in inert solvents with acids or bases, where in the latter variant the salts initially formed are converted into the free carboxylic acids by treatment with acid. In the case of the tert-butyl esters, the ester hydrolysis is preferably effected with acids.

Suitable inert solvents for these reactions are water or the organic solvents customary for ester cleavage. These preferably include alcohols such as methanol, ethanol, n-propanol, isopropanol, n-butanol or tert-butanol, ethers such as diethyl ether, tetrahydrofuran, 1,4-dioxane or 1,2-dimethoxyethane, or other solvents such as dichloromethane, acetone, methyl ethyl ketone, N,N-dimethylformamide or dimethyl sulphoxide. It is equally possible to use mixtures of these solvents. In the case of a basic ester hydrolysis, preference is given to using mixtures of water with dioxane, tetrahydrofuran, methanol, ethanol and/or dimethylformamide or mixtures of tetrahydrofuran and methanol or ethanol. In the case of the reaction with trifluoroacetic acid, preference is given to using dichloromethane, and in the case of the reaction with hydrogen chloride preference is given to using tetrahydrofuran, diethyl ether, dioxane or water.

Suitable bases are the customary inorganic bases. These especially include alkali metal or alkaline earth metal hydroxides, for example lithium hydroxide, sodium hydroxide, potassium hydroxide or barium hydroxide, or alkali metal or alkaline earth metal carbonates, such as sodium carbonate, potassium carbonate or calcium carbonate. Preference is given to lithium hydroxide, sodium hydroxide or potassium hydroxide.

Suitable acids for the ester hydrolysis are generally sulfuric acid, hydrogen chloride/hydrochloric acid, hydrogen bromide/hydrobromic acid, phosphoric acid, acetic acid, trifluoroacetic acid, toluenesulfonic acid, methanesulfonic acid or trifluoromethanesulfonic acid, or mixtures thereof, optionally with addition of water. Preference is given to hydrogen chloride or trifluoroacetic acid in the case of the tert-butyl esters and to hydrochloric acid in the case of the methyl esters.

The ester hydrolysis is generally carried out within a temperature range from −20° C. to +120° C., preferably at 0° C. to +80° C.

The compounds of the formula (II)

(II)

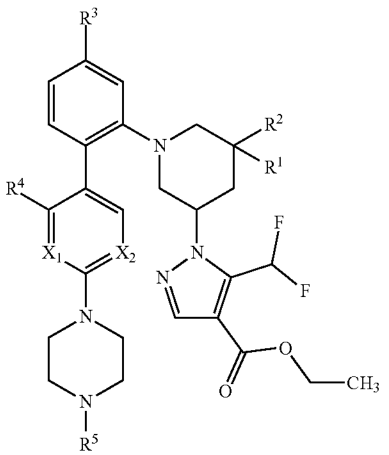

in which $R^1$, $R^2$, $R^3$, $R^4$, $R^5$ and $X_1$ and $X_2$ are defined as above are novel.

The compounds of the formula (II) can be synthesized from the corresponding starting compounds of formula (IV) by

[B] reacting the compounds of the formula (IV)

(IV)

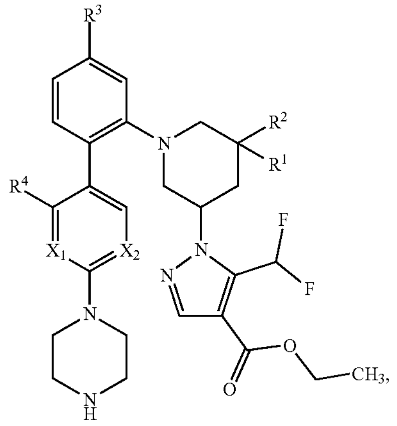

in which $R^1$, $R^2$, $R^3$, $R^4$ and $X_1$ and $X_2$ are defined as above, with compounds of the formula (III)

$R^{5a}$—CHO (III), in which $R^{5a}$ represents $C_1$-$C_3$-alkyl, preferably isopropyl, in the presence of a reducing agent, a suitable base and a suitable solvent to provide compounds of the formula (II)

(II)

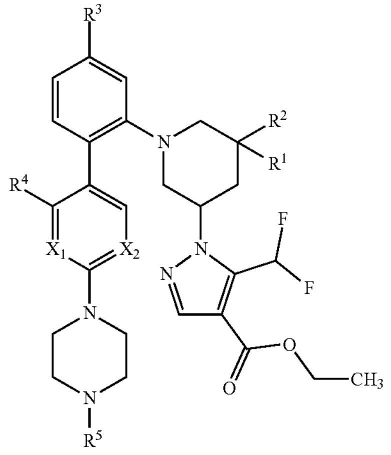

in which $R^1$, $R^2$, $R^3$, $R^4$, $R^5$ and $X_1$ and $X_2$ are defined as above.

Reaction [B] (Reductive Amination)

The reaction of step [B] is generally carried out in inert solvents in the presence of a reducing agent, if appropriate in the presence of a base and or optionally a dehydrating agent, preferably in a temperature range from 0° C. to 60° C. at atmospheric pressure.

Suitable reducing agents for reductive aminations are alkali metal borohydrides customary for such purposes such as sodium borohydride, sodium cyanoborohydride or sodium triacetoxyborohydride; preference is given to using sodium triacetoxyborohydride.

The addition of an acid, such as acetic acid in particular, and/or of a dehydrating agent, for example molecular sieve or trimethyl orthoformate or triethyl orthoformate, may be advantageous in these reactions.

Bases are, for example organic bases such as trialkylamines, for example triethylamine, N-methylmorpholine, N-methylpiperidine, 4-dimethylaminopyridine or diisopropylethylamin, or pyridine.

Bases, such as N,N-diisopropylethylamine and triethylamine in particular, may be advantageous in these reactions.

Suitable solvents for these reactions are especially alcohols such as methanol, ethanol, n-propanol or isopropanol, ethers such as diisopropyl ether, methyl tert-butyl ether, tetrahydrofuran, 1,4-dioxane or 1,2-dimethoxyethane, polar aprotic solvents such as acetonitrile or N,N-dimethylformamide (DMF) or mixtures of such solvents; preference is given to using tetrahydrofuran.

The reactions are generally conducted within a temperature range of 0° C. to +60° C.

The aldehydes of formula (III) are commercial available, known or can be synthesized from known starting materials by known processes.

Compounds of the Formula (IV)

(IV)

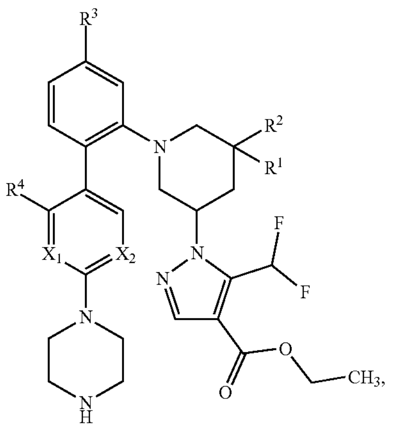

in which $R^1$, $R^2$, $R^3$, $R^4$ and $X_1$ and $X_2$ are defined as above, are novel.

The compounds of the formula (IV) can be synthesized from the corresponding compounds of formula (V) by

[C] reacting the compounds of the formula (V)

(V)

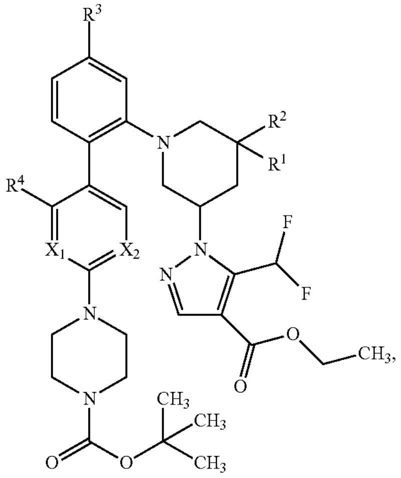

in which $R^1$, $R^2$, $R^3$, $R^4$ and $X_1$ and $X_2$ are defined as above, in the presence of a suitable acid and a suitable solvent.

Reaction [C] (Deprotection)

The reaction [C] is generally carried out in inert solvents in the presence of a suitable acid, preferably in a temperature range from 0° C. to 60° C. at atmospheric pressure.

Acids are, for example organic or inorganic acids such as sulfuric acid, hydrogen chloride/hydrochloric acid, hydrogen bromide/hydrobromic acid, phosphoric acid, acetic acid, trifluoroacetic acid, toluenesulfonic acid, methanesulfonic acid or trifluoromethanesulfonic acid, or mixtures thereof, optionally with addition of water. Preference is given to hydrogen chloride or trifluoroacetic acid.

Suitable solvents for these reactions are especially alcohols such as methanol, ethanol, n-propanol or isopropanol, ethers such as diisopropyl ether, methyl tert-butyl ether, tetrahydrofuran, 1,4-dioxane or 1,2-dimethoxyethane, polar aprotic solvents such as acetonitrile or N,N-dimethylformamide (DMF) or mixtures of such solvents; preference is given to using tetrahydrofuran.

The reactions are generally conducted within a temperature range of 0° C. to +60° C.

Compounds of Formula (V)

(V)

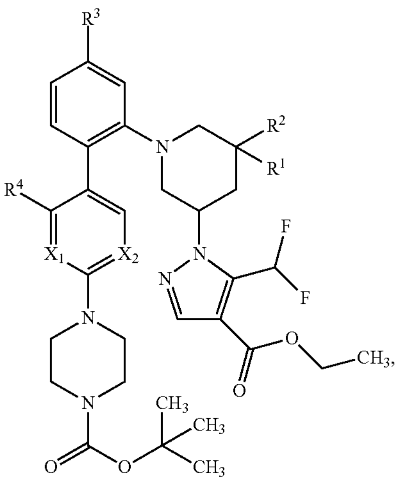

in which $R^1$, $R^2$, $R^3$, $R^4$ and $X_1$ and $X_2$ are defined as above are novel.

The compounds of the formula (V) can be synthesized from the corresponding compounds of formula (VIII) by [G] reacting the compounds of the formula (VIII)

(VIII)

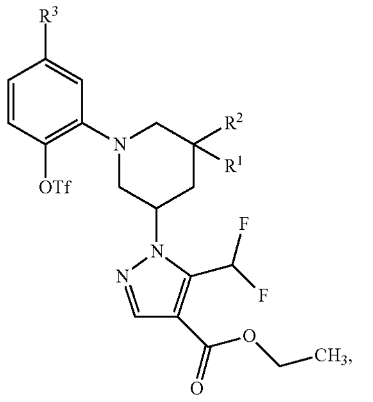

in which $R^1$, $R^2$ and $R^3$ are defined as above, in the presence of a suitable palladium catalyst, base and a suitable solvent with compounds of the formula (VI)

(VI)

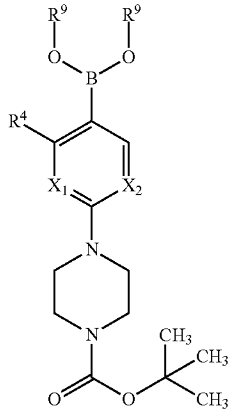

in which $R^4$, $R^9$ and $X_1$ and $X_2$ are defined as above.

Reaction [G] (Suzuki Coupling)

The reaction [G] is generally carried out in the presence of a suitable palladium catalyst and a suitable base in inert solvents, preferably at temperature range from room temperature up to reflux of the solvents at atmospheric pressure.

Inert solvents for reaction step [G] are for example alcohols like methanol, ethanol, n-propanol, isopropanol, n-butanol or tert.-butanol, ether like diethylether, dioxane, tetrahydrofuran, glycoldimethylether or diethylenglycoldimethylether, hydrocarbons like benzene, xylol, toluene, hexane, cyclohexane or petroleum oil, or other solvents like dimethylformamide (DMF), dimethylsulfoxide (DMSO), N,N'-dimethylpropylene urea (DMPU), N-methylpyrrolidone (NMP), pyridine, acetonitrile or also water. It is also possible to utilize mixtures of the aforementioned solvents. Preferred is a mixture of dimethylformamide/water and toluene/ethanol.

Suitable bases for reaction steps are the customary inorganic bases. These especially include alkali metal or alkaline earth metal hydroxides, for example lithium hydroxide, sodium hydroxide, potassium hydroxide or barium hydroxide alkali metal hydrogencarbonates like sodium or potassium-hydrogencarbonate, or alkali metal or alkaline earth metal carbonates such as lithium, sodium, potassium, calcium or cesium carbonate, or alkali hydrogenphosphates like disodium or dipotassium hydrogenphosphate. Preferably used bases are sodium or potassium carbonate.

Examples of suitable palladium catalysts for reaction steps ["Suzuki-coupling" ] are e.g. palladium on charcoal, palladium(II)-acetate, tetrakis-(triphenylphosphine)-palladium(0), bis-(triphenylphosphine)-palladium(II)-chloride, bis-(acetonitrile)-palladium(II)-chloride and [1,1'-bis(diphenylphosphino)ferrocene]dichloropalladium(II)-dichlormethane-complex [cf. e.g. Hassan J. et al., *Chem. Rev.* 102, 1359-1469 (2002)].

The reaction steps are generally carried out within a temperature range from +20° C. to +150° C., preferably at +50° C. to +100° C.

The compounds of the formula (VI) are novel, commercial available or available via known processes.

The Compounds of the Formula (VIII)

(VIII)

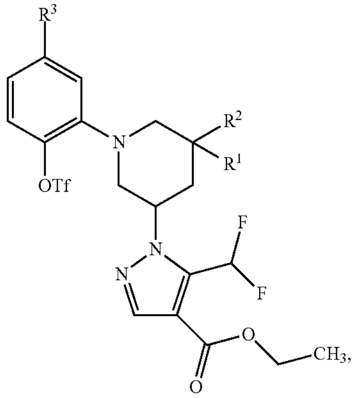

in which $R^1$, $R^2$ and $R^3$ are defined as above are novel.

The compounds of the formula (VIII) can be prepared [H] by reacting compounds of the formula (IX)

(IX)

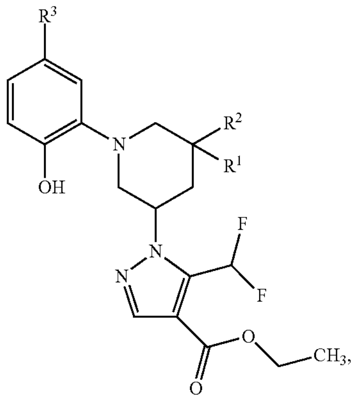

in which $R^1$, $R^2$ and $R^3$ are as defined above, with triflic acid anhydride in the presence of base and an inert solvent.

Reaction [H] (Triflatization)

The reaction [H] is generally carried out with triflic acid anhydride in the presence of base in inert solvents, preferably in a temperature range from room temperature up to reflux of the solvents at atmospheric pressure.

Bases are, for example, organic bases like alkali amines or pyridines or inorganic bases such as sodium hydroxide, lithium hydroxide or potassium hydroxide, or alkali metal carbonates such as caesium carbonate, sodium carbonate or potassium carbonate, or alkoxides such as potassium tert-butoxide or sodium tert-butoxide, or pyridines such as pyridine or 2,6-lutidine, or alkali amines such as triethylamine or N,N-diisopropylethylamine; preference is given to triethylamine.

Inert solvents are, for example, ethers such as diethyl ether, methyl tert-butyl ether, 1,2-dimethoxyethane, dioxane or tetrahydrofuran, or other solvents such as dichloromethane, dimethylformamide, dimethylacetamide, acetonitrile or pyridine, or mixtures of solvents; preference is given to dichloromethane.

The Compounds of the Formula (IX)

(IX)

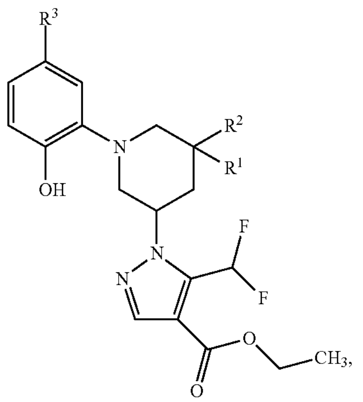

in which $R^1$, $R^2$ and $R^3$ are defined as above are novel.

The compounds of the formula (IX) can be prepared [I] by reacting compounds of the formula (X)

(X)

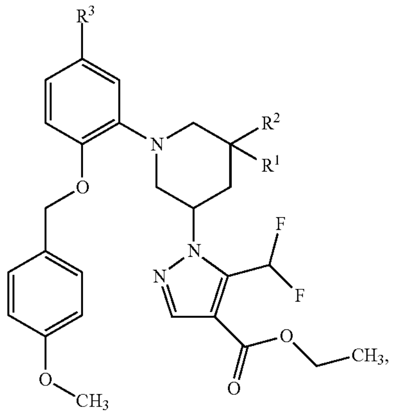

in which $R^1$, $R^2$ and $R^3$ are as defined above, with an acid optionally in an inert solvent.

Reaction [I] (Acidic Deprotection)

The reaction [I] is generally carried out with an acid in inert solvents or without a solvent, preferably in a temperature range from 0° C. up to reflux of the solvents at atmospheric pressure.

Inert solvents are, for example, halogenated hydrocarbons such as dichloromethane, trichloromethane, carbon tetrachloride or 1,2-dichloroethane, alcohols such as methanol or ethanol, ethers such as diethyl ether, methyl tert-butyl ether, 1,2-dimethoxyethane, dioxane or tetrahydrofuran, or other solvents such as dimethylformamide, dimethoxy ethane, N-methyl-pyrrolidone, dimethylacetamide, acetonitrile, acetone or pyridine, or mixtures of solvents; preference is given to dichloromethane or dioxane.

Suitable acids for the acidic deprotection are generally sulfuric acid, hydrogen chloride/hydrochloric acid, hydrogen bromide/hydrobromic acid, phosphoric acid, acetic acid, trifluoroacetic acid, toluenesulfonic acid, methanesulfonic acid or trifluoromethanesulfonic acid, or mixtures thereof, optionally with addition of water. Preference is given to hydrogen chloride or trifluoroacetic acid.

Compounds of the Formula (X)

(X)

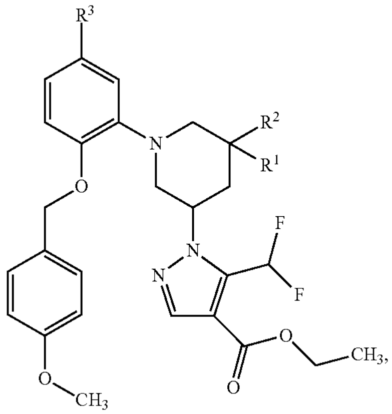

in which $R^1$, $R^2$ and $R^3$ are as defined above are novel.

The compounds of the formula (X) can be prepared [J] by reacting compounds of the formula (XII)

(XII)

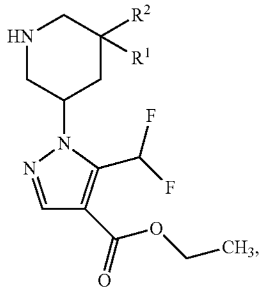

in which $R^1$ and $R^2$ are as defined above, with compounds of the formula (XI)

(XI)

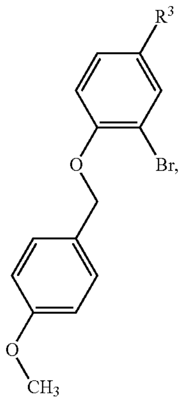

in which $R^3$ is as defined above, in the presence of a palladium source, a suitable ligand and a base.

Reaction [J] (Buchwald Hartwig Coupling)

The reaction [J] is generally carried out in the presence of a palladium source, a suitable ligand and a base in inert solvents, preferably in a temperature range from room temperature up to reflux of the solvents at atmospheric pressure.

The palladium source and a suitable ligand are, for example, palladium on charcoal, palladium(II)-acetate, tris(dibenzylideneacetone)palladium(0), tetrakis-(triphenylphosphine)-palladium(0), bis-(triphenylphosphine)-palladium(II) chloride, bis-(acetonitrile)-palladium(II) chloride, [1,1'-bis(diphenylphosphino)ferrocene]dichloro palladium (II) and corresponding dichloromethan-complex, optionally in conjunction with additional phosphane ligands like for example 2,2'-Bis(diphenylphosphino)-1,1'-binaphthyl (BINAP), (2-dicyclohexylphosphino-2',4',6'-triisopropyl-1,1'-biphenyl)[2-(2'-amino-1,1'-biphenyl)]palladium(II) methanesulfonate (XPhos-Pd-G3, CAS-No: 1445085-55-1), (2-biphenyl)di-tert.-butylphosphine, dicyclohexyl[2',4',6'-tris(1-methylethyl)biphenyl-2-yl]phosphane (XPhos, CAS-No: CAS-No: 564483-18-7), Bis(2-phenylphosphinophenyl)ether (DPEphos), or 4,5-bis(diphenylphosphino)-9,9-dimethylxanthene (Xantphos: CAS-No: 161265-03-8) [cf. e.g. Hassan J. et al., Chem. Rev. 2002, 102, 1359-1469], 2-(dicyclohexylphosphine)-3,6-dimethoxy-2',4',6'-triisopropyl-1,1'-biphenyl (BrettPhos, CAS-No: 1070663-78-3), 2-dicyclohexylphosphino-2',6'-dimethoxybiphenyl (SPhos, CAS-No: 657408-07-6), 2-dicyclohexylphosphino-2',6'-diisopropoxybiphenyl (RuPhos, CAS-No: 787618-22-8), 2-(di-tert-butylphosphino)-3-methoxy-6-methyl-2',4',6'-tri-i-propyl-1,1'-biphenyl (RockPhos) and 2-di-tert-butylphosphino-2',4',6'-triisopropylbiphenyl (tert-ButylXPhos). It is also possible to use corresponding precatalysts such as chloro-[2-(dicyclohexylphosphine)-3,6-dimethoxy-2',4',6'-triisopropyl-1,1'-biphenyl][2-(2-aminoethyl)-phenyl]palladium(II) (BrettPhos precatalysts) [cf. e.g. S. L. Buchwald et al., Chem. Sci. 2013, 4, 916] optionally be used in conjunction with additional phosphine ligands such as 2-(dicyclohexylphosphine)-3,6-dimethoxy-2',4',6'-triisopropyl-1,1'-biphenyl (BrettPhos).

Preference is given to 2,2'-Bis(diphenylphosphino)-1,1'-binaphthyl (BINAP), tris(dibenzylideneacetone)palladium (0), or in combination with 4,5-bis(diphenylphosphino)-9,9-dimethylxanthen (Xantphos) or dicyclohexyl[2',4',6'-tris(1-methylethyl)biphenyl-2-yl]phosphane (XPhos).

Bases are, for example, suitable inorganic or organic bases like e.g. alkali or earth alkali metal carbonates such as lithium, sodium, potassium, calcium or caesium carbonate, or sodium bicarbonate or potassium bicarbonate, alkali metal hydrogencarbonates such as sodium hydrogencarbonate or potassium hydrogencarbonate, alkali metal or earth alkali hydroxides such as sodium, barium or potassium hydroxide; alkali metal or earth alkali phosphates like potassium phosphate; alkali metal alcoholates like sodium or potassium tert.-butylate and sodium methanolate, alkali metal phenolates like sodium phenolate, potassium acetate, amides like sodium amide, lithium-, sodium- or potassium-bis(trimethyl-silyl)amide or lithium diisopropylamide or organic amines like 1,5-diazabicyclo[4.3.0]non-5-ene (DBN), 1,8-diazabicyclo[5.4.0]undec-7-en (DBU). Preference is given to caesium carbonate, sodium carbonate, potassium carbonate or sodium hydrogencarbonate.

Inert solvents are, for example, ethers such as dioxane, diethyl ether, tetrahydrofuran, 2-methyl-tetrahydrofuran, di-n-butylether, cyclopentylmethylether, glycoldimethylether or diethyleneglycol-dimethylether, alcohols like tert.-butanol or amylalcohols or dimethylformamide, dimethylacetamide, dimethyl sulphoxide, N-methylpyrrolidone, toluene or acetonitrile, or mixtures of the solvents; preference is given to tert.-butanol, 1,4-dioxane and toluene.

The compounds of the formula (XI) are known or can be synthesized from the corresponding, commercial available starting compounds by known processes.

The compounds of the formula (XII) are novel (XII)

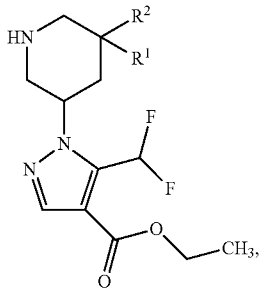

in which $R^1$ and $R^2$ are as defined above.

The compounds of the formula (XII) can be prepared [K] by reacting compounds of the formula (XIII)

(XIII)

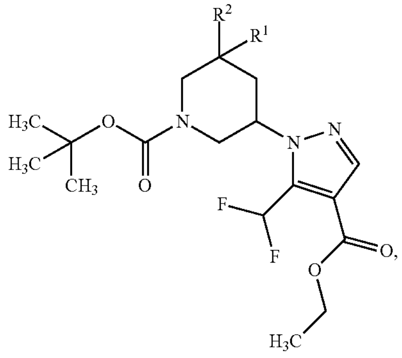

in which $R^1$ and $R^2$ are as defined above, with an acid in an inert solvent.

Reaction [K] (Debocylation)

The reaction [K] is generally carried out in inert solvents in the presence of a suitable acid, preferably in a temperature range from 0° C. to 60° C. at atmospheric pressure.

Acids are for example organic or inorganic acids such as sulfuric acid, hydrogen chloride/hydrochloric acid, hydrogen bromide/hydrobromic acid, phosphoric acid, acetic acid, trifluoroacetic acid, toluenesulfonic acid, methanesulfonic acid or trifluoromethanesulfonic acid, or mixtures thereof, optionally with addition of water. Preference is given to hydrogen chloride or trifluoroacetic acid Inert solvents are alcohols such as methanol, ethanol or isopropanol, ethers such as diethyl ether, diisopropyl ether, methyl tert-butyl ether, tetrahydrofuran or 1,4-dioxane, dichloromethane, polar aprotic solvents such as acetonitrile or N,N-dimethylformamide (DMF) or mixtures of such solvents; preference is given to using 1,4-dioxane.

The Compounds of the Formula (XIII)

(XIII)

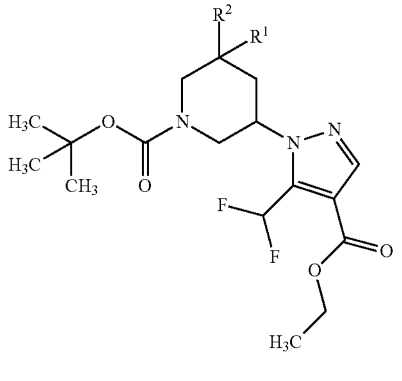

in which $R^1$ and $R^2$ are as defined above, are novel.

The compounds of the formula (XIII) can be prepared [L] by reacting compounds of the formula (XV)

(XV)

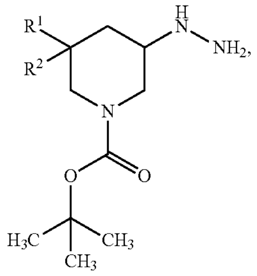

in which $R^1$ and $R^2$ are as defined above, with compounds of the formula (XIV)

(XIV)

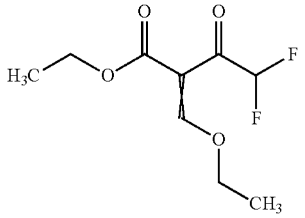

in a solvent.

Reaction [L] (Pyrazole Formation)

The reaction [L] is generally carried out in a solvent at temperatures from room temperature to reflux.

Suitable solvents are alcohols such as methanol, ethanol or isopropanol, ethers such as diethyl ether, diisopropyl ether, methyl tert-butyl ether, tetrahydrofuran or 1,4-dioxane, dichloromethane, polar aprotic solvents such as acetonitrile or N,N-dimethylformamide (DMF) or mixtures of such solvents; preference is given to using ethanol.

The compound of the formula (XIV) are known, commercial available or can be synthesized from the corresponding starting compounds by known processes.

The Compounds of the Formula (XV)

(XV)

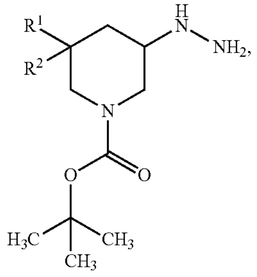

in which $R^1$ and $R^2$ are as defined above are novel.

The compounds of the formula (XV) can be prepared [M] by reacting compounds of the formula (XVI)

(XVI)

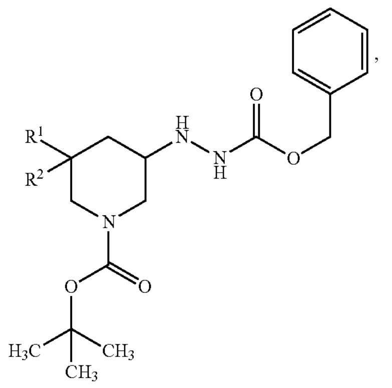

in which $R^1$ and $R^2$ are as defined above with hydrogen in the presence of palladium on charcoal in a suitable solvent.

Reaction [M] (Z Deprotection)

The reaction [M] is generally carried out in the presence of palladium on charcoal in a suitable solvent at from room temperature to reflux, preferable at 1 bar.

Suitable solvents are alcohols such as methanol, ethanol or isopropanol, ethers such as diethyl ether, diisopropyl ether, methyl tert-butyl ether, tetrahydrofuran or 1,4-dioxane, dichloromethane, polar solvents such as acetonitrile, N,N-dimethylformamide (DMF), NMP, acetic acid or water or mixtures of such solvents; preference is given to ethanol/acetic acid.

The Compounds of the Formula (XVI)

(XVI)

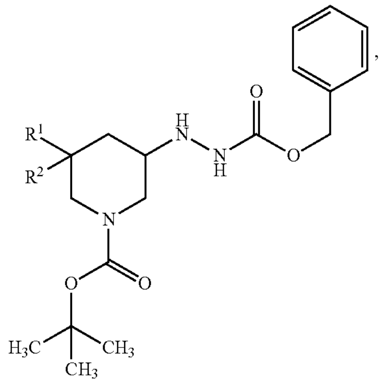

in which $R^1$ and $R^2$ are as defined above are novel.

The compounds of the formula (XVI) can be prepared [N] by reacting compounds of the formula (XVII)

(XVII)

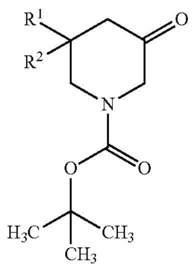

in which $R^1$ and $R^2$ are as defined above with a compound of the formula (XVIII)

(XVIII)

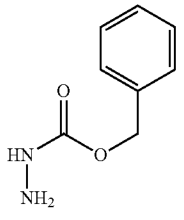

in the presence of a reducing agent and a suitable solvent.

Reaction [N] (Reductive Hydrazination)

Reaction [N] is generally carried out in the presence of a reducing agent and a suitable solvent at a temperature range from room temperature up to reflux of the solvents at atmospheric pressure.

Suitable solvents are alcohols such as methanol, ethanol, n-propanol or isopropanol, ethers such as diisopropyl ether, methyl tert-butyl ether, tetrahydrofuran, 1,4-dioxane or 1,2-dimethoxyethane, polar aprotic solvents such as acetonitrile or N,N-dimethylformamide (DMF) or mixtures of such solvents; preference is given to using tetrahydrofuran/methanol.

Suitable reducing agents are alkali metal borohydrides such as sodium borohydride, sodium cyanoborohydride or sodium triacetoxyborohydride; preference is given to using sodium borohydride.

The compound of the formula (XVIII) is known and commercial available or can be synthesized from the corresponding starting compounds by known processes.

The compound of the formula (XVII) is known and commercial available or can be synthesized from the corresponding starting compounds by known processes.

Alternatively compounds of formula (II) are obtained by [D] reacting compounds of formula (VIII)

(VIII)

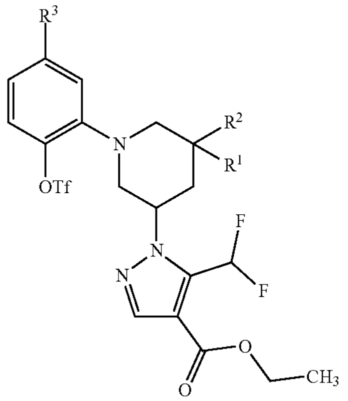

in which $R^1$, $R^2$ and $R^3$ are defined as above
with
compounds of formula (VII)

(VII)

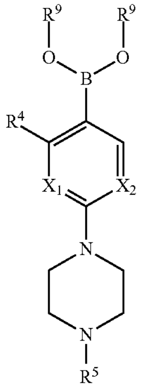

in which $R^4$, $R^5$, $R^9$ and $X_1$ and $X_2$ are defined as above, in the presence of a suitable palladium catalyst a base and a suitable solvent.

Reaction [D] (Suzuki Coupling)

The reaction [D] is generally carried out in the presence of a suitable palladium catalyst a base and in inert solvents, preferably at temperature range from room temperature up to reflux of the solvents at atmospheric pressure.

Inert solvents for reaction [D] are for example alcohols like methanol, ethanol, n-propanol, isopropanol, n-butanol or tert.-butanol, ether like diethylether, dioxane, tetrahydrofuran, glycoldimethylether or diethylenglycoldimethylether, hydrocarbons like benzene, xylol, toluene, hexane, cyclohexane or petroleum oil, or other solvents like dimethylformamide (DMF), dimethylsulfoxide (DMSO), N,N'-dimethylpropylene urea (DMPU), N-methylpyrrolidone (NMP), pyridine, acetonitrile or also water. It is also possible to utilize mixtures of the aforementioned solvents. Preferred is a mixture of dimethylformamide/water and toluene/ethanol.

Suitable bases for reaction steps are the customary inorganic bases. These especially include alkali metal or alkaline earth metal hydroxides, for example lithium hydroxide, sodium hydroxide, potassium hydroxide or barium hydroxide alkali metal hydrogencarbonates like sodium or potassium-hydrogencarbonate, or alkali metal or alkaline earth metal carbonates such as lithium, sodium, potassium, calcium or cesium carbonate, or alkali hydrogenphosphates like disodium or dipotassium hydrogenphosphate. Preferably used bases are sodium or potassium carbonate.

Examples of suitable palladium catalysts for reaction steps ["Suzuki-coupling" ] are e.g. palladium on charcoal, palladium(II)-acetate, tetrakis-(triphenylphosphine)-palladium(0), bis-(triphenylphosphine)-palladium(II)-chloride, bis-(acetonitrile)-palladium(II)-chloride and [1,1'-bis(diphenylphosphino)ferrocene]dichloropalladium(II)-dichloromethane-complex [cf. e.g. Hassan J. et al., *Chem. Rev.* 102, 1359-1469 (2002)].

The reaction steps are generally carried out within a temperature range from +20° C. to +150° C., preferably at +50° C. to +100° C.

The Compounds of the Formula (VIII)

(VIII)

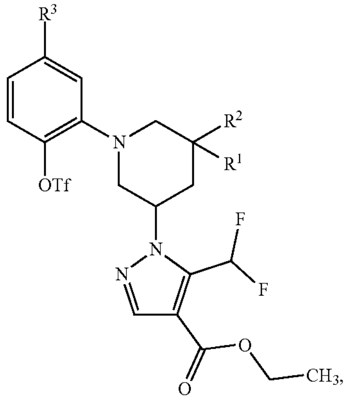

in which $R^1$, $R^2$ and $R^3$ are defined as above are novel.

The synthesis of compounds of formula (VIII) is described above.

The compounds of the formula (VII)

(VII)

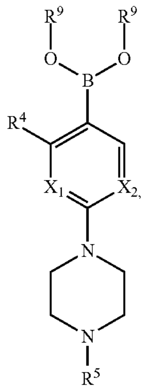

in which $R^4$, $R^5$ and $R^9$ and $X_1$ and $X_2$ are defined as above are novel.

Compounds of formula (VII) are obtained by

[E] reacting compounds of formula (XIX)

(XIX)

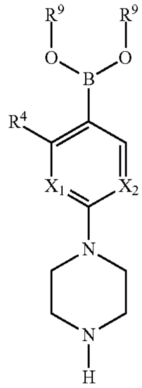

in which $R^4$, $R^5$ and $R^9$ and $X_1$ and $X_2$ are defined as above with
compounds of formula (III)

$R^{5a}$—CHO (III)

in which $R^{5a}$ is defined as above
in the presence of a reducing agent, a suitable base and a suitable solvent.

Reaction [E] (Reductive Amination)

The reaction [E] is generally carried out in inert solvents in the presence of a reducing agent, if appropriate in the presence of a base and or a dehydrating agent, preferably in a temperature range from 0° C. to 60° C. at atmospheric pressure.

Suitable reducing agents for reductive aminations are alkali metal borohydrides customary for such purposes such as sodium borohydride, sodium cyanoborohydride or sodium triacetoxyborohydride; preference is given to using sodium triacetoxyborohydride.

The addition of an acid, such as acetic acid in particular, and/or of a dehydrating agent, for example molecular sieve or trimethyl orthoformate or triethyl orthoformate, may be advantageous in these reactions.

Bases are, for example organic bases such as trialkylamines, for example triethylamine, N-methylmorpholine, N-methylpiperidine, 4-dimethylaminopyridine or diisopropylethylamin, or pyridine.

Bases, such as N,N-diisopropylethylamine and triethylamine in particular, may be advantageous in these reactions.

Suitable solvents for these reactions are especially alcohols such as methanol, ethanol, n-propanol or isopropanol, ethers such as diisopropyl ether, methyl tert-butyl ether, tetrahydrofuran, 1,4-dioxane or 1,2-dimethoxyethane, polar aprotic solvents such as acetonitrile or N,N-dimethylformamide (DMF) or mixtures of such solvents; preference is given to using tetrahydrofuran.

The reactions are generally conducted within a temperature range of 0° C. to +60° C.

The aldehydes of formula (III) are commercial available or can be synthesized from known starting materials by known processes.

The starting material of formula (XTX) is either commercial available, known or available by known processes.

The preparation of the starting compounds and of the compounds of the formula (I) can be illustrated by the synthesis schemes 1 to 5 which follow.

Scheme 1

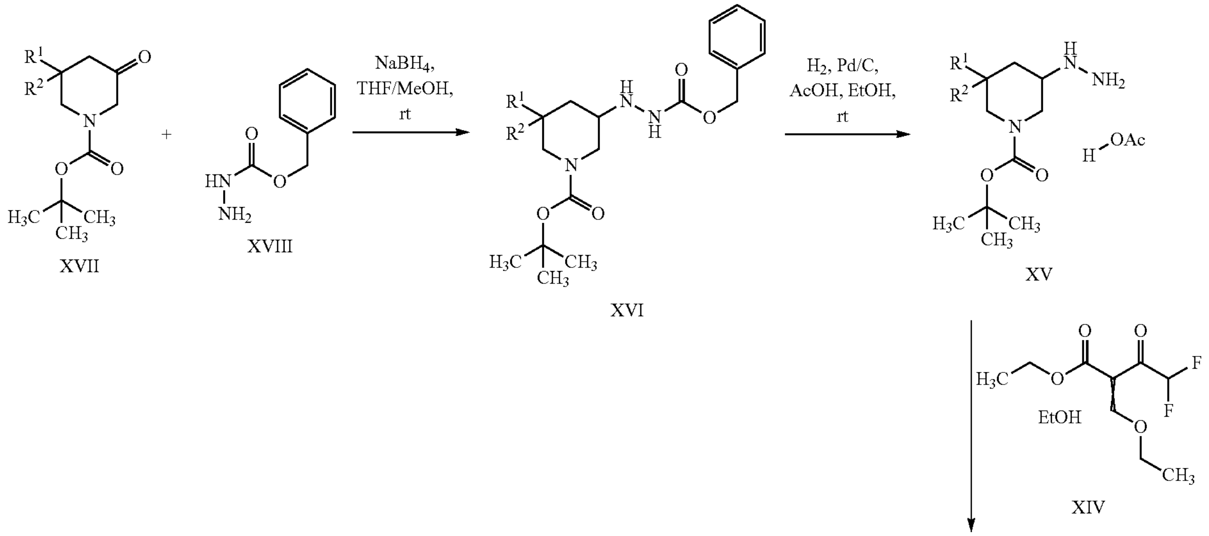

XVII XVIII XVI XV XIV

-continued
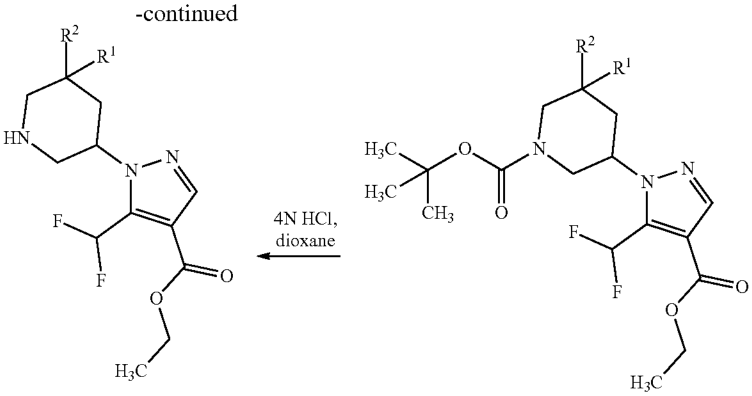
XII
XII-ent
XIII
Scheme 2
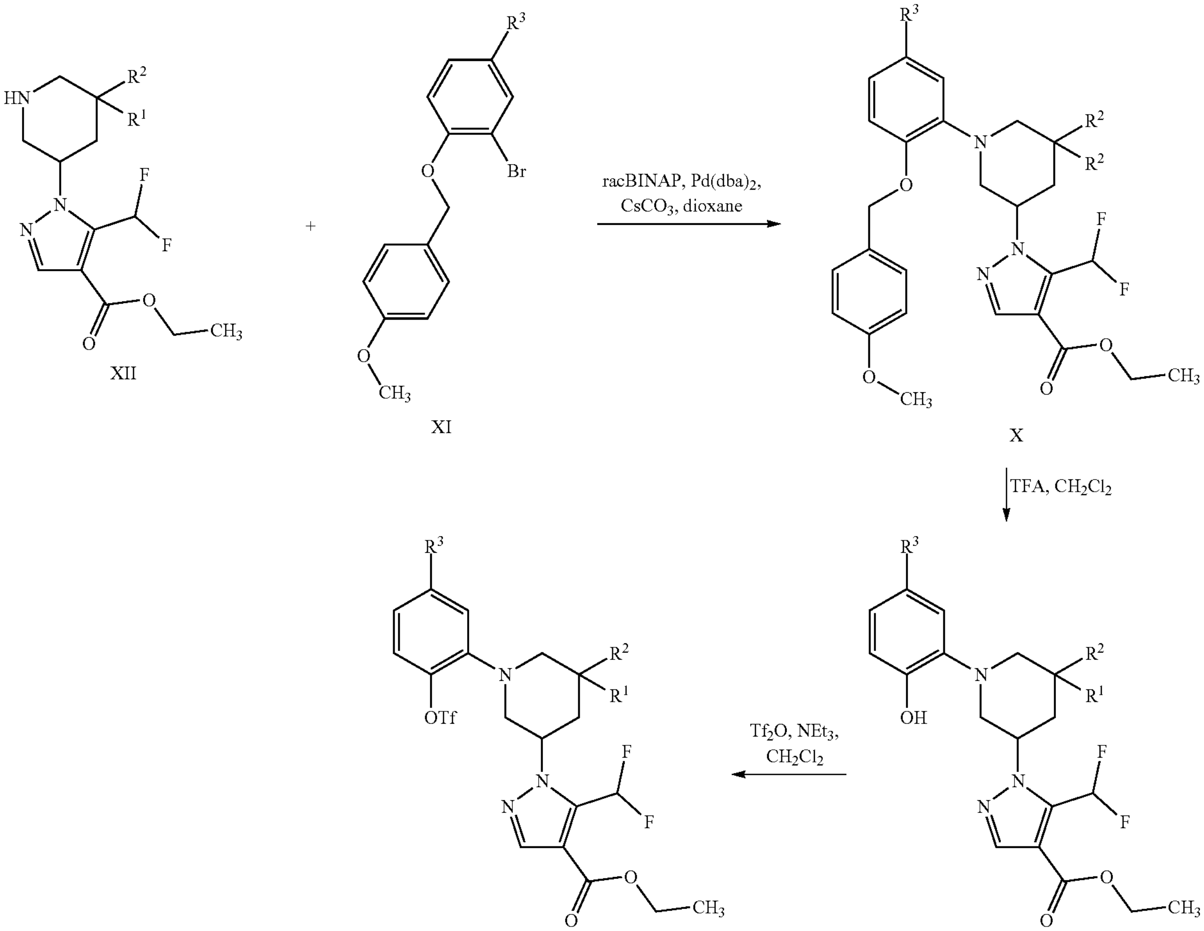
XII
XI
X
VIII
IX

-continued
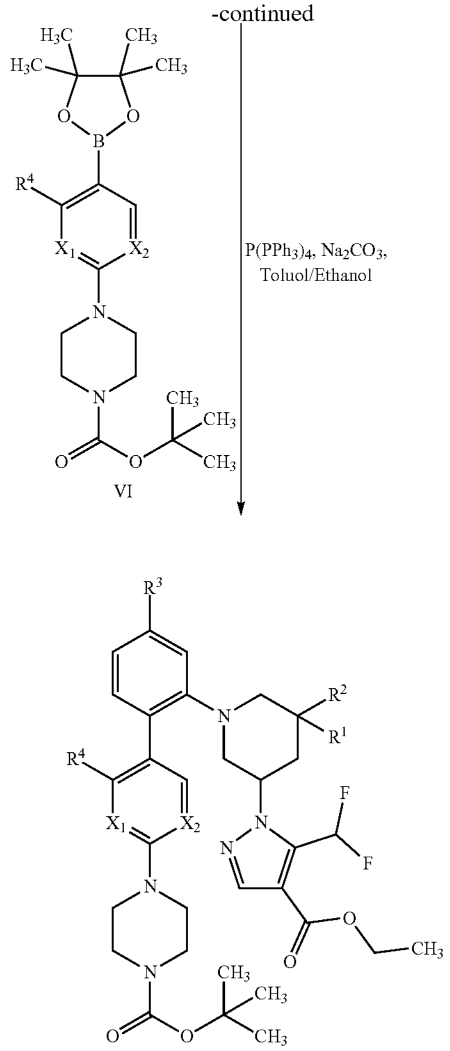
VI
V
Scheme 3
-continued
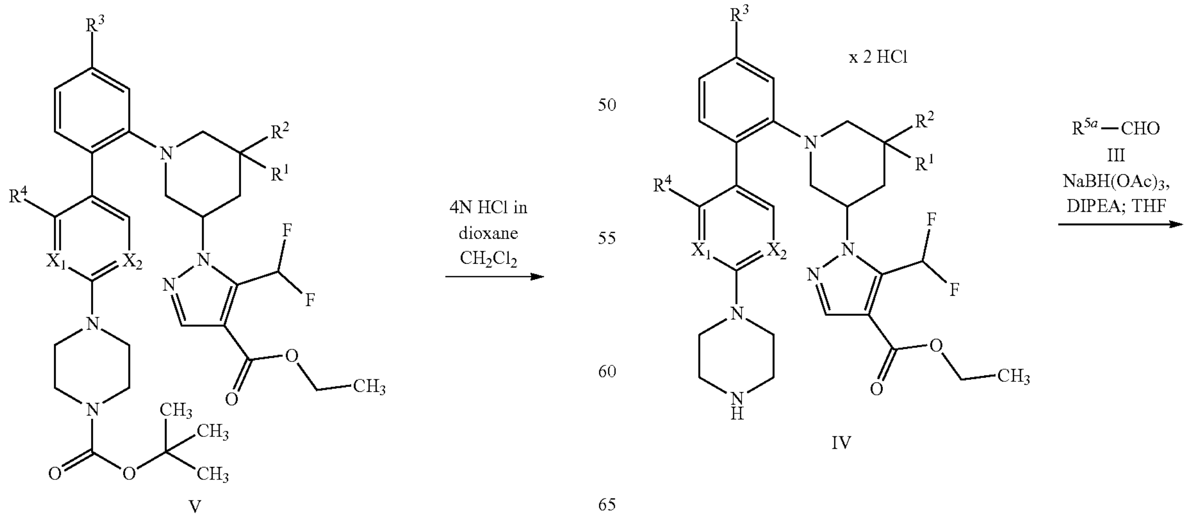
V
IV

-continued
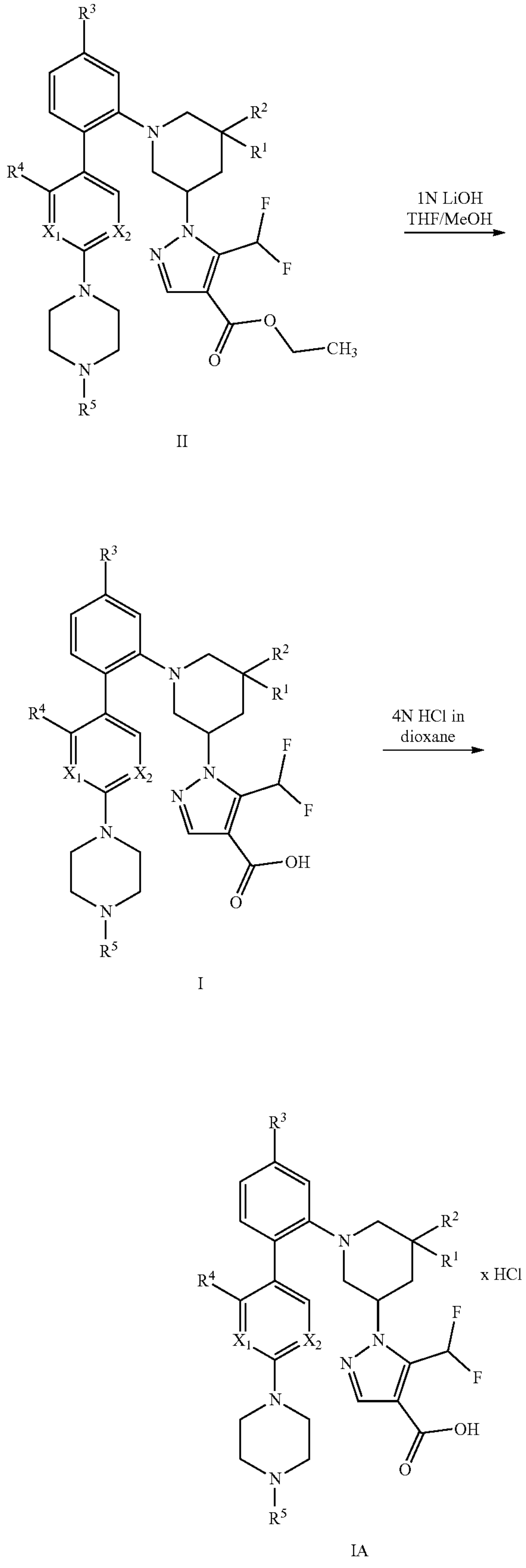
II
I
IA
Scheme 4
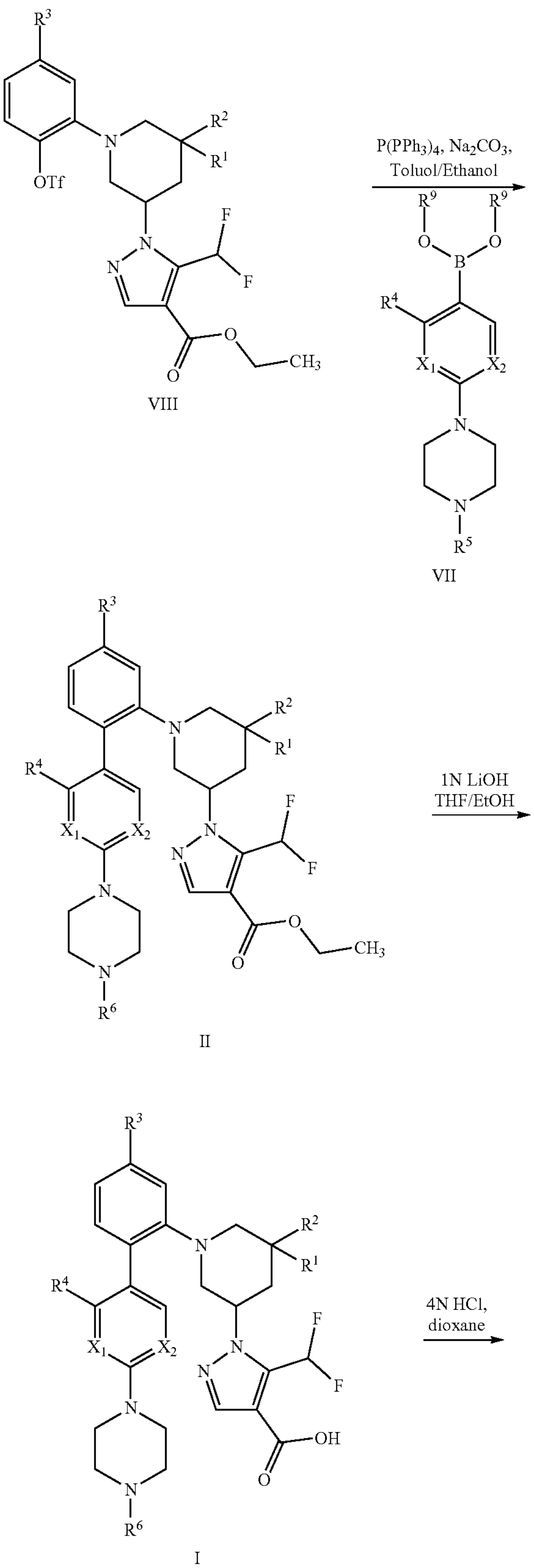
VIII
VII
II
I

-continued

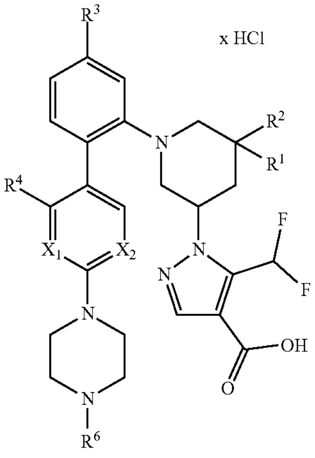

IA

Scheme 5

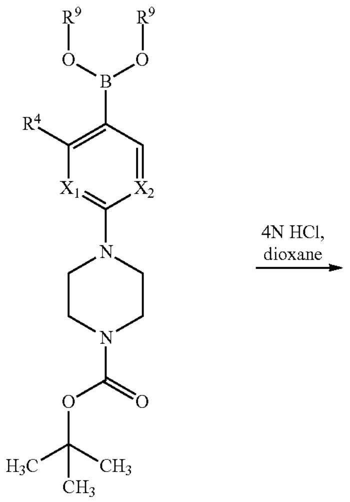

VI

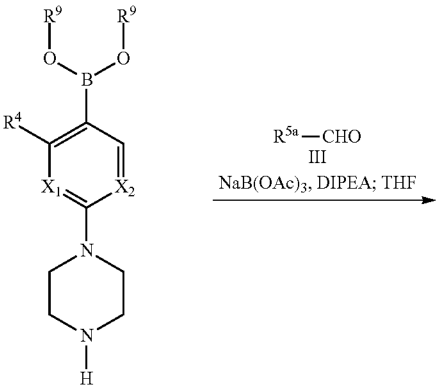

XIX

-continued

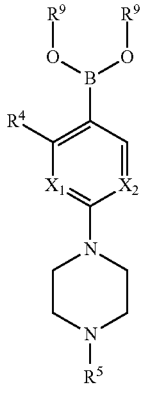

VII

The compounds of the invention have valuable pharmacological properties and can be used for prevention and treatment of diseases in humans and animals.

The compounds according to the invention are potent activators of soluble guanylate cyclase. They lead to vasorelaxation, inhibition of platelet aggregation and lowering of blood pressure and increase of coronary and renal blood flow. These effects are mediated via direct haem-independent activation of soluble guanylate cyclase and an increase of intracellular cGMP.

In addition, the compounds according to the invention have advantageous pharmacokinetic properties, in particular with respect to their bioavailability and/or duration of action after intravenous or oral administration.

The compounds according to the present invention show superior pharmacokinetic (PK) properties in comparison to compounds disclosed in the prior art (WO 2012/058132) (see experimental part, tables 3 to 6). For instance example 2 of the present invention shows a lower plasma clearance ($CL_{plasma}$) (up to 10 times) and therefore a much higher exposure ($AUC_{norm}$) in comparison to the prior art compound disclosed as example 174 in WO 2012/058132 in rats as well as in dogs. Example 2 shows also a long half-life and mean residence time (MRT) in all tested species after p.o. (per oral) application. Due to the significantly lower plasma clearance of example 2 and the resulting very high exposure ($AUC_{norm}$, exposure, area under curve normated) with good bioavailability after p.o. application in all tested species, we see a clear superiority of pharmacokinetic (PK) properties versus example 174 disclosed in WO 2012/058132.

The compounds according to the invention have an unforeseeable useful pharmacological activity spectrum and good pharmacokinetic behavior, in particular a sufficient exposure of such a compound in the blood above the minimal effective concentration within a given dosing interval after oral administration. Such a profile results in an improved peak-to-trough ratio (quotient of maximum to minimum concentration) within a given dosing interval, which has the advantage that the compound can be administered less frequently and at a significantly lower dose to achieve an effect. They are compounds that activate soluble guanylate cyclase.

In the context of the present invention, the term "treatment" or "treating" includes inhibition, retardation, checking, alleviating, attenuating, restricting, reducing, suppressing, repelling or healing of a disease, a condition, a disorder, an injury or a health problem, or the development, the course or the progression of such states and/or the symptoms of such states. The term "therapy" is understood here to be synonymous with the term "treatment".

In the context of the present invention, the terms "prevention", "prophylaxis" and "preclusion" are used synonymously and refer to the avoidance or reduction of the risk of contracting, experiencing, suffering from or having a disease, a condition, a disorder, an injury or a health problem, or a development or advancement of such states and/or the symptoms of such states.

The treatment or prevention of a disease, a condition, a disorder, an injury or a health problem may be partial or complete.

In addition, the compounds according to the invention have further advantageous properties, in particular with respect to their pulmoselective action (in contrast to a systemic action), their lung retention time and/or their duration of action following intrapulmonary administration.

The compounds according to the invention are particularly suitable for the treatment and/or prevention of cardiovascular and cardiac diseases, cardio-renal and kidney diseases, cardiopulmonary and lung diseases, neurodegenerative diseases, thromboembolic diseases, fibrotic disorders and wound healing disorders.

The compounds according to the invention are particularly suitable for the treatment and/or prevention of cardiovascular and cardiac diseases, preferably heart failure with reduced and preserved ejection fraction (HFrEF, HFmrEF and HFpEF), hypertension (HTN), peripheral arterial diseases (PAD, PAOD), cardio-renal and kidney diseases, preferably chronic and diabetic kidney disease (CKD and DKD), cardiopulmonary and lung diseases, preferable pulmonary hypertension (PH), and other diseases, preferably neurodegenerative diseases and different forms of dementias, fibrotic diseases, systemic sclerosis (SSc), sickle cell disease (SCD), wound healing disorders such as diabetic foot ulcer (DFU).

Accordingly, the compounds according to the invention can be used in medicaments for the treatment and/or prevention of cardiovascular, cardiopulmonary and cardiorenal disorders such as, for example high blood pressure (hypertension), heart failure, coronary heart disease, stable and unstable angina pectoris, pulmonary arterial hypertension (PAH) and secondary forms of pulmonary hypertension (PH), chronic thromboembolic pulmonary hypertension (CTEPH), renal, renovascular and treat-ment resistant hypertension, disorders of peripheral and cardiac vessels, arrhythmias, atrial and ventricular arrhythmias and impaired conduction such as, for example, grade I-III atrioventricular blocks, supraventricular tachy-arrhythmia, atrial fibrillation, atrial flutter, ventricular fibrillation, ventricular flutter, ventricular tachy-arrhythmia, Torsade de pointes tachycardia, atrial and ventricular extrasystoles, AV-junctional extrasystoles, sick sinus syndrome, syncopes, AV nodes reentry tachycardia, Wolff-Parkinson-White syndrome, acute coronary syndrome (ACS), autoimmune heart disorders (pericarditis, endocarditis, valvolitis, aortitis, cardiomyopathies), boxer cardiomyopathy, aneurysms, shock such as cardiogenic shock, septic shock and anaphylactic shock, furthermore for the treatment and/or prevention of thromboembolic disorders and ischaemias such as myocardial ischaemia, myocardial infarction, stroke, cardial hypertrophy, transistory and ischaemic attacks, preeclampsia, inflammatory cardiovascular disorders, spasms of the coronary arteries and the peripheral arteries, formation of oedemas such as, for example, pulmonary oedema, brain oedema, renal oedema or heart failure-induced oedema, impaired peripheral perfusion, reperfusion damage, arterial and venous thromboses, microalbuminuria, heart failure, endothelial dysfunction, micro- and macrovascular damage (vasculitis), and also for preventing restenoses for example after thrombolysis therapies, percutaneous transluminal angioplasties (PTA), percutaneous transluminal coronary angioplasties (PTCA), heart transplants and bypass operations.

In the context of the present invention, the term "pulmonary hypertension" encompasses both primary and secondary subforms thereof, as defined below by the Dana Point classification according to their respective aetiology [see D. Montana and G. Simonneau, in: A. J. Peacock et al. (Eds.), *Pulmonary Circulation. Diseases and their treatment,* 3$^{rd}$ edition, Hodder Arnold Publ., 2011, pp. 197-206; M. M. Hoeper et al., *J. Am. Coll. Cardiol.* 2009, 54 (1), S85-S96]. These include in particular in group 1 pulmonary arterial hypertension (PAH), which, among others, embraces the idiopathic and the familial forms (IPAH and FPAH, respectively). Furthermore, PAH also embraces persistent pulmonary hypertension of the newborn and the associated pulmonary arterial hypertension (APAH) associated with collagenoses, congenital systemic pulmonary shunt lesions, portal hypertension, HIV infections, the intake of certain drugs and medicaments (for example of appetite supressants), with disorders having a significant venous/capillary component such as pulmonary venoocclusive disorder and pulmonary capillary haemangiomatosis, or with other disorders such as disorders of the thyroid, glycogen storage diseases, Gaucher disease, hereditary teleangiectasia, haemoglobinopathies, myeloproliferative disorders and splenectomy. Group 2 of the Dana Point classification comprises PH patients having a causative left heart disorder, such as ventricular, atrial or valvular disorders. Group 3 comprises forms of pulmonary hypertension associated with a lung disorder, for example with chronic obstructive lung disease (COPD), interstitial lung disease (ILD), pulmonary fibrosis (IPF), and/or hypoxaemia (e.g. sleep apnoe syndrome, alveolar hypoventilation, chronic high-altitude sickness, hereditary deformities). Group 4 includes PH patients having chronic thrombotic and/or embolic disorders, for example in the case of thromboembolic obstruction of proximal and distal pulmonary arteries (CTEPH) or non-thrombotic embolisms (e.g. as a result of tumour disorders, parasites, foreign bodies). Less common forms of pulmonary hypertension, such as in patients suffering from sarcoidosis, histiocytosis X or lymphangiomatosis, are summarized in group 5.

In the context of the present invention, the term "heart failure" encompasses both acute and chronic forms of heart failure, and also more specific or related types of disease, such as acute decompensated heart failure, right heart failure, left heart failure, global heart failure, also diastolic heart failure and systolic heart failure, heart failure with reduced ejection fraction (HFrEF), heart failure with preserved ejection fraction (HFpEF), heart failure with mid-range efjection fraction (HFmEF), ischemic cardiomyopathy, dilated cardiomyopathy, hypertrophic cardiomyopathy, idiopathic cardiomyopathy, congenital heart defects and cardiomypathies, heart valve defects, heart failure associated with heart valve defects, mitral valve stenosis, mitral valve insufficiency, aortic valve stenosis, aortic valve insufficiency, tricuspid valve stenosis, tricuspid valve insufficiency, pulmonary valve stenosis, pulmonary valve insufficiency, combined heart valve defects, myocardial inflammation (myocarditis), chronic myocarditis, acute myocarditis, viral myocarditis, diabetic heart failure, alcoholic cardiomyopathy, cardiac storage disorders, and also diastolic heart failure and systolic heart failure, heart failure with reduced ejection fraction (HFrEF), heart failure with preserved ejection fraction (HFpEF).

In addition, the compounds according to the invention can also be used for treatment and/or prevention of arteriosclerosis, disturbed lipid metabolism, hypolipoproteinaemias, dyslipidaemias, hypertriglyceridaemias, hyperlipidaemias, combined hyperlipidaemias, hypercholesterolaemias, abetalipoproteinemia, sitosterolemia, xanthomatosis, Tangier disease, adiposity, obesity, and also of metabolic syndrome.

Furthermore, the compounds according to the invention can be used for treatment and/or prevention of primary and secondary Raynaud's phenomenon, of microcirculation disorders, claudication, hearing disorders, tinnitus, peripheral and autonomic neuropathies, diabetic microangiopathies, diabetic retinopathy, diabetic ulcers at the extremities, gangrene, CREST syndrome, erythematosis, onychomycosis and rheumatic disorders.

Futhermore, the compounds according to the invention can be used for the treatment of sickle cell disease (SCD), sickle cell anemia, and also other SCD-related disease symptoms (for example end organ damage affecting lung brain, kidney or heart) but also vasocclusive events or pain crisis, achalasia, hemolyis-induced vasculopathies for treating malaria, thalassemia, hemolytic uremic syndrome, paroxysmal nocturnal hemoglobinuria, drug-Induced hemolytic anemias or rhabdomyolsis. In addition, since similar abovementioned pathophysiological mechanisms are effective when blood transfusions (for example by storage etc. with an elevated concentration of free Hb) are administered to patients having a transfusion indication, this compounds could be used for patients receiving a blood transfusion. Finally, in the future the combination of an sGC activator with a synthetic Hb-based oxygen carrier may mitigate the side effects hitherto observed [Weiskopf, Anaesthesia & Analgesia, 110:3; 659-661, 2010] which are caused by reduced availability of NO, thus allowing further clinical applications.

The compounds according to the invention can additionally also be used for preventing ischaemic and/or reperfusion-related damage to organs or tissues and also as additives for perfusion and preservation solutions of organs, organ parts, tissues or tissue parts of human or animal origin, in particular for surgical interventions or in the field of transplantation medicine.

Furthermore, the compounds according to the invention are suitable for treatment and/or prophylaxis of renal disorders, especially of renal insufficiency and kidney failure. In the context of the present invention, the terms renal insufficiency and kidney failure comprise both acute and chronic manifestations (chronic kidney disease; CKD) thereof, as well as underlying or related kidney diseases such as renal hypoperfusion, intradialytic hypotension, obstructive uropathy, glomerulopathies, glomerulonephritis, acute glomerulonephritis, glomerulosclerosis, tubulointerstitial diseases, nephropathic diseases such as primary and congenital kidney disease, nephritis, immunological kidney diseases such as kidney graft rejection and immunocomplex-induced kidney diseases, nephropathy induced by toxic substances, nephropathy induced by contrast agents, diabetic and non-diabetic nephropathy, diabetic kidney diseas (DKD), pyelonephritis, renal cysts and polycystic kidney disease, nephrosclerosis, hypertensive nephrosclerosis and nephrotic syndrome, which can be characterized diagnostically for example by abnormally reduced creatinine and/or water excretion, abnormally raised blood concentrations of urea, nitrogen, potassium and/or creatinine, altered activity of renal enzymes such as, for example, glutamyl synthetase, altered urine osmolarity or urine volume, increased microalbuminuria, macroalbuminuria, lesions on glomerulae and arterioles, tubular dilation, hyperphosphataemia and/or need for dialysis. The present invention also encompasses the use of the compounds according to the invention for treatment and/or prophylaxis of sequelae of renal insufficiency, for example hypertension, pulmonary oedema, heart failure, uremia, anemia, electrolyte disturbances (for example hypercalemia, hyponatremia) and disturbances in bone and carbohydrate metabolism.

In addition, the compounds according to the invention are suitable for treatment and/or prevention of urological disorders, for example benign prostate syndrome (BPS), benign prostate hyperplasia (BPH), benign prostate enlargement (BPE), bladder outlet obstruction (BOO), lower urinary tract syndrome (LUTS), prostatitis, neurogenic overactive bladder (OAB), incontinence, for example mixed, urge, stress or overflow incontinence (MUI, UUI, SUI, OUI), pelvic pain, interstitial cystitis (IC) and also erectile dysfunction and female sexual dysfunction.

The compounds according to the invention are also suitable for treatment and/or prevention of asthmatic disorders, chronic-obstructive pulmonary diseases (COPD), acute respiratory distress syndrome (ARDS) and acute lung injury (ALI), alpha-1 antitrypsin deficiency (AATD), pulmonary fibrosis, pulmonary emphysema (for example pulmonary emphysema induced by cigarette smoke) and cystic fibrosis (CF).

The compounds described in the present invention are also active compounds for control of central nervous system disorders characterized by disturbances of the NO/cGMP system. They are suitable in particular for improving perception, concentration, learning or memory after cognitive impairments like those occurring in particular in association with situations/diseases/syndromes such as mild cognitive impairment, age-associated learning and memory impairments, age-associated memory losses, vascular dementia, craniocerebral trauma, stroke, dementia occurring after strokes (post stroke dementia), post-traumatic craniocerebral trauma, general concentration impairments, concentration impairments in children with learning and memory problems, Alzheimer's disease, Lewy body dementia, dementia with degeneration of the frontal lobes including Pick's syndrome, Parkinson's disease, progressive nuclear palsy, dementia with corticobasal degeneration, amyolateral sclerosis (ALS), Huntington's disease, demyelination, multiple sclerosis, thalamic degeneration, Creutzfeld-Jacob dementia, HIV dementia, schizophrenia with dementia or Korsakoff's psychosis. They are also suitable for the treatment and/or prevention of central nervous system disorders such as states of anxiety, tension and depression, CNS-related sexual dysfunctions and sleep disturbances, and for controlling pathological disturbances of the is intake of food, stimulants and addictive substances.

Furthermore, the compounds according to the invention are also suitable for regulation of cerebral blood flow and are thus effective agents for control of migraine. They are also suitable for the prophylaxis and control of sequelae of cerebral infarct (Apoplexia cerebri) such as stroke, cerebral ischaemias and craniocerebral trauma. The compounds according to the invention can likewise be used to control states of pain.

Moreover, the compounds according to the invention have antiinflammatory action and can therefore be used as anti-inflammatories for treatment and/or prevention of sepsis (SIRS), multiple organ failure (MODS, MOF), inflammatory disorders of the kidney, chronic bowel inflammations (IBD, Crohn's Disease, UC), pancreatitis, peritonitis, rheumatoid disorders, inflammatory skin disorders and inflammatory eye disorders.

Furthermore, the compounds according to the invention are suitable for the treatment and/or prevention of fibrotic disorders of the internal organs, for example of the lung, of the heart, of the kidneys, of the bone marrow and especially of the liver, and also of dermatological fibroses and fibrotic disorders of the eye. In the context of the present inventions, the term "fibrotic disorders" encompasses especially disorders such as hepatic fibrosis, hepatic cirrhosis, non-alcoholic steato-hepatosis (NASH), pulmonary fibrosis, endomyocardial fibrosis, nephropathy, glomerulonephritis, interstitial renal fibrosis, fibrotic damage resulting from diabetes, myelofibrosis and similar fibrotic disorders, scleroderma, systemic sclerosis, morphea, keloids, hypertrophic scarring, naevi, diabetic retinopathy, proliferative vitreoretinopathy and disorders of the connective tissue (for example sarcoidosis). The compounds according to the invention can likewise be used for promoting wound healing including the healing of digital ulcer and diabeteic foot ulcer, for controlling postoperative scarring, for example resulting from glaucoma operations, and cosmetically for ageing and keratinized skin.

By virtue of their activity profile, the compounds according to the invention are particularly suitable for the treatment and/or prevention of cardiovascular and cardiopulmonary disorders such as primary and secondary forms of pulmonary hypertension, heart failure, angina pectoris and hypertension, and also for the treatment and/or prevention of thromboembolic disorders, ischaemias, vascular disorders, impaired microcirculation, renal insufficiency, fibrotic disorders and arteriosclerosis.

The present invention furthermore provides the use of the compounds according to the invention for the treatment and/or prevention of disorders, in particular the disorders mentioned above.

The present invention furthermore provides the use of the compounds according to the invention for preparing a medicament for the treatment and/or prevention of disorders, in particular the disorders mentioned above.

The present invention furthermore provides a medicament comprising at least one of the compounds according to the invention for the treatment and/or prevention of disorders, in particular the disorders mentioned above.

The present invention furthermore provides the use of the compounds according to the invention in a method for the treatment and/or prevention of disorders, in particular the disorders mentioned above.

The present invention furthermore provides a method for the treatment and/or prevention of disorders, in particular the disorders mentioned above, using an effective amount of at least one of the compounds according to the invention.

They are therefore suitable for use as medicaments for the treatment and/or prophylaxis of diseases in humans and animals.

The present invention further provides for the use of the compounds according to the invention for the treatment and/or prophylaxis of disorders, in particular cardiovascular disorders, preferably thrombotic or thromboembolic disorders and/or thrombotic or thromboembolic complications such as acute coronary syndrome or myocardial infarction or ischemic stroke or peripheral arterial occlusive disease, and/or diabetes and/or urogenital disorders, in particular those associated with.

For the purpose of the present invention, the "thrombotic or thromboembolic disorders" include disorders which occur preferably in the arterial vasculature and which can be treated with the compounds according to the invention, in particular disorders leading to peripheral arterial occlusive disorders and in the coronary arteries of the heart, such as acute coronary syndrome (ACS), myocardial infarction with ST segment elevation (STEMI) and without ST segment elevation (non-STEMI), stable angina pectoris, unstable angina pectoris, reocclusions and restenoses after coronary interventions such as angioplasty, stent implantation or aortocoronary bypass, but also thrombotic or thromboembolic disorders in cerebrovascular arteries, such as transitory ischaemic attacks (TIA), ischemic strokes including cardioembolic strokes, such as strokes due to atrial fibrillation, non-cardioembolic strokes, such as lacunar stroke, strokes due to large or small artery diseases, or strokes due to undetermined cause, cryptogenic strokes, embolic strokes, embolic strokes of undetermined source, or events of thrombotic and/or thromboembolic origin leading to stroke or TIA.

Moreover, the compounds according to the invention are suitable in particular for the treatment and/or prophylaxis of disorders where, the pro-inflammatory component plays an essential role, including vasculitides like Kawasaki disease, Takayasu arteritis and Thrombangiitis obliterans (Buerger's disease) as well as inflammatory disorders like myocarditis.

Furthermore, the compounds according to the invention are suitable for the treatment and/or prophylaxis of disorders of the urogenital tract like overactive bladder, interstitial cystitis and bladder pain syndrome.

Moreover, the compounds according to the invention are suitable for the treatment and/or prophylaxis of diabetes mellitus including its end-organ manifestations like diabetic retinopathy and diabetic nephropathy.

Furthermore, the compounds according to the invention are suitable in particular for the treatment and/or prophylaxis of neurological disorders like neuropathic pain, neurodegenerative disorders and dementias such as vascular dementia or Alzheimer's disease and Parkinson's disease.

Moreover, the compounds according to the invention are suitable in particular for the treatment and/or prophylaxis of pulmonologic disorders like chronic cough, asthma and COPD.

The present invention further provides for the use of the compounds according to the invention for the treatment and/or prophylaxis of disorders, especially the disorders mentioned above.

The present invention further provides for the use of the compounds according to the invention for production of a medicament for the treatment and/or prophylaxis of disorders, especially the disorders mentioned above.

The present invention further provides a method for the treatment and/or prophylaxis of disorders, especially the disorders mentioned above, using a therapeutically effective amount of a compound according to the invention.

The present invention further provides the compounds according to the invention for use in a method for the treatment and/or prophylaxis of disorders, especially the disorders mentioned above, using a therapeutically effective amount of a compound according to the invention.

Particularly the present invention provides the compounds according to the invention for use in a method for the treatment and/or prophylaxis of thrombotic or thromboembolic, in particular atherothrombotic disorders using a therapeutically effective amount of a compound according to the invention.

The present invention further provides medicaments comprising a compound according to the invention and one or more further active compounds.

In addition, the compounds according to the invention can also be used for preventing coagulation ex vivo, for example for the protection of organs to be transplanted against organ damage caused by formation of clots and for protecting the organ recipient against thromboemboli from the transplanted organ, for preserving blood and plasma products, for cleaning/pretreating catheters and other medical auxiliaries and instruments, for coating synthetic surfaces of medical auxiliaries and instruments used in vivo or ex vivo or for biological samples which may comprise factor XIa or plasma kallikrein.

The present invention furthermore provides a method for preventing the coagulation of blood in vitro, in particular in banked blood or biological samples which may comprise factor XIa or plasma kallikrein or both enzymes, which method is characterized in that an anticoagulatory effective amount of the compound according to the invention is added.

The compounds of the invention can act systemically and/or locally. For this purpose, they can be administered in a suitable manner, for example by the oral, parenteral, pulmonal, nasal, sublingual, lingual, buccal, rectal, dermal, transdermal, conjunctival or otic route, or as an implant or stent.

For these administration routes, it is possible for the compounds according to the invention to be administered in suitable administration forms.

For oral administration, it is possible to formulate the compounds according to the invention to dosage forms known in the art that deliver the compounds of the invention rapidly and/or in a modified manner, such as, for example, tablets (uncoated or coated tablets, for example with enteric or controlled release coatings that dissolve with a delay or are insoluble), orally-disintegrating tablets, films/wafers, films/lyophylisates, capsules (for example hard or soft gelatine capsules), sugar-coated tablets, granules, pellets, powders, emulsions, suspensions, aerosols or solutions. It is possible to incorporate the compounds according to the invention in crystalline and/or amorphised and/or dissolved form into said dosage forms.

Parenteral administration can be effected with avoidance of an absorption step (for example intravenous, intraarterial, intracardial, intraspinal or intralumbal) or with inclusion of absorption (for example intramuscular, subcutaneous, intracutaneous, percutaneous or intraperitoneal). Administration forms which are suitable for parenteral administration are, inter alia, preparations for injection and infusion in the form of solutions, suspensions, emulsions, lyophylisates or sterile powders.

Suitable for extraocular (topic) administration are administration forms which operate in accordance with the prior art, which release the active compound rapidly and/or in a modified or controlled manner and which contain the active compound in crystalline and/or amorphized and/or dissolved form such as, for example, eye drops, sprays and lotions (e.g. solutions, suspensions, vesicular/colloidal systems, emulsions, aerosols), powders for eye drops, sprays and lotions (e.g. ground active compound, mixtures, lyophilisates, precipitated active compound), semisolid eye preparations (e.g. hydrogels, in-situ hydrogels, creams and ointments), eye inserts (solid and semisolid preparations, e.g. bioadhesives, films/wafers, tablets, contact lenses).

Intraocular administration includes, for example, intravitreal, subretinal, subscleral, intrachoroidal, subconjunctival, retrobulbar and subtenon administration. Suitable for intraocular administration are administration forms which operate in accordance with the prior art, which release the active compound rapidly and/or in a modified or controlled manner and which contain the active compound in crystalline and/or amorphized and/or dissolved form such as, for example, preparations for injection and concentrates for preparations for injection (e.g. solutions, suspensions, vesicular/colloidal systems, emulsions), powders for preparations for injection (e.g. ground active compound, mixtures, lyophilisates, precipitated active compound), gels for preparations for injection (semisolid preparations, e.g. hydrogels, in-situ hydrogels) and implants (solid preparations, e.g. biodegradable and nonbiodegradable implants, implantable pumps).

Preference is given to oral administration.

Examples which are suitable for other administration routes are pharmaceutical forms for inhalation [inter alia powder inhalers, nebulizers], nasal drops, nasal solutions, nasal sprays; tablets/films/wafers/capsules for lingual, sublingual or buccal administration; suppositories; eye drops, eye ointments, eye baths, ocular inserts, ear drops, ear sprays, ear powders, ear-rinses, ear tampons; vaginal capsules, aqueous suspensions (lotions, mixturae agitandae), lipophilic suspensions, emulsions, ointments, creams, transdermal therapeutic systems (such as, for example, patches), milk, pastes, foams, dusting powders, implants or stents.

The compounds according to the invention can be incorporated into the stated administration forms. This can be effected in a manner known per se by mixing with pharmaceutically suitable excipients.

Pharmaceutically suitable excipients include, inter alia,

- fillers and carriers (for example cellulose, microcrystalline cellulose (such as, for example, Avicel®), lactose, mannitol, starch, calcium phosphate (such as, for example, Di-Cafos®)),
- ointment bases (for example petroleum jelly, paraffins, triglycerides, waxes, wool wax, wool wax alcohols, lanolin, hydrophilic ointment, polyethylene glycols),
- bases for suppositories (for example polyethylene glycols, cacao butter, hard fat),
- solvents (for example water, ethanol, isopropanol, glycerol, propylene glycol, medium chain-length triglycerides fatty oils, liquid polyethylene glycols, paraffins),
- surfactants, emulsifiers, dispersants or wetters (for example sodium dodecyl sulfate), lecithin, phospholipids, fatty alcohols (such as, for example, Lanette®), sorbitan fatty acid esters (such as, for example, Span®), polyoxyethylene sorbitan fatty acid esters (such as, for example, Tween®), polyoxyethylene fatty acid glycerides (such as, for example, Cremophor®), polyoxethylene fatty acid esters, polyoxyethylene fatty alcohol ethers, glycerol fatty acid esters, poloxamers (such as, for example, Pluronic®),
- buffers, acids and bases (for example phosphates, carbonates, citric acid, acetic acid, hydrochloric acid, sodium hydroxide solution, ammonium carbonate, trometamol, triethanolamine),
- isotonicity agents (for example glucose, sodium chloride),
- adsorbents (for example highly-disperse silicas),
- viscosity-increasing agents, gel formers, thickeners and/or binders (for example polyvinylpyrrolidone, methylcellulose, hydroxypropylmethylcellulose, hydroxypropylcellulose, carboxymethylcellulose-sodium, starch, carbomers, polyacrylic acids (such as, for example, Carbopol®); alginates, gelatine), disintegrants (for example modified starch, carboxymethylcellulose-sodium, sodium starch glycolate (such as, for example, Explotab®), cross-linked polyvinylpyrrolidone, croscarmellose-sodium (such as, for example, AcDiSol®)), flow regulators, lubricants, glidants and mould release agents (for example magnesium stearate, stearic acid, talc, highly-disperse silicas (such as, for example, Aerosil®)), coating materials (for example sugar, shellac) and film formers for films or diffusion membranes which dissolve rapidly or in a modified manner (for example polyvinylpyrrolidones (such as, for example, Kollidon®), polyvinyl alcohol, hydroxypropylnethylcellulose, hydroxypropylcellulose, ethylcellulose, hydroxypropylmethylcellulose phthalate, cellulose acetate, cellulose acetate phthalate, polyacrylates, polymethacrylates such as, for example, Eudragit®)), capsule materials (for example gelatine, hydroxypropylnethylcellulose), synthetic polymers (for example polylactides, polyglycolides, polyacrylates, polymethacrylates (such as, for example, Eudragit®), polyvinylpyrrolidones (such as, for example, Kollidon®), polyvinyl alcohols, polyvinyl acetates, polyethylene oxides, polyethylene glycols and their copolymers and blockcopolymers), plasticizers (for example polyethylene glycols, propylene glycol, glycerol, triacetine, triacetyl citrate, dibutyl phthalate), penetration enhancers, stabilisers (for example antioxidants such as, for example, ascorbic acid, ascorbyl palmitate, sodium ascorbate, butylhydroxyanisole, butylhydroxytoluene, propyl gallate), preservatives (for example parabens, sorbic acid, thiomersal, benzalkonium chloride, chlorhexidine acetate, sodium benzoate), colourants (for example inorganic pigments such as, for example, iron oxides, titanium dioxide), flavourings, sweeteners, flavour- and/or odour-masking agents.

The present invention furthermore relates to a pharmaceutical composition which comprises at least one compound according to the invention, conventionally together with one or more pharmaceutically suitable excipient(s), and to their use according to the present invention.

An embodiment of the invention are pharmaceutical compositions comprising at least one compound of formula (I) according to the invention, preferably together with at least one inert, non-toxic, pharmaceutically suitable auxiliary, and the use of these pharmaceutical compositions for the above cited purposes.

In accordance with another aspect, the present invention covers pharmaceutical combinations, in particular medicaments, comprising at least one compound of general formula (I) of the present invention and at least one or more further active ingredients, in particular for the treatment and/or prophylaxis of cardiovascular disorders, preferably thrombotic or thromboembolic disorders, and diabetes, and also urogenital and ophthalmic disorders.

The term "combination" in the present invention is used as known to persons skilled in the art, it being possible for said combination to be a fixed combination, a non-fixed combination or a kit-of-parts.

A "fixed combination" in the present invention is used as known to persons skilled in the art and is defined as a combination wherein, for example, a first active ingredient, such as one or more compounds of general formula (I) of the present invention, and a further active ingredient are present together in one unit dosage or in one single entity. One example of a "fixed combination" is a pharmaceutical composition wherein a first active ingredient and a further active ingredient are present in admixture for simultaneous administration, such as in a formulation. Another example of a "fixed combination" is a pharmaceutical combination wherein a first active ingredient and a further active ingredient are present in one unit without being in admixture.

A non-fixed combination or "kit-of-parts" in the present invention is used as known to persons skilled in the art and is defined as a combination wherein a first active ingredient and a further active ingredient are present in more than one unit. One example of a non-fixed combination or kit-of-parts is a combination wherein the first active ingredient and the further active ingredient are present separately. It is possible for the components of the non-fixed combination or kit-of-parts to be administered separately, sequentially, simultaneously, concurrently or chronologically staggered.

The inventive compounds can be employed alone or, if required, in combination with other active ingredients. The present invention further provides medicaments comprising at least one of the inventive compounds and one or more further active ingredients, especially for treatment and/or prophylaxis of the aforementioned disorders. Preferred examples of suitable active ingredient combinations include:

organic nitrates and NO donors, for example sodium nitroprusside, nitroglycerin, isosorbide mononitrate, isosorbide dinitrate, molsidomine or SIN-1, and inhaled NO;

compounds which inhibit the breakdown of cyclic guanosine monophosphate (cGMP), for example inhibitors of phosphodiesterases (PDE) 1, 2, 5 and/or 9, especially PDE 5 inhibitors such as sildenafil, vardenafil, tadalafil, udenafil, desantafil, avanafil, mirodenafil, lodenafil or PF-00489791;

compounds which inhibit the breakdown of cyclic adenosine monophosphate (cAMP), for example inhibitors of phosphodiesterases (PDE) 3 and 4, especially cilostatzole, milrinone, roflumilast, apremilast, or crisaborole;

hypotensive active ingredients, by way of example and with preference from the group of the calcium antagonists, angiotensin AII antagonists, ACE inhibitors, NEP-inhibitors, vasopeptidase-inhibitors, endothelin antagonists, renin inhibitors, alpha-receptor blockers, beta-receptor blockers, mineralocorticoid receptor antagonists, rho-kinase-inhibitors and the diuretics;

antiarrhythmic agents, by way of example and with preference from the group of sodium channel blocker, beta-receptor blocker, potassium channel blocker, calcium antagonists, If-channel blocker, *digitalis*, parasympatholytics (vagoliytics), sympathomimetics and other antiarrhythmics as adenosin, adenosine receptor agonists as well as vernakalant;

positive-inotrop agents, by way of example cardiac glycoside (Dogoxin), beta-adrenergic and dopaminergic agonists, such as isoprenalin, adrenalin, noradrenalin, dopamin or dobutamin;

vasopressin-receptor-antagonists, by way of example and with preference from the group of conivaptan, tolvaptan, lixivaptan, mozavaptan, satavaptan, pecavaptan, SR-121463, RWJ 676070 or BAY 86-8050, as well as the compounds described in WO 2010/105770, WO2011/104322 and WO 2016/071212;

active ingredients which alter lipid metabolism, for example and with preference from the group of the thyroid receptor agonists, cholesterol synthesis inhibitors such as, by way of example and preferably, HMG-CoA reductase inhibitors or squalene synthesis inhibitors, of ACAT inhibitors, CETP inhibitors, MTP inhibitors, PPAR-alpha, PPAR-gamma and/or PPAR-delta agonists, cholesterol absorption inhibitors, lipase inhibitors, polymeric bile acid adsorbents, bile acid reabsorption inhibitors and lipoprotein(a) antagonists.

bronchodilatory agents, for example and with preference from the group of the beta-adrenergic receptor-agonists, such as, by way of example and preferably, albuterol, isoproterenol, metaproterenol, terbutalin, formoterol or salmeterol, or from the group of the anticholinergics, such as, by way of example and preferably, ipratropiumbromid;

anti-inflammatory agents, for example and with preference from the group of the glucocorticoids, such as, by way of example and preferably, prednison, prednisolon, methylprednisolon, triamcinolon, dexamethason, beclomethason, betamethason, flunisolid, budesonid or fluticason as well as the non-steroidal anti-inflammatory agents (NSAIDs), by way of example and preferably, acetyl salicylic acid (aspirin), ibuprofen and naproxen, 5-amino salicylic acid-derivates, leukotriene-antagonists, TNF-alpha-inhibitors and chemokin-receptor antagonists, such as CCR1, 2 and/or 5 inhibitors;

agents modulating the immune system, for example immunoglobulins;

agents that inhibit the signal transductions cascade, for example and with preference from the group of the kinase inhibitors, by way of example and preferably, from the group of the tyrosine kinase- and/or serine/threonine kinase inhibitors;

agents, that inhibit the degradation and modification of the extracellular matrix, for example and with preference from the group of the inhibitors of the matrix-metalloproteases (MMPs), by way of example and preferably, inhibitors of chymasee, stromelysine, collagenases, gelatinases and aggrecanases (with preference from the group of MMP-1, MMP-3, MMP-8, MMP-9, MMP-10, MMP-11 and MMP-13) as well as of the metallo-elastase (MMP-12) and neutrophil-elastase (HNE), as for example sivelestat or DX-890;

agents, that block the bindung of serotonin to its receptor, for example and with preference antagonists of the 5-HT2b-receptor;

organic nitrates and NO-donators, for example and with preference sodium nitroprussid, nitro-glycerine, isosorbid mononitrate, isosorbid dinitrate, molsidomine or SIN-1, as well as inhaled NO;

NO-independent, but heme-dependent stimulators of the soluble guanylate cyclase, for example and with preference the compounds described in WO 00/06568, WO 00/06569, WO 02/42301, WO 03/095451, WO 2011/147809, WO 2012/004258, WO 2012/028647 and WO 2012/059549;

NO-independent and heme-independent activators of the soluble guanylate cyclase, for example and with preference the compounds described in WO 01/19355, WO 01/19776, WO 01/19778, WO 01/19780, WO 02/070462 and WO 02/070510 beschriebenen Verbindungen;

agents, that stimulates the synthesis of cGMP, like for example sGC modulators, for example and with preference riociguat, cinaciguat, vericiguat or runcaciguat;

prostacyclin-analogs, for example and with preference iloprost, beraprost, treprostinil or epoprostenol;

agents, that inhibit soluble epoxidhydrolase (sEH), for example and with preference N,N'-Di-cyclohexyl urea, 12-(3-Adamantan-1-yl-ureido)-dodecanic acid or 1-Adamantan-1-yl-3-{5-[2-(2-ethoxyethoxy)ethoxy]pentyl}-urea;

agents that interact with glucose metabolism, for example and with preference insuline, biguanide, thiazolidinedione, sulfonyl urea, acarbose, DPP4 inhibitors, GLP-1 analogs or SGLT-2 inhibitors, for example empagliflozin, dapagliflozin, canagliflozin, sotagliflozin;

natriuretic peptides, for example and with preference atrial natriuretic peptide (ANP), natriuretic peptide type B (BNP, Nesiritid) natriuretic peptide type C (CNP) or urodilatin;

activators of the cardiac myosin, for example and with preference omecamtiv mecarbil (CK-1827452);

calcium-sensitizers, for example and with preference levosimendan;

agents that affect the energy metabolism of the heart, for example and with preference etomoxir, dichloroacetat, ranolazine or trimetazidine, full or partial adenosine A1 receptor agonists such as GS-9667 (formerly known as CVT-3619), capadenoson, neladenoson and neladenoson bialanate;

agents that affect the heart rate, for example and with preference ivabradin;

cyclooxygenase inhibitors such as, for example, bromfenac and nepafenac;

inhibitors of the kallikrein-kinin system such as, for example, safotibant and ecallantide;

inhibitors of the sphingosine 1-phosphate signal paths such as, for example, sonepcizumab;

inhibitors of the complement-C5a receptor such as, for example, eculizumab;

plasminogen activators (thrombolytics/fibrinolytics) and compounds which promote thrombolysis/fibrinolysis such as inhibitors of the plasminogen activator inhibitor (PAI inhibitors) or inhibitors of the thrombin-activated fibrinolysis inhibitor (TAFI inhibitors) such as, for example, tissue plasminogen activator (t-PA, for example Actilyse®), streptokinase, reteplase and urokinase or plasminogen-modulating substances causing increased formation of plasmin;

anticoagulatory substances (anticoagulants) such as, for example, heparin (UFH), low-molecular-weight heparins (LMW), for example tinzaparin, certoparin, parnaparin, nadroparin, ardeparin, enoxaparin, reviparin, dalteparin, danaparoid, semuloparin (AVE 5026), adomiparin (M118) and EP-42675/ORG42675;

direct thrombin inhibitors (DTI) such as, for example, Pradaxa (dabigatran), atecegatran (AZD-0837), DP-4088, SSR-182289A, argatroban, bivalirudin and tanogitran (BIBT-986 and prodrug BIBT-1011) and hirudin;

direct factor Xa inhibitors such as, for example, rivaroxaban, apixaban, edoxaban (DU-176b), betrixaban (PRT-54021), R-1663, darexaban (YM-150), otamixaban (FXV-673/RPR-130673), letaxaban (TAK-442), razaxaban (DPC-906), DX-9065a, LY-517717, tanogitran (BIBT-986, prodrug: BIBT-1011), idraparinux and fondaparinux;

inhibitors of coagulation factor XI and XIa such as, for example, FXI ASO-LICA, fesomersen, BAY 121-3790, MAA868, BMS986177, EP-7041 and AB-022;

substances which inhibit the aggregation of platelets (platelet aggregation inhibitors, thrombocyte aggregation inhibitors), such as, for example, acetylsalicylic acid (such as, for example, aspirin), P2Y12 antagonists such as, for example, ticlopidine (Ticlid), clopidogrel (Plavix), prasugrel, ticagrelor, cangrelor and elinogrel, and PAR-1 antagonists such as, for example, vorapaxar, and PAR-4 antagonists;

platelet adhesion inhibitors such as GPVI and/or GPIb antagonists such as, for example, Revacept or caplacizumab;

fibrinogen receptor antagonists (glycoprotein-IIb/IIIa antagonists) such as, for example, abciximab, eptifibatide, tirofiban, lamifiban, lefradafiban and fradafiban;

recombinant human activated protein C such as, for example, Xigris or recombinant thrombomodulin.

Antithrombotic agents are preferably understood to mean compounds from the group of the platelet aggregation inhibitors, the anticoagulants or the profibrinolytic substances.

In a preferred embodiment of the invention, the inventive compounds are administered in combination with a platelet aggregation inhibitor, by way of example and with preference aspirin, clopidogrel, prasugrel, ticagrelor, ticlopidin or dipyridamole.

In a preferred embodiment of the invention, the inventive compounds are administered in combination with a thrombin inhibitor, by way of example and with preference ximelagatran, dabigatran, melagatran, bivalirudin or clexane.

In a preferred embodiment of the invention, the inventive compounds are administered in combination with a GPIIb/IIIa antagonist such as, by way of example and with preference, tirofiban or abciximab.

In a preferred embodiment of the invention, the inventive compounds are administered in combination with a factor Xa inhibitor, by way of example and with preference rivaroxaban (BAY 59-7939), DU-176b, apixaban, betrixaban, otamixaban, fidexaban, razaxaban, letaxaban, eribaxaban, fondaparinux, idraparinux, PMD-3112, darexaban (YM-150), KFA-1982, EMD-503982, MCM-17, MLN-1021, DX 9065a, DPC 906, JTV 803, SSR-126512 or SSR-128428.

In a preferred embodiment of the invention, the inventive compounds are administered in combination with a factor XI or factor XIa inhibitor, by way of example and with preference FXI ASO-LICA, fesomersen, BAY 121-3790, MAA868, BMS986177, EP-7041 or AB-022.

In a preferred embodiment of the invention, the inventive compounds are administered in combination with heparin or with a low molecular weight (LMW) heparin derivative.

In a preferred embodiment of the invention, the inventive compounds are administered in combination with a vitamin K antagonist, by way of example and with preference coumarin.

Hypotensive agents are preferably understood to mean compounds from the group of the calcium antagonists, angiotensin AII antagonists, ACE inhibitors, endothelin antagonists, renin inhibitors, alpha-receptor blockers, beta-receptor blockers, mineralocorticoid receptor antagonists, rho-kinase inhibitors and the diuretics.

In a preferred embodiment of the invention, the inventive compounds are administered in combination with a calcium antagonist, by way of example and with preference nifedipine, amlodipine, verapamil or diltiazem.

In a preferred embodiment of the invention, the inventive compounds are administered in combination with an alpha-1-receptor blocker, by way of example and with preference prazosin.

In a preferred embodiment of the invention, the inventive compounds are administered in combination with a beta-receptor blocker, by way of example and with preference propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the inventive compounds are administered in combination with an angiotensin AII antagonist, by way of example and with preference losartan, candesartan, valsartan, telmisartan or embusartan or a dual angiotensin AII antagonist/neprilysin-inhibitor, by way of example and with preference LCZ696 (valsartan/sacubitril).

In a preferred embodiment of the invention, the inventive compounds are administered in combination with an ACE inhibitor, by way of example and with preference enalapril, captopril, lisinopril, ramipril, delapril, fosinopril, quinopril, perindopril or trandopril.

In a preferred embodiment of the invention, the inventive compounds are administered in combination with an endothelin antagonist, by way of example and with preference bosentan, darusentan, ambrisentan or sitaxsentan.

In a preferred embodiment of the invention, the inventive compounds are administered in combination with a renin inhibitor, by way of example and with preference aliskiren, SPP-600 or SPP-800.

In a preferred embodiment of the invention, the inventive compounds are administered in combination with a mineralocorticoid receptor antagonist, by way of example and with preference spironolactone, AZD9977, finerenone or eplerenone.

In a preferred embodiment of the invention, the inventive compounds are administered in combination with a loop diuretic, for example furosemide, torasemide, bumetanide and piretanide, with potassium-sparing diuretics, for example amiloride and triamterene, with aldosterone antagonists, for example spironolactone, potassium canrenoate and eplerenone, and also thiazide diuretics, for example hydrochlorothiazide, chlorthalidone, xipamide and indapamide.

Lipid metabolism modifiers are preferably understood to mean compounds from the group of the CETP inhibitors, thyroid receptor agonists, cholesterol synthesis inhibitors such as HMG-CoA reductase inhibitors or squalene synthesis inhibitors, the ACAT inhibitors, MTP inhibitors, PPAR-alpha, PPAR-gamma and/or PPAR-delta agonists, cholesterol absorption inhibitors, polymeric bile acid adsorbents, bile acid reabsorption inhibitors, lipase inhibitors and the lipoprotein(a) antagonists.

In a preferred embodiment of the invention, the inventive compounds are administered in combination with a CETP inhibitor, by way of example and with preference dalcetrapib, anacetrapib, torcetrapib (CP-529 414), JJT-705 or CETP vaccine (Avant).

In a preferred embodiment of the invention, the inventive compounds are administered in combination with a thyroid receptor agonist, by way of example and with preference D-thyroxine, 3,5,3'-triiodothyronine (T3), CGS 23425 or axitirome (CGS 26214).

In a preferred embodiment of the invention, the inventive compounds are administered in combination with an HMG- CoA reductase inhibitor from the class of statins, by way of example and with preference lovastatin, simvastatin, pravastatin, fluvastatin, atorvastatin, rosuvastatin or pitavastatin.

In a preferred embodiment of the invention, the inventive compounds are administered in combination with a squalene synthesis inhibitor, by way of example and with preference BMS-188494 or TAK-475.

In a preferred embodiment of the invention, the inventive compounds are administered in combination with an ACAT inhibitor, by way of example and with preference avasimibe, melinamide, pactimibe, eflucimibe or SMP-797.

In a preferred embodiment of the invention, the inventive compounds are administered in combination with an MTP inhibitor, by way of example and with preference implitapide, BMS-201038, R-103757 or JTT-130.

In a preferred embodiment of the invention, the inventive compounds are administered in combination with a PPAR-gamma agonist, by way of example and with preference pioglitazone or rosiglitazone.

In a preferred embodiment of the invention, the inventive compounds are administered in combination with a PPAR-delta agonist, by way of example and with preference GW 501516 or BAY 68-5042.

In a preferred embodiment of the invention, the inventive compounds are administered in combination with a cholesterol absorption inhibitor, by way of example and with preference ezetimibe, tiqueside or pamaqueside.

In a preferred embodiment of the invention, the inventive compounds are administered in combination with a lipase inhibitor, a preferred example being orlistat.

In a preferred embodiment of the invention, the inventive compounds are administered in combination with a polymeric bile acid adsorbent, by way of example and with preference cholestyramine, colestipol, colesolvam, CholestaGel or colestimide.

In a preferred embodiment of the invention, the inventive compounds are administered in combination with a bile acid reabsorption inhibitor, by way of example and with preference ASBT (=IBAT) inhibitors, for example AZD-7806, S-8921, AK-105, BARI-1741, SC-435 or SC-635.

In a preferred embodiment of the invention, the inventive compounds are administered in combination with a lipoprotein(a) antagonist, by way of example and with preference, gemcabene calcium (CI-1027) or nicotinic acid.

In a preferred embodiment of the invention, the inventive compounds are administered in combination with a lipoprotein(a) antagonist, by way of example and with preference, gemcabene calcium (CI-1027) or nicotinic acid.

In a preferred embodiment of the invention, the inventive compounds are administered in combination with sGC modulators, by way of example and with preference, riociguat, cinaciguat or vericiguat.

In a preferred embodiment of the invention, the inventive compounds are administered in combination with an agent affecting the glucose metabolism, by way of example and with preference, insuline, a sulfonyl urea, acarbose, DPP4 inhibitors, GLP-1 analogs or SGLT-1 inhibitors empagliflozin, dapagliflozin, kanagliflozin, sotagliflozin.

In a preferred embodiment of the invention, the compounds according to the invention are administered in combination with a TGFbeta antagonist, by way of example and with preference pirfenidone or fresolimumab.

In a preferred embodiment of the invention, the compounds according to the invention are administered in combination with a CCR2 antagonist, by way of example and with preference CCX-140.

In a preferred embodiment of the invention, the compounds according to the invention are administered in combination with a TNFalpha antagonist, by way of example and with preference adalimumab.

In a preferred embodiment of the invention, the compounds according to the invention are administered in combination with a galectin-3 inhibitor, by way of example and with preference GCS-100.

In a preferred embodiment of the invention, the compounds according to the invention are administered in combination with a Nrf-2 inhibitor, by way of example and with preference bardoxolone In a preferred embodiment of the invention, the compounds according to the invention are administered in combination with a BMP-7 agonist, by way of example and with preference THR-184.

In a preferred embodiment of the invention, the compounds according to the invention are administered in combination with a NOX1/4 inhibitor, by way of example and with preference GKT-137831.

In a preferred embodiment of the invention, the compounds according to the invention are administered in combination with a medicament which affects the vitamin D metabolism, by way of example and with preference calcitriol, alfacalcidol, doxercalciferol, maxacalcitol, paricalcitol, cholecalciferol or paracalcitol.

In a preferred embodiment of the invention, the compounds according to the invention are administered in combination with a cytostatic agent, by way of example and with preference cyclophosphamide.

In a preferred embodiment of the invention, the compounds according to the invention are administered in combination with an immunosuppressive agent, by way of example and with preference ciclosporin.

In a preferred embodiment of the invention, the compounds according to the invention are administered in combination with a phosphate binder, by way of example and with preference colestilan, sevelamer hydrochloride and sevelamer carbonate, Lanthanum and lanthanum carbonate.

In a preferred embodiment of the invention, the compounds according to the invention are administered in combination with renal proximal tubule sodium-phosphate cotransporter, by way of example and with preference, niacin or nicotinamide.

In a preferred embodiment of the invention, the compounds according to the invention are administered in combination with a calcimimetic for therapy of hyperparathyroidism.

In a preferred embodiment of the invention, the compounds according to the invention are administered in combination with agents for iron deficit therapy, by way of example and with preference iron products.

In a preferred embodiment of the invention, the compounds according to the invention are administered in combination with agents for the therapy of hyperurikaemia, by way of example and with preference allopurinol or rasburicase.

In a preferred embodiment of the invention, the compounds according to the invention are administered in combination with glycoprotein hormone for the therapy of anaemia, by way of example and with preference erythropoietin, daprodustat, molidustat, roxadustat, vadadustat, desidustat.

In a preferred embodiment of the invention, the compounds according to the invention are administered in combination with biologics for immune therapy, by way of example and with preference abatacept, rituximab, eculizumab or belimumab.

In a preferred embodiment of the invention, the compounds according to the invention are administered in combination with vasopressin antagonists (group of the vaptanes) for the treatment of heart failure, by way of example and with preference tolvaptan, conivaptan, lixivaptan, mozavaptan, satavaptan, pecavaptan or relcovaptan.

In a preferred embodiment of the invention, the compounds according to the invention are administered in combination with Jak inhibitors, by way of example and with preference ruxolitinib, tofacitinib, baricitinib, CYT387, GSK2586184, lestaurtinib, pacritinib (SB1518) or TG101348.

In a preferred embodiment of the invention, the compounds according to the invention are administered in combination with prostacyclin analogs for therapy of microthrombi.

In a preferred embodiment of the invention, the compounds according to the invention are administered in combination with an alkali therapy, by way of example and with preference sodium bicarbonate.

In a preferred embodiment of the invention, the compounds according to the invention are administered in combination with an mTOR inhibitor, by way of example and with preference everolimus or rapamycin.

In a preferred embodiment of the invention, the compounds according to the invention are administered in combination with an NHE3 inhibitor, by way of example and with preference AZD1722 or tenapanor.

In a preferred embodiment of the invention, the compounds according to the invention are administered in combination with an eNOS modulator, by way of example and with preference sapropterin.

In a preferred embodiment of the invention, the compounds according to the invention are administered in combination with a CTGF inhibitor, by way of example and with preference FG-3019.

The present invention further provides medicaments which comprise at least one compound according to the invention, typically together with one or more inert, nontoxic, pharmaceutically suitable auxiliaries, and the use thereof for the aforementioned purposes.

The compounds according to the invention may act systemically and/or locally. For this purpose, they can be administered in a suitable manner, for example by the oral, parenteral, pulmonal, nasal, sublingual, lingual, buccal, rectal, dermal, transdermal, conjunctival, otic route, or as an implant or stent.

The compounds according to the invention can be administered in administration forms suitable for these administration routes.

Suitable administration forms for oral administration are those which work according to the prior art, which release the compounds according to the invention rapidly and/or in a modified manner and which contain the compounds according to the invention in crystalline and/or amorphized and/or dissolved form, for example tablets (uncoated or coated tablets, for example with gastric juice-resistant or retarded-dissolution or insoluble coatings which control the release of the compound according to the invention), tablets or films/wafers which disintegrate rapidly in the oral cavity, films/lyophilizates or capsules (for example hard or soft gelatin capsules), sugar-coated tablets, granules, pellets, powders, emulsions, suspensions, aerosols or solutions.

Parenteral administration can bypass an absorption step (e.g. intravenously, intraarterially, intracardially, intraspinally or intralumbally) or include an absorption (e.g. intramuscularly, subcutaneously, intracutaneously, percutaneously or intraperitoneally). Administration forms suitable for parenteral administration include preparations for injection and infusion in the form of solutions, suspensions, emulsions, lyophilizates or sterile powders.

For the other administration routes, suitable examples are inhalable medicament forms (including powder inhalers, nebulizers), nasal drops, solutions or sprays, tablets, films/wafers or capsules for lingual, sublingual or buccal administration, suppositories, ear or eye preparations, vaginal capsules, aqueous suspensions (lotions, shaking mixtures), lipophilic suspensions, ointments, creams, transdermal therapeutic systems (e.g. patches), milk, pastes, foams, sprinkling powders, implants or stents.

Oral or parenteral administration is preferred, especially oral and intravenous administration.

The compounds according to the invention can be converted to the administration forms mentioned. This can be done in a manner known per se, by mixing with inert, nontoxic, pharmaceutically suitable excipients. These excipients include carriers (for example microcrystalline cellulose, lactose, mannitol), solvents (e.g. liquid polyethylene glycols), emulsifiers and dispersing or wetting agents (for example sodium dodecylsulphate, polyoxysorbitan oleate), binders (for example polyvinylpyrrolidone), synthetic and natural polymers (for example albumin), stabilizers (e.g. antioxidants, for example ascorbic acid), dyes (e.g. inorganic pigments, for example iron oxides) and flavour and/or odour correctants.

In general, it has been found to be advantageous in the case of parenteral administration to administer amounts of about 0.001 to 1 mg/kg, preferably about 0.01 to 0.5 mg/kg, of body weight to achieve effective results. In the case of oral administration, the dosage is about 0.01 to 100 mg/kg, preferably about 0.01 to 20 mg/kg and most preferably 0.1 to 10 mg/kg of body weight.

It may nevertheless be necessary where appropriate to deviate from the stated amounts, specifically as a function of the body weight, route of administration, individual response to the active compound, nature of the preparation and time or interval over which administration takes place. For instance, in some cases, less than the aforementioned minimum amount may be sufficient, while in other cases the upper limit mentioned must be exceeded. In the case of administration of relatively large amounts, it may be advisable to divide these into several individual doses over the course of the day.

The total amount of the active ingredient to be administered will generally range from about 0.001 mg/kg to about 200 mg/kg body weight per day, and preferably from about 0.01 mg/kg to about 50 mg/kg body weight per day, and more preferably from about 0.01 mg/kg to about 20 mg/kg body weight per day.

Clinically useful dosing schedules will range from one to three times a day dosing to once every four weeks dosing. In addition, it is possible for "drug holidays", in which a patient is not dosed with a drug for a certain period of time, to be beneficial to the overall balance between pharmacological effect and tolerability. It is possible for a unit dosage to contain from about 0.5 mg to about 1500 mg of active ingredient, and can be administered one or more times per day or less than once a day. The average daily dosage for administration by injection, including intravenous, intramuscular, subcutaneous and parenteral injections, and use of infusion techniques will preferably be from 0.01 to 200 mg/kg of total body weight. The average daily rectal dosage regimen will preferably be from 0.01 to 200 mg/kg of total body weight. The average daily vaginal dosage regimen will preferably be from 0.01 to 200 mg/kg of total body weight. The average daily topical dosage regimen will preferably be from 0.1 to 200 mg administered between one to four times daily. The transdermal concentration will preferably be that required to maintain a daily dose of from 0.01 to 200 mg/kg. The average daily inhalation dosage regimen will preferably be from 0.01 to 100 mg/kg of total body weight.

Of course the specific initial and continuing dosage regimen for each patient will vary according to the nature and severity of the condition as determined by the attending diagnostician, the activity of the specific compound employed, the age and general condition of the patient, time of administration, route of administration, rate of excretion of the drug, drug combinations, and the like. The desired mode of treatment and number of doses of a compound of the present invention or a pharmaceutically acceptable salt or ester or composition thereof can be ascertained by those skilled in the art using conventional treatment tests.

Nevertheless, it may optionally be necessary to deviate from the stated amounts, namely depending on body weight, route of administration, individual response to the active substance, type of preparation and time point or interval when application takes place. Thus, in some cases it may be sufficient to use less than the aforementioned minimum amount, whereas in other cases the stated upper limit must be exceeded. When applying larger amounts, it may be advisable to distribute these in several individual doses throughout the day.

According to a further embodiment, the compounds of formula (I) according to the invention are administered orally once or twice or three times a day. According to a further embodiment, the compounds of formula (I) according to the invention are administered orally once or twice a day.

According to a further embodiment, the compounds of formula (I) according to the invention are administered orally once a day. For the oral administration, a rapid release or a modified release dosage is form may be used.

Unless stated otherwise, the percentages in the tests and examples which follow are percentages by weight; parts are parts by weight. Solvent ratios, dilution ratios and concentration data for the liquid/liquid solutions are based in each case on volume. "w/v" means "weight/volume". For example, "10% w/v" means: 100 ml of solution or suspension comprise 10 g of substance.

EXPERIMENTAL SECTION

TABLE 1

Abbreviations
The following table lists the abbreviations used herein.

| Abbreviation | Meaning |
|---|---|
| $BH_3$•THF | Borane-tetrahydrofuran |
| BINAP | 2,2'-Bis(diphenylphosphino)-1,1'-binaphthyl |
| br | broad ($^1$H-NMR signal) |
| CI | chemical ionisation |
| d | doublet ($^1$H-NMR signal) |
| d | day(s) |
| DAD | diode array detector |
| dd | double-doublet |
| DMF | N,N-dimethylformamide |
| DMSO | dimethylsulfoxide |
| ESI | electrospray (ES) ionisation |
| EtOAc | Ethyl acetate |
| h | hour(s) |
| HATU | 1-[Bis(dimethylamino)methylene]-1H-1,2,3-triazolo[4,5-b]pyridinium 3-oxide hexafluorophosphate, CAS 148893-10-1 |
| HPLC | high performance liquid chromatography |
| LC-MS | liquid chromatography mass spectrometry |
| m | multiplet ($^1$H-NMR signal) |
| M | molar |
| min | minute(s) |
| MS | mass spectrometry |
| MTBE | methyl-tert-butylether |
| $NaBH_4$ | Sodium borohydride, sodium tetrahydroborate |
| $NaHCO_3$ | Sodium hydrogen carbonate |
| $Na_2SO_4$ | Sodium sulphate |
| NMR | nuclear magnetic resonance spectroscopy: chemical shifts (δ) are given in ppm. The chemical shifts were corrected by setting the DMSO signal to 2.50 ppm unless otherwise stated. |
| PDA | Photo Diode Array |
| $Pd_2dba_3$ | Tris(dibenzylideneacetone)dipalladium (0), CAS 51364-51-3 |
| $Pd(PPh_3)_4$ | Tetrakis(triphenylphosphane)palladium(0), CAS 14221-01-3 |
| quant. | quantitative |
| rac | racemic |
| $R_t$, Rt | retention time (as measured either with HPLC or UPLC) in minutes |
| RuPhos Pd G3 | (2-Dicyclohexylphosphino-2',6'-diisopropoxy-1,1'-biphenyl)[2-(2'-amino-1,1'-biphenyl)]palladium(II) methanesulfonate, CAS 1445085-77-7 |
| s | singlet ($^1$H-NMR signal) |
| SFC | Supercritical Fluid Chromatography |
| SQD | Single-Quadrupole-Detector |
| t | triplet ($^1$H-NMR signal) |
| td | triple-doublet ($^1$H-NMR signal) |
| TFA | trifluoroacetic acid |
| THF | tetrahydrofuran |
| UPLC | ultra performance liquid chromatography |
| X-Phos | 2-Dicyclohexylphosphino-2',4',6'-triisopropylbiphenyl, CAS 564483-18-7 |

Other abbreviations not specified herein have their meanings customary to the skilled person.

The various aspects of the invention described in this application are illustrated by the following examples which are not meant to limit the invention in any way. All publications mentioned herein are incorporated by reference in their entirety.

The example testing experiments described herein serve to illustrate the present invention and the invention is not limited to the examples given.

Experimental Section—General Part

All reagents, for which the synthesis is not described in the experimental part, are either commercially available, or are known compounds or may be formed from known compounds by known methods by a person skilled in the art.

The compounds and intermediates produced according to the methods of the invention may require purification. Purification of organic compounds is well known to the person skilled in the art and there may be several ways of purifying the same compound. In some cases, no purification may be necessary. In some cases, the compounds may be purified by crystallization. In some cases, impurities may be stirred out using a suitable solvent. In some cases, the compounds may be purified by chromatography, particularly flash column chromatography, using for example prepacked silica gel cartridges, e.g. Biotage SNAP cartidges KP-Sil® or KP-NH® in combination with a Biotage autopurifier system (SP4® or Isolera Four®) and eluents such as gradients of hexane/ethyl acetate or DCM/methanol. In some cases, the compounds may be purified by preparative HPLC using for example a Waters autopurifier equipped with a diode array detector and/or on-line electrospray ionization mass spectrometer in combination with a suitable prepacked reverse phase column and eluents such as gradients of water and acetonitrile which may contain additives such as trifluoroacetic acid, formic acid or aqueous ammonia.

In some cases, purification methods as described above can provide those compounds of the present invention which possess a sufficiently basic or acidic functionality in the form of a salt, such as, in the case of a compound of the present invention which is sufficiently basic, a trifluoroacetate or formate salt for example, or, in the case of a compound of the present invention which is sufficiently acidic, an ammonium salt for example. A salt of this type can either be transformed into its free base or free acid form, respectively, by various methods known to the person skilled in the art, or be used as salts in subsequent biological assays. It is to be understood that the specific form (e.g. salt, free base etc.) of a compound of the present invention as isolated and as described herein is not necessarily the only form in which said compound can be applied to a biological assay in order to quantify the specific biological activity.

In the case of the synthesis intermediates and working examples of the invention described hereinafter, any compound specified in the form of a salt of the corresponding base or acid is generally a salt of unknown exact stoichiometric composition, as obtained by the respective preparation and/or purification process. Unless specified in more detail, additions to names and structural formulae, such as is "hydrochloride", "trifluoroacetate", "sodium salt" or "x HCl", "x $CF_3COOH$", "x $Na^+$" should not therefore be understood in a stoichiometric sense in the case of such salts, but have merely descriptive character with regard to the salt-forming components present therein.

This applies correspondingly if synthesis intermediates or working examples or salts thereof were obtained in the form of solvates, for example hydrates, of unknown stoichiometric composition (if they are of a defined type) by the preparation and/or purification processes described.

NMR peak forms are stated as they appear in the spectra, possible higher order effects have not been considered.

The $^1$H-NMR data of selected compounds are listed in the form of $^1$H-NMR peaklists. For each signal peak the δ value in ppm is given, followed by the signal intensity, reported in round brackets. The δ value-signal intensity pairs from different peaks are separated by commas. Therefore, a peaklist is described by the general form: $\delta_1$ (intensity$_1$), $\delta_2$ (intensity$_2$), . . . , $\delta_i$ (intensity$_i$), . . . , $\delta_n$ (intensity$_n$).

The intensity of a sharp signal correlates with the height (in cm) of the signal in a printed NMR spectrum.

When compared with other signals, this data can be correlated to the real ratios of the signal intensities.

In the case of broad signals, more than one peak, or the center of the signal along with their relative intensity, compared to the most intense signal displayed in the spectrum, are shown. A $^1$H-NMR peaklist is similar to a classical $^1$H-NMR readout, and thus usually contains all the peaks listed in a classical NMR interpretation. Moreover, similar to classical $^1$H-NMR printouts, peaklists can show solvent signals, signals derived from stereoisomers of target compounds (also the subject of the invention), and/or peaks of impurities. The peaks of stereoisomers, and/or peaks of impurities are typically displayed with a lower intensity compared to the peaks of the target compounds (e.g., with a purity of >90%). Such stereoisomers and/or impurities may be typical for the particular manufacturing process, and therefore their peaks may help to identify the reproduction of our manufacturing process on the basis of "by-product fingerprints". An expert who calculates the peaks of the target compounds by known methods (MestReC, ACD simulation, or by use of empirically evaluated expectation values), can isolate the peaks of target compounds as required, optionally using additional intensity filters. Such an operation would be similar to peak-picking in classical $^1$H-NMR interpretation. A detailed description of the reporting of NMR data in the form of peaklists can be found in the publication "Citation of NMR Peaklist Data within patent applications" (cf. Research Disclosure Database Number 605005, 2014, 1 Aug. 2014, or researchdisclosure.com/searching-disclosures). In the peak picking routine, as described in the Research Disclosure Database Number 605005, the parameter "MinimumHeight" can be adjusted between 1% and 4%. Depending on the chemical structure and/or depending on the concentration of the measured compound it may be reasonable to set the parameter "MinimumHeight"<1%.

In NMR spectra of mixtures of stereoisomers, numbers mentioned with "/" indicate that the stereoisomers show separate signals for the respective hydrogen atom, i.e. " . . . / . . . (2s, 1H)" means that one hydrogen atom is represented by 2 singlets, each singlet from one or more different stereoisomer(s).

IUPAC names of the following intermediates and example compounds were generated using the ACD/Name software (batch version 14.00; Advanced Chemistry Development, Inc.) or the naming tool implemented in the BIOVIA Draw software (version 4.2 SPi; Dassault Systemes SE).

Analytical LC-MS Methods

Method 1

MS instrument type: SHIMADZU LCMS-2020, Column: Kinetex EVO C18 30*2.1 mm, 5 um, mobile phase A: 0.0375% TFA in water (v/v), B: 0.01875% TFA in Acetonitrile (v/v), gradient: 0.0 min 0% B→0.8 min 95% B→1.2 min 95% B→1.21 min 5% B→1.55 min 5% B, flow rate: 1.5 mL/min, oven temperature: 50° C.; UV detection: 220 nm & 254 nm.

Method 2

HPLC instrument type: SHIMADZU LCMS-2020, Column: Kinetex EVO C18 50*4.6 mm, 5 um, mobile phase A: 0.0375% TFA in water (v/v), B: 0.01875% TFA in Acetonitrile (v/v), gradient: 0.0 min 10% B→2.4 min 80% B→3.7 min 80% B→3.71 min 10% B→4.0 min 10% B, flow rate: 1.5 mL/min, oven temperature: 50° C.; UV detection: 220 nm & 215 nm & 254 nm.

Method 3 (LC-MS)

Instrument MS: Thermo Scientific FT-MS; Instrument type UHPLC+: Thermo Scientific UltiMate 3000; Column: Waters, HSST3, 2.1×75 mm, C18 1.8 μm; Eluent A: 1 l water+0.01% formic acid; Eluent B: 1 l Acetonitrile+0.01% formic acid; Gradient: 0.0 min 10% B→2.5 min 95% B→3.5 min 95% B; oven: 50° C.; flow rate: 0.90 ml/min; UV-Detection: 210 nm/Optimum Integration Path 210-300 nm.

Method 4 (LC-MS)

Instrument: Waters ACQUITY SQD UPLC System; Column: Waters Acquity UPLC HSS T3 1.8 μm 50×1 mm;

Eluent A: 1 l water+0.25 ml formic acid, Eluent B: 1l Acetonitrile+0.25 ml formic acid; Gradient: 0.0 min 90% A→1.2 min 5% A→2.0 min 5% A; oven: 50° C.; flow rate: 0.40 ml/min; UV-Detection: 210 n.

Method 5 (LC-MS)

Instrument: Waters ACQUITY SQD UPLC System; Column: Waters Acquity UPLC HSS T3 1.8 μm 50×1 mm; Eluent A: 1 l water+0.25 ml formic acid, Eluent B: 1 l Acetonitrile+0.25 ml formic acid; Gradient: 0.0 min 95% A→6.0 min 5% A→7.5 min 5% A; oven: 50° C.; flow rate: 0.35 ml/min; UV-Detection: 210 n.

Method 6 (LC-MS)

Instrument: Agilent MS Quad 6150; HPLC: Agilent 1290; Column: Waters Acquity UPLC HSS T3 1.8 μm 50×2.1 mm; Eluent A: 1l water+0.25 ml formic acid, Eluent B: 1 l Acetonitrile+0.25 ml formic acid; Gradient: 0.0 min 90% A→0.3 min 90% A→1.7 min 5% A→3.0 min 5% A oven: 50° C.; flow rate: 1.20 ml/min; UV-Detection: 205-305 nm.

Method 7 (LC-MS)

Instrument: Waters Single Quad MS System; Instrument Waters UPLC Acquity; Column: Waters BEH C18 1.7 g 50×2.1 mm; Eluent A: 1 l water+1.0 mL (25% aqueous Ammonia)/L, Eluent B: 1 l Acetonitrile; Gradient: 0.0 min 92% A→0.1 min 92% A→1.8 min 5% A→3.5 min 5% A; oven: 50° C.; flow rate: 0.45 mL/min; UV-Detection: 210 n.

Method 8 (LC-MS)

System MS: Waters TOF instrument; System UPLC: Waters Acquity I-CLASS; Column: Waters Acquity UPLC HSS T3 1.8 μm 50×1 mm; Eluent A: 1l Water+0.100 ml 99% ige Formic acid, Eluent B: 1 l Acetonitrile+0.100 ml 99% ige Formic acid; Gradient: 0.0 min 90% A→1.2 min 5% A→2.0 min 5% A Oven: 50° C.; Flow: 0.40 ml/min; UV-Detection: 210 nm.

Method 9 (LC-MS):

System MS: Waters TOF instrument; System UPLC: Waters Acquity I-CLASS; Column: Waters Acquity UPLC HSS T3 1.8 μm 50×1 mm; Eluent A: 1l Water+0.100 ml 99% ige Formic acid, Eluent B: 1 l Acetonitrile+0.100 ml 99% ige Formic acid; Gradient: 0.0 min 95% A→6.0 min 5% A→7.5 min 5% A Oven: 50° C.; Flow: 0.35 ml/min; UV-Detection: 210 nm.

Preparative HPLC Methods

Instrument: Waters Prep LC/MS System, column: Phenomenex Kinetex C18 5 μm 100×30 mm, UV-detection 200-400 nm, room temperature, At-Column Injection (complete injection), eluent A: water, eluent B: acetonitrile, eluent C: 2% formic acid in water, eluent D: acetonitrile/water (80 vol. %/20 vol. %); flow: 80 ml/min, gradient profile: 0 to 2 min: eluent A 47 ml/min, eluent B 23 ml/min; 2 to 10 min: eluent A from 47 ml/min to 23 ml/min, eluent B from 23 ml/min to 47 ml/min; 10 to 12 min eluent A 0 ml/min and eluent B 70 ml/min; eluent C and eluent D have a constant flow of 5 ml/min each over the whole running time.

Microwave: Reactions employing microwave irradiation may be run with a Biotage Initator® microwave oven optionally equipped with a robotic unit. The reported reaction times employing microwave heating are intended to be understood as fixed reaction times after reaching the indicated reaction temperature.

When compounds according to the invention are purified by preparative HPLC by the above-described methods in which the eluents contain additives, for example trifluoroacetic acid, formic acid or ammonia, the compounds according to the invention may be obtained in salt form, for example as trifluoroacetate, formate or ammonium salt, if the compounds according to the invention contain a sufficiently basic or acidic functionality. Such a salt can be converted to the corresponding free base or acid by various methods known to the person skilled in the art.

In the case of the synthesis intermediates and working examples of the invention described hereinafter, any compound specified in the form of a salt of the corresponding base or acid is generally a salt of unknown exact stoichiometric composition, as obtained by the respective preparation and/or purification process. Unless specified in more detail, additions to names and structural formulae, such as "hydrochloride", "trifluoroacetate", "sodium salt" or "x HCl", "x $CF_3COOH$", "x Na*" should not therefore be understood in a stoichiometric sense in the case of such salts, but have merely descriptive character with regard to the salt-forming components present therein.

This applies correspondingly if synthesis intermediates or working examples or salts thereof were obtained in the form of solvates, for example hydrates, of unknown stoichiometric composition (if they are of a defined type) by the preparation and/or purification processes described.

Enantiomer 1 is an enantiomer which eluted first out of the column.

Enantiomer 2 is an enantiomer which eluted second out of the column.

For example 3 (enantiomer 2) the absolute configuration was determined by single crystal X-ray structure analysis to be R. Consequently all compounds annotated as enantiomer 2 should have an absolute configuration of R. The corresponding stereochemistry should survive all synthetic conditions due to its substitution pattern.

Diastereomeric mixture 1 defines a compound where its starting material is defined as Enantiomer 1 and is reacted with a building block containing at least one chiral center and where the configuration is not defined Diastereomeric mixture 2 defines a compound where its starting material is defined as Enantiomer 2 and is reacted with a building block containing at least one chiral center and where the configuration is not defined Diastereomer 1 and Diastereomer 2 defines the two compounds resulting from the chiral separation of the diastereomeric mixture 1 described above.

Diastereomer 3 and Diastereomer 4 defines the two compounds resulting from the chiral separation of the diastereomeric mixture 2 described above.

Stereoisomer 1 defines a compound where its starting material is defined as Enantiomer 1 and is reacted with a building block containing at least one chiral center and where the configuration is defined.

Stereoisomer 2 defines a compound where its starting material is defined as Enantiomer 2 and is reacted with a building block containing at least one chiral center and where the configuration is defined.

Starting Compounds and Intermediates

Intermediate 1A

Example 1A

Tert-butyl 3-{2-[(benzyloxy)carbonyl] hydrazino}piperidine-1-carboxylate (Racemate)

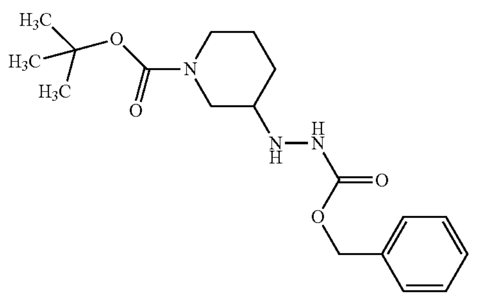 [SMILES: CC(C)(C)OC(=O)N1CCCC(NNC(=O)OCc2ccccc2)C1]

To a solution of tert-butyl 3-oxopiperidine-1-carboxylate [CAS No. 989-36-7] (300 g, 1.51 mol) in tetrahydrofuran (1.50 L) and Methanol (300 mL) was added benzyl hydrazinecarboxylate [CAS No. 5331-43-1] (250 g, 1.51 mol) at 25° C., then, the mixture was stirred at 25° C. for 1 h. Afterwards $NaBH_4$ (114 g, 3.01 mol) was added in portions to the mixture at 25° C. and stirred at 25° C. for 2 h. The reaction mixture was cooled to 10° C., and sat. $NH_4Cl$ was added dropwise to pH~6. The mixture was extracted with EtOAc (300 mL*2) and concentrated in vacuo. The residue was dissolved in MTBE (300 mL) and petroleum ether (300 mL) was added. The mixture was filtrated off and the precipitate was washed with petroleum ether (100 mL) affording the title compound (400 g, 1.14 mol, 76.0% yield) as a white solid.

LC-MS: (Method 1) Rr=0.832 min, MS (M−100+1=250.4).

Example 2A

Tert-butyl 3-hydrazinopiperidine-1-carboxylate acetic acid (Racemate)

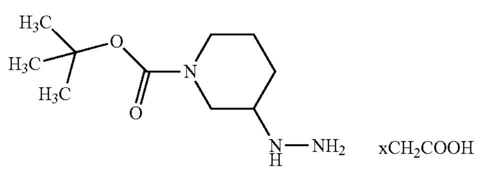

To a solution of tert-butyl 3-{2-[(benzyloxy)carbonyl] hydrazino}piperidine-1-carboxylate (prepared in analogy to Example 1A, 1.20 kg, 3.43 mol) in ethanol (11.0 L) was added acetic acid (415 g, 6.91 mol, 395 mL) and Pd/C (120 g, 20% purity) under $H_2$ (15 Psi). The mixture was stirred at 25° C. for 12 h. The mixture was filtrated and the precipitate was washed with ethanol (11.0 L) to give a solution of the title compound in ethanol (945 g, acetic acid salt) as a black liquid, the filtrate was used for the next step without purification.

$^1$H-NMR (400 MHz, $CDCl_3$) δ [ppm]: 7.52 (s, 5H), 3.59 (d, J=6.0 Hz, 12H), 3.30-3.24 (m, 2H), 2.75-2.71 (m, 2H), 1.38-1.34 (m, 1H), 1.20-1.18 (m, 1H), 1.10 (s, 9H)

LC-MS: (Method 1) Rr=0.263 min, MS (M−56+1=160.2)

Example 3A

Ethyl 2-(ethoxymethylidene)-4,4-difluoro-3-oxobutanoate

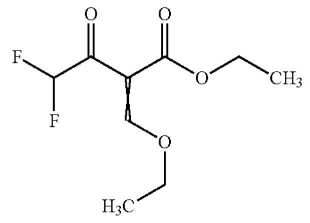

A solution of ethyl 4,4-difluoro-3-oxobutanoate [CAS No. 352-24-9] (120 g, 722 mmol) and (diethoxymethoxy)ethane (240 ml, 1.4 mol) in acetic acid anhydride (200 ml, 2.2 mol) was stirred overnight at 140° C. and evaporated to dryness affording 155 g (quant.) of the title compound which was used in the next step without further purification.

$^1$H-NMR (600 MHz, $CDCl_3$) δ [ppm]: 1.306 (6.05), 1.318 (16.00), 1.330 (14.48), 1.341 (4.56), 1.428 (5.99), 1.436 (5.01), 1.440 (12.20), 1.448 (9.25), 1.451 (6.31), 1.460 (4.48), 2.095 (1.59), 2.225 (1.56), 4.247 (1.97), 4.260 (5.79), 4.271 (5.85), 4.277 (1.55), 4.283 (2.00), 4.289 (4.40), 4.301 (4.37), 4.308 (2.03), 4.313 (1.64), 4.320 (5.74), 4.332 (5.78), 4.340 (1.60), 4.344 (2.01), 4.351 (4.21), 4.364 (4.20), 4.375 (1.37), 6.262 (1.79), 6.339 (1.35), 6.352 (3.56), 6.429 (2.63), 6.442 (1.72), 6.519 (1.28), 7.867 (5.48), 7.880 (7.31).

Example 4A

Tert-butyl 3-[5-(difluoromethyl)-4-(ethoxycarbonyl)-1H-pyrazol-1-yl]piperidine-1-carboxylate (Racemate)

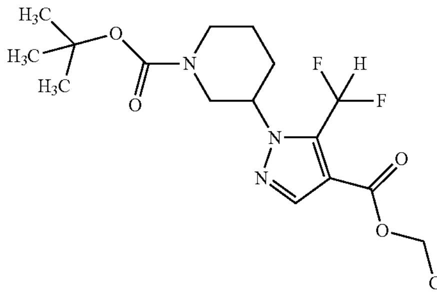

To a mixture of tert-butyl 3-hydrazinopiperidine-1-carboxylate acetic acid (Example 2A, 945 g, 3.43 mol) in ethanol (20.0 L) was added ethyl 2-(ethoxymethylene)-4,4-difluoro-3-oxobutanoate (prepared in analogy to Example 3A, 840 g, 3.78 mol). The mixture was stirred at 25° C. for 12 h. The reaction mixture was concentrated. The residue was poured into saturated $NaHCO_3$ aqueous solution (10.0 L), and extracted with Ethyl acetate (10.0 L*2). The combined organic layer was washed with brine (10.0 L), dried over $Na_2SO_4$, filtered and concentrated. The residue was purified by column chromatography on silica gel eluted with Petroleum ether: Ethyl acetate (50:1-25:1-10:1, $R_f$=0.3) affording 530 g (41.4% yield) of the title compound.

$^{1}$H-NMR (400 MHz, $CDCl_3$) δ [ppm]: 7.84 (s, 1H), 7.51 (t, J=12.8 Hz, 1H), 4.47-4.41 (m, 1H), 4.30-4.10 (m, 4H), 3.19-3.13 (m, 1H), 2.69 (s, 1H), 2.15-2.10 (m, 2H), 1.83-1.78 (m, 1H), 1.60-1.55 (m, 1H), 1.40 (s, 9H), 1.32-1.29 (m, 3H)

LC-MS (Method 1) Rr=0.992 min, MS (M−56+1=318.0).

Example 5A

Ethyl 5-(difluoromethyl)-1-(piperidin-3-yl)-1H-pyrazole-4-carboxylate (Racemate)

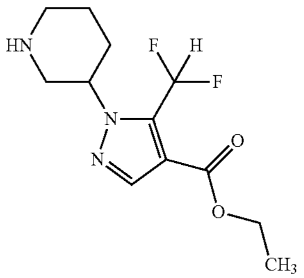 [SMILES: CCOC(=O)c1cnn(C2CCCNC2)c1C(F)F]

Tert-butyl 3-[5-(difluoromethyl)-4-(ethoxycarbonyl)-1H-pyrazol-1-yl]piperidine-1-carboxylate (prepared in analogy to Example 4A, 593 g, 1.59 mol) was added to a solution of hydrogen chloride in dioxane (4 M, 2.50 L), the mixture was stirred at 25° C. for 12 h. The mixture was evaporated and the residue was dissolved in 1.00 L water and extracted with MTBE 500 mL. The aqueous phase was separated and adjusted pH to 8-9 with $NaHCO_3$. The aqueous phase was extracted with dichloromethane (1.00 L×2), and the combined organic phases were washed with brine (1.00 L), dried over $Na_2SO_4$ and concentrated to give 350 g (80.6% yield) of the title compound.

$^{1}$H-NMR (400 MHz, $CDCl_3$) δ [ppm]: 7.87 (s, 1H), 7.54 (t, J=12.8 Hz, 1H), 4.55-4.54 (m, 1H), 4.34-4.28 (m, 2H), 3.25-3.03 (m, 3H), 2.71-2.65 (m, 1H), 2.19-1.86 (m, 4H), 1.63-1.60 (m, 1H), 1.35 (t, J=7.2 Hz, 3H)

LC-MS: (Method 1) Rr=0.644 min, MS (M+1)=274.6

In analogy to Example 5A, ethyl 5-(difluoromethyl)-1-(piperidin-3-yl)-1H-pyrazole-4-carboxylate (Racemate) was prepared using different protecting groups. The two enantiomers were separated by SFC [sample preparation: 20 g were dissolved in 500 ml methanol; injection volume: 15 ml; column: Daicel AZ SCF 20 μm, 400×50 mm; eluent: carbone dioxide/methanol/aqueous ammonia (1%) 80:19:1 to 60:39:1; flow rate: 400 ml/min; temperature: 40° C.; UV detection: 220 nm]. After separation, 8.1 g of enantiomer 1 (Example 6A), which eluted first, and 8.0 g of enantiomer 2 (Example 7A), which eluted later, were isolated.

Example 6A

Ethyl 5-(difluoromethyl)-1-(piperidin-3-yl)-1H-pyrazole-4-carboxylate (Enantiomer 1)

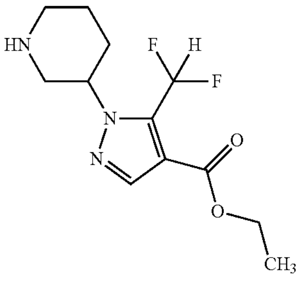 [SMILES: CCOC(=O)c1cnn(C2CCCNC2)c1C(F)F]

For separation conditions see Example 5A.

Analytical SFC: Rr=0.980 min, e.e.=100% [Column Chiralpak IC-3: 50×4.6 mm; eluent: $CO_2$/[methanol+0.2% diethyl amine]: 90:10 flow rate: 3.0 ml/min; temperature: 25° C.; UV detection: 220 nm].

$_{1}$H-NMR (400 MHz, DMSO-d6) δ[ppm]: 8.00 (s, 1H), 7.75-7.44 (m, 1H), 4.50-4.36 (m, 1H), 4.33-4.18 (m, 2H), 3.10-2.95 (m, 1H), 2.91-2.76 (m, 2H), 2.48-2.33 (m, 2H), 2.08-1.94 (m, 2H), 1.81-1.66 (m, 1H), 1.62-1.40 (m, 1H), 1.37-1.21 (m, 3H).

Example 7A

Ethyl 5-(difluoromethyl)-1-(piperidin-3-yl)-1H-pyrazole-4-carboxylate (Enantiomer 2)

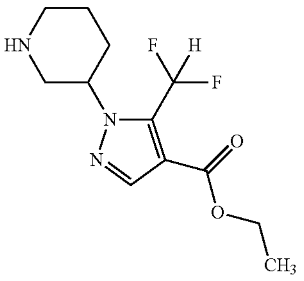 [SMILES: CCOC(=O)c1cnn(C2CCCNC2)c1C(F)F]

For separation conditions see Example 5A.

Analytical SFC: Rr=1.227 min, e.e.=97% [Column Chiralpak IC-3: 50×4.6 mm; eluent: C02/[methanol+0.2% diethyl amine]: 90:10 flow rate: 3.0 ml/min; temperature: 25° C.; UV detection: 220 nm].

$^{1}$H-NMR (400 MHz, DMSO-d6) δ[ppm]: 8.01 (s, 1H), 7.75-7.43 (m, 1H), 4.50-4.37 (m, 1H), 4.27 (q, 2H), 3.09-2.97 (m, 1H), 2.94-2.81 (m, 2H), 2.47-2.34 (m, 2H), 2.06-1.92 (m, 2H), 1.79-1.66 (m, 1H), 1.60-1.41 (m, 1H), 1.29 (t, 3H).

Example 8A

2-Bromo-4-chloro-1-[(4-methoxyphenyl)methoxy]benzene

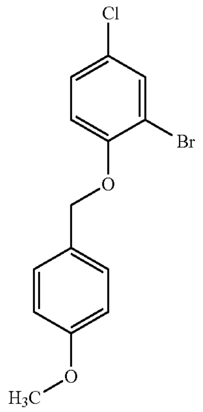 [SMILES: COc1ccc(COc2ccc(Cl)cc2Br)cc1]

A solution of 2-bromo-4-chlorophenol [CAS No. 695-96-5] (10.0 g, 48.2 mmol) in acetone (75 ml) was treated with potassium carbonate (13.3 g, 96.4 mmol) and potassium iodide (12.0 g, 72.3 mmol) and 1-(chloromethyl)-4-methoxybenzene (7.55 g, 48.2 mmol). The resulting mixture was stirred ~19 hours at 70° C. The reaction mixture was diluted with water and extracted twice with ethyl acetate. The combined organic layers were dried over sodium sulphate and evaporated. The residue was purified by flash chromatography (silica gel, cyclohexane/ethyl acetate gradient) affording 13.8 g (86% yield) of the title compound.

LC-MS (Method 3): Rr=2.48 min; MS (ESIneg): m/z=324 $[M-H]^-$ $^1$H-NMR (600 MHz, DMSO-d6) δ[ppm]: 3.349 (10.98), 5.124 (16.00), 6.949 (0.87), 6.954 (8.36), 6.957 (2.68), 6.965 (2.83), 6.968 (8.92), 6.973 (1.00), 7.218 (5.23), 7.233 (6.21), 7.380 (0.90), 7.384 (7.80), 7.399 (7.44), 7.402 (4.47), 7.406 (3.89), 7.417 (3.04), 7.421 (3.07), 7.697 (6.51), 7.702 (6.34).

Example 9A

Ethyl 1-[1-{5-chloro-2-[(4-methoxyphenyl)methoxy]phenyl}piperidin-3-yl]-5-(difluoromethyl)-1H-pyrazole-4-carboxylate (Enantiomer 1)

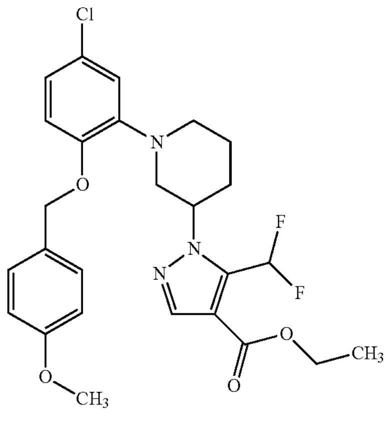 [SMILES: CCOC(=O)c1cnn(C2CCCN(c3cc(Cl)ccc3OCc3ccc(OC)cc3)C2)c1C(F)F]

Under argon, a solution of 2-bromo-4-chloro-1-[(4-methoxyphenyl)methoxy]benzene (prepared in analogy to Example 8A, 10.0 g, 30.5 mmol) and ethyl 5-(difluoromethyl)-1-[piperidin-3-yl]-1H-pyrazole-4-carboxylate (prepared in analogy to Example 6A, Enantiomer 1, 8.34 g, 30.5 mmol) in 1,4-dioxane (100 ml) was treated with caesium carbonate (29.8 g, 91.6 mmol), $Pd_2dba_3$ (2.80 g, 3.05 mmol) and rac-BINAP (3.80 g, 6.10 mmol) and the resulting mixture was stirred overnight at 100° C. The reaction mixture was combined with a 500 mg test reaction, filtered over celite, rinsed with ethyl acetate and evaporated. The residue was retaken in water and extracted three times with ethyl acetate. The combined organic layers were washed with a saturated solution of sodium chloride, dried over sodium sulphate and evaporated. The residue was purified by flash chromatography (silica gel, cyclohexane/ethyl acetate gradient) affording 10.1 g (60% yield) of the title compound.

LC-MS (Method 4): Rr=1.44 min; MS (ESIpos): m/z=520 $[M+H]^+$

Example 10A

Ethyl 1-[1-(5-chloro-2-hydroxyphenyl)piperidin-3-yl]-5-(difluoromethyl)-1H-pyrazole-4-carboxylate (Enantiomer 1)

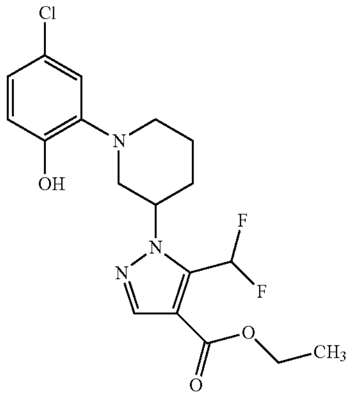 [SMILES: CCOC(=O)c1cnn(C2CCCN(c3cc(Cl)ccc3O)C2)c1C(F)F]

A solution of ethyl 1-[1-{5-chloro-2-[(4-methoxyphenyl)methoxy]phenyl}piperidin-3-yl]-5-(difluoromethyl)-1H-pyrazole-4-carboxylate (Example 9A, Enantiomer 1, 10.1 g, 19.4 mmol) in dichloromethane (200 ml) was treated with trifluoroacetic acid and stirred over night at room temperature. The reaction mixture was evaporated. The residue was retaken in ethyl acetate and washed once with water, once with a saturated solution of sodium hydrogencarbonate and finally once with a saturated solution of sodium chloride. The organic phase was dried over sodium sulphate and evaporated. The residue was purified by flash chromatography (silica gel, cyclohexane/ethyl acetate gradient) affording 7.17 g (83% purity, 77% yield) of the title compound.

LC-MS (Method 8): Rr=1.26 min; MS (ESIpos): m/z=400 $[M+H]^+$

Example 11A

Ethyl 1-[i-{5-chloro-2-[(trifluoromethanesulfonyl) oxy]phenyl}piperidin-3-yl]-5-(difluoromethyl)-1H-pyrazole-4-carboxylate (Enantiomer 1)

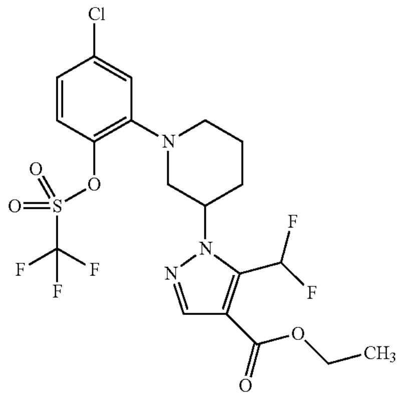 [SMILES: CCOC(=O)c1cnn(C2CCCN(c3cc(Cl)ccc3OS(=O)(=O)C(F)(F)F)C2)c1C(F)F]

Under argon, a solution of ethyl 1-[1-(5-chloro-2-hydroxyphenyl)piperidin-3-yl]-5-(difluoromethyl)-1H-pyrazole-4-carboxylate (Example 10A, Enantiomer 1, 7.17 g, 83% purity, 14.9 mmol) in dichloromethane (160 ml) was treated with triethylamine (5.2 ml, 37 mmol) and cooled to 0° C. Trifluoromethanesulfonic anhydride was added dropwise and the resulting mixture was stirred 45 minutes at 0° C. The reaction mixture was diluted with dichloromethane (150 ml) and washed three times with water. The organic phase was dried over sodium sulphate and evaporated. The residue was purified by flash chromatography (silica gel, cyclohexane/ethyl acetate gradient) affording 7.89 g (quant.) of the title compound.

LC-MS (Method 4): Rr=1.47 min; MS (ESIpos): m/z=532 $[M+H]^+$

Example 12A

Ethyl 1-[1-{5-chloro-2-[(4-methoxyphenyl) methoxy]phenyl}piperidin-3-yl]-5-(difluoromethyl)-1H-pyrazole-4-carboxylate (Enantiomer 2)

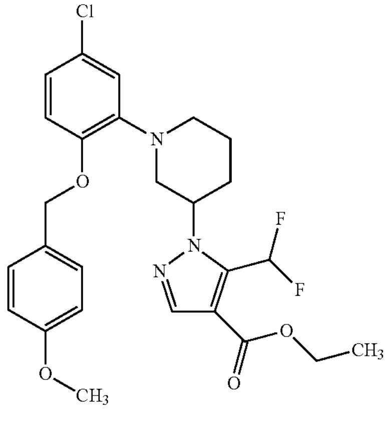 [SMILES: CCOC(=O)c1cnn(C2CCCN(c3cc(Cl)ccc3OCc3ccc(OC)cc3)C2)c1C(F)F]

Under argon, a solution of ethyl 5-(difluoromethyl)-1-[piperidin-3-yl]-1H-pyrazole-4-carboxylate (prepared in analogy to Example 7A, Enantiomer 2, 43.6 g, 160 mmol) and 2-bromo-4-chloro-1-[(4-methoxyphenyl)methoxy]benzene (prepared in analogy to Example 8A, 52.3 g, 160 mmol) in 1,4-dioxane (680 ml) was treated with $Pd_2(dba)_3$ (14.6 g, 16.0 mmol), rac-BINAP (19.9 g, 31.9 mmol) and freshly ground caesium carbonate (156 g, 479 mmol) and stirred 18 hours at 100° C. The reaction mixture was diluted with ethyl acetate and a 10% solution of sodium chloride, filtered over Celite and rinsed with ethyl acetate. The aqueous phase of the filtrate was extracted with ethyl acetate. The combined organic layers were washed with a 10% solution of sodium chloride, dried over sodium sulphate and evaporated. The residue was purified flash chromatography over silica gel (dichloromethane/petrol ether 4:1) affording 42 g (82% yield) of the title compound.

LC-MS (Method 3): Rr=2.78 min; MS (ESIpos): m/z=520 $[M+H]^+$ $^1$H-NMR (400 MHz, DMSO-d6) δ[ppm]: 1.272 (3.65), 1.290 (7.68), 1.307 (3.76), 1.686 (0.44), 1.717 (0.54), 1.852 (0.73), 1.885 (0.50), 1.989 (0.47), 2.019 (0.56), 2.058 (0.99), 2.084 (0.61), 2.587 (0.51), 2.616 (0.89), 2.642 (0.45), 3.030 (0.76), 3.057 (1.51), 3.084 (0.83), 3.447 (0.72), 3.474 (0.69), 3.613 (0.74), 3.640 (0.67), 3.737 (16.00), 4.251 (1.13), 4.269 (3.48), 4.287 (3.45), 4.304 (1.12), 4.624 (0.40), 4.639 (0.48), 4.650 (0.76), 4.661 (0.51), 5.035 (6.45), 6.872 (3.47), 6.893 (5.67), 6.947 (0.98), 6.952 (0.85), 6.968 (1.72), 6.974 (1.67), 7.017 (2.84), 7.039 (1.57), 7.305 (3.66), 7.326 (3.43), 7.340 (0.56), 7.380 (0.41), 7.439 (0.93), 7.463 (0.64), 7.476 (0.48), 7.569 (1.65), 7.699 (0.76), 8.044 (3.66).

Example 13A

Ethyl 1-[1-(5-chloro-2-hydroxyphenyl)piperidin-3-yl]-5-(difluoromethyl)-1H-pyrazole-4-carboxylate (Enantiomer 2)

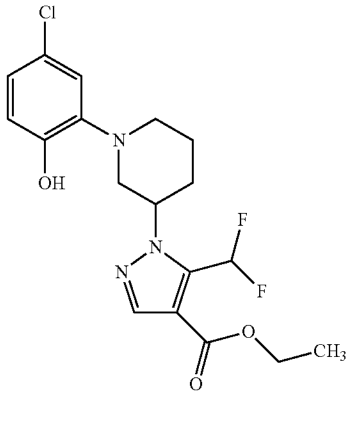 [SMILES: CCOC(=O)c1cnn(C2CCCN(c3cc(Cl)ccc3O)C2)c1C(F)F]

A solution of ethyl 1-[1-{5-chloro-2-[(4-methoxyphenyl) methoxy]phenyl}piperidin-3-yl]-5-(difluoromethyl)-1H-pyrazole-4-carboxylate (prepared in analogy to Example 12A, Enantiomer 2, 67.5 g, 130 mmol) in dichloromethane (1.0 l) was treated with trifluoroacetic acid (100 ml, 1.3 mol) and stirred overnight at room temperature. The reaction mixture was diluted with water (750 ml) and carefully treated with a 10% solution of sodium carbonate (450 ml) until no more carbon dioxide was generated. The organic phase was dried over sodium sulphate and evaporated affording 52 g (90% yield) of the title compound which was used in the next step without further purification.

LC-MS (Method 3): Rr=2.42 min; MS (ESIpos): m/z=400 $[M+H]^+$

Example 14A

Ethyl 1-[1-{5-chloro-2-[(trifluoromethanesulfonyl)oxy]phenyl}piperidin-3-yl]-5-(difluoromethyl)-1H-pyrazole-4-carboxylate (Enantiomer 2)

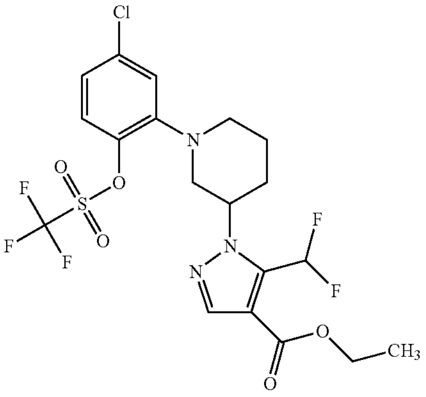 [SMILES: CCOC(=O)c1cnn(C2CCCN(c3cc(Cl)ccc3OS(=O)(=O)C(F)(F)F)C2)c1C(F)F]

A solution of ethyl 1-[1-(5-chloro-2-hydroxyphenyl)piperidin-3-yl]-5-(difluoromethyl)-1H-pyrazole-4-carboxylate (Example 13A, Enantiomer 2, 52.0 g, 117 mmol) and triethylamine (49 ml, 350 mmol) in dichloromethane (330 ml) was cooled to −50° C. Trifluoromethanesulfonic acid (28 ml, 160 mmol) was added dropwise and the resulting mixture was stirred 1 hour at −50° C. The reaction mixture was then diluted with dichloromethane (330 ml) and water (370 ml). The aqueous phase was extracted with dichloromethane (330 ml). The combined organic layers were washed with (370 ml), dried over sodium sulphate and evaporated. The resulting mixture was purified by flash chromatography (silica gel, dichloromethane/petrol ether 6:4) affording 60 g (96% yield) of the title compound.

LC-MS (Method 3): Rr=2.74 min; MS (ESIpos): m/z=532 $[M+H]^+$ $^1$H-NMR (600 MHz, DMSO-d6) δ[ppm]: −0.021 (0.65), 1.082 (0.51), 1.270 (7.69), 1.282 (16.00), 1.294 (7.63), 1.772 (0.48), 1.780 (0.51), 1.787 (0.63), 1.793 (0.66), 1.801 (0.62), 1.808 (0.60), 1.910 (1.25), 1.914 (0.99), 1.927 (0.67), 1.932 (0.89), 2.068 (0.72), 2.075 (1.03), 2.086 (2.45), 2.091 (2.40), 2.100 (1.41), 2.792 (0.71), 2.796 (0.83), 2.812 (1.48), 2.816 (1.50), 2.832 (0.83), 2.836 (0.72), 3.142 (1.17), 3.161 (1.04), 3.201 (1.21), 3.219 (2.80), 3.237 (1.83), 3.278 (1.37), 3.285 (1.56), 4.251 (2.26), 4.263 (7.09), 4.275 (7.06), 4.287 (2.20), 4.755 (0.50), 4.765 (0.90), 4.773 (0.89), 4.781 (0.90), 4.791 (0.49), 5.734 (2.17), 7.261 (2.19), 7.265 (2.27), 7.275 (2.69), 7.279 (2.82), 7.391 (4.65), 7.406 (3.75), 7.431 (4.73), 7.435 (4.51), 7.492 (1.26), 7.579 (2.61), 7.666 (1.07), 8.026 (6.37).

Example 15A

Tert-butyl 4-(4'-chloro-2'-{3-[5-(difluoromethyl)-4-(ethoxycarbonyl)-1H-pyrazol-1-yl]piperidin-1-yl}[1,1'-biphenyl]-4-yl)piperazine-1-carboxylate (Enantiomer 2)

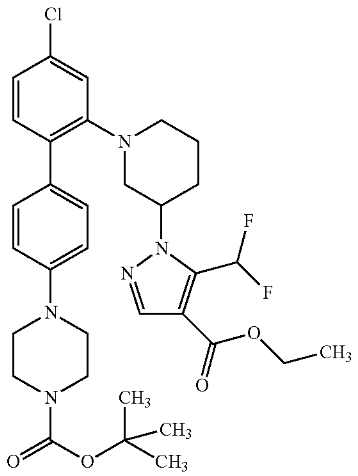 [SMILES: CCOC(=O)c1cnn(C2CCCN(c3cc(Cl)ccc3-c3ccc(N4CCN(C(=O)OC(C)(C)C)CC4)cc3)C2)c1C(F)F]

Under argon, a solution of ethyl 1-[1-{5-chloro-2-[(trifluoromethanesulfonyl)oxy]phenyl}piperidin-3-yl]-5-(difluoromethyl)-1H-pyrazole-4-carboxylate (Example 14A, Enantiomer 2, 57.0 g, 107 mmol) and tert-butyl 4-[4-(4,4,5,5-tetramethyl-1,3,2-dioxaborolan-2-yl)phenyl]piperazine-1-carboxylate [CAS No. 470478-90-1] (49.9 g, 129 mmol) in toluene (600 ml) and ethanol (600 ml) was treated with an aqueous solution of sodium carbonate (160 ml, 2.0 M, 320 mmol) and Tetrakis(triphenylphosphine)palladium(0) (6.19 g, 5.36 mmol). The resulting mixture was stirred 4 hours at 100° C. The reaction mixture was cooled to room temperature, filtered over Celite, washed with ethyl acetate and evaporated. The residue was purified by flash chromatography (silica gel, petrol ether/ethyl acetate 9:1 to 8:2) affording 62 g (89% yield) of the title compound.

LC-MS (Method 3): $R_t$=3.15 min; MS (ESIpos): m/z=644 $[M+H]^+$

Example 16A

Ethyl 1-{1-[4-chloro-4'-(piperazin-1-yl)[1,1'-biphenyl]-2-yl]piperidin-3-yl}-5-(difluoromethyl)-1H-pyrazole-4-carboxylate hydrochloride (Enantiomer 2)

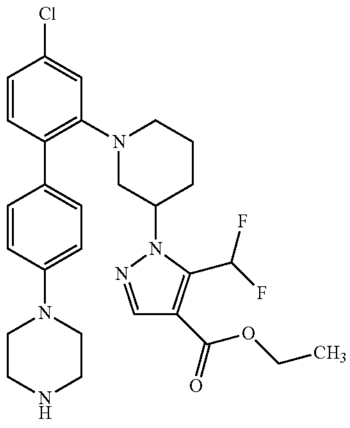 [SMILES: CCOC(=O)c1cnn(C2CCCN(c3cc(Cl)ccc3-c3ccc(N4CCNCC4)cc3)C2)c1C(F)F]

A solution of tert-butyl 4-(4'-chloro-2'-{3-[5-(difluoromethyl)-4-(ethoxycarbonyl)-1H-pyrazol-1-yl]piperidin-1-yl}[1,1'-biphenyl]-4-yl)piperazine-1-carboxylate (Example 15A, Enantiomer 2, 60.0 g, 93.1 mmol) in dichloromethane (250 ml) was treated with a solution of hydrogen chloride in dioxane (230 ml, 4.0 M, 930 mmol). The resulting mixture was stirred 3 hours at room temperature and evaporated. The residue was co-evaporated twice with diethyl ether (250 ml×2), stirred 4 days in diisopropyl ether. The suspension was filtered, the solid was washed twice with diisopropyl ether affording 57 g (quant.) of the title compound.

LC-MS (Method 3): Rr=1.78 min; MS (ESIpos): m/z=544 $[M+H]^+$ $^1H$-NMR (400 MHz, DMSO-d6) δ[ppm]: 1.029 (13.49), 1.044 (13.77), 1.262 (7.53), 1.280 (16.00), 1.297 (7.81), 1.496 (0.79), 1.506 (0.62), 1.527 (0.91), 1.559 (0.40), 1.716 (1.24), 1.749 (0.95), 1.888 (0.84), 1.897 (0.78), 1.918 (0.98), 1.926 (0.93), 1.966 (1.38), 1.995 (0.69), 2.580 (1.54), 2.606 (0.83), 2.992 (1.21), 3.018 (2.69), 3.044 (2.33), 3.063 (1.24), 3.435 (5.96), 3.448 (7.25), 3.460 (5.00), 3.570 (5.78), 3.586 (0.87), 3.601 (1.12), 3.616 (0.85), 4.227 (5.38), 4.238 (6.62), 4.256 (9.26), 4.273 (7.97), 4.291 (2.70), 4.444 (0.41), 4.455 (0.77), 4.470 (0.89), 4.481 (1.31), 4.491 (0.92), 4.507 (0.68), 7.045 (6.02), 7.067 (6.86), 7.074 (5.10), 7.079 (5.42), 7.099 (2.25), 7.104 (1.49), 7.120 (3.55), 7.125 (3.10), 7.164 (6.27), 7.185 (3.37), 7.383 (1.62), 7.483 (6.90), 7.505 (6.40), 7.513 (3.75), 7.643 (1.34), 8.005 (5.77), 9.399 (1.97).

Example 17A

Ethyl 1-[1-{4-chloro-4'-[4-(2-methylpropyl)piperazin-1-yl][1,1'-biphenyl]-2-yl}piperidin-3-yl]-5-(difluoromethyl)-1H-pyrazole-4-carboxylate (Enantiomer 2)

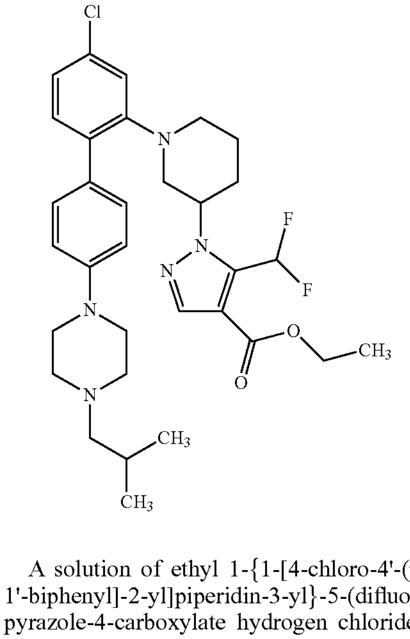

A solution of ethyl 1-{1-[4-chloro-4'-(piperazin-1-yl)[1,1'-biphenyl]-2-yl]piperidin-3-yl}-5-(difluoromethyl)-1H-pyrazole-4-carboxylate hydrogen chloride (Example 16A, Enantiomer 2, 52.0 g, 84.3 mmol) in THF was treated with N,N-diisopropylethylamine (59 ml, 340 mmol) and 2-methylpropanal [CAS No. 78-84-2] (38 ml, 420 mmol) and stirred 1 hour at room temperature. Sodium triacetoxyborohydride (71.5 g, 337 mmol) was then added and the resulting mixture was stirred 18 hours at room temperature. The reaction mixture was diluted with an aqueous solution of sodium hydrogen carbonate (10%) and ethyl acetate. The aqueous layer was extracted twice with ethyl acetate. The combined organic layers were washed with an aqueous solution of sodium chloride, dried over sodium sulphate and evaporated. The residue was purified by flash chromatography (silica gel, petrol ether/ethyl acetate 8:2) affording 47 g (93% yield) of the title compound.

LC-MS (Method 9): Rr=3.42 min; MS (ESIpos): m/z=600 $[M+H]^+$

Example 18A

1-(2-Methylpropyl)-4-[4-(4,4,5,5-tetramethyl-1,3,2-dioxaborolan-2-yl)phenyl]piperazine

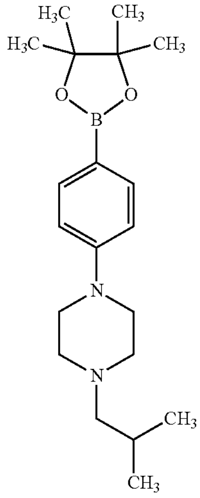 [SMILES: CC(C)CN1CCN(c2ccc(B3OC(C)(C)C(C)(C)O3)cc2)CC1]

1-[4-(4,4,5,5-tetramethyl-1,3,2-dioxaborolan-2-yl)phenyl]piperazine (350 mg, 1.21 mmol) was placed in 7.4 ml THF and N,N-diisopropylethylamine (320 μl, 1.8 mmol) was added. Then 2-methylpropanal (440 μl, 4.9 mmol) was added and the mixture was stirred for 10 min. Then sodium triacetoxyborohydride (772 mg, 3.64 mmol) was added and the mixture was stirred at 55° C. for 4 h. The reaction mixture was cooled to room temperature, saturated aqueous sodium bicarbonate solution was added and the mixture was extracted three times with ethyl acetate. The combined organic phases were washed once with saturated, aqueous sodium chloride solution, dried over sodium sulphate, filtered and evaporated. 342 mg of the target compound (79% of theory, purity 97%) were obtained.

LC-MS (Method 3): Rr=1.23 min; MS (ESIpos): m/z=345 $[M+H]^+$ $^1H$-NMR (600 MHz, DMSO-d6) δ[ppm]: 0.058 (0.55), 0.927 (4.09), 0.938 (4.13), 1.316 (16.00), 2.121 (0.98), 2.133 (0.89), 2.492 (0.99), 2.508 (0.99), 2.559 (2.25), 2.599 (2.62), 3.241 (1.07), 3.249 (1.38), 3.257 (0.98), 6.935 (1.05), 6.949 (1.07), 7.552 (1.15), 7.566 (1.07).

Experimental Section—Example Compounds

Example 1

1-[1-{4-Chloro-4'-[4-(2-methylpropyl)piperazin-1-yl][1,1'-biphenyl]-2-yl}piperidin-3-yl]-5-(difluoromethyl)-1H-pyrazole-4-carboxylic acid hydrochloride (Enantiomer 1)

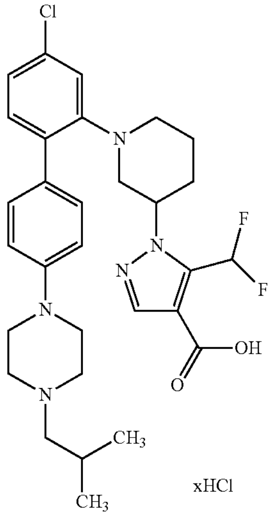 [SMILES: CC(C)CN1CCN(c2ccc(-c3ccc(Cl)cc3N3CCCC(n4ncc(C(=O)O)c4C(F)F)C3)cc2)CC1]

xHCl

Ethyl 1-[1-{5-chloro-2-[(trifluoromethanesulfonyl)oxy]phenyl}piperidin-3-yl]-5-(difluoromethyl)-1H-pyrazole-4-carboxylate (prepared in analogy to Example 11A, Enantiomer 1, 80.0 mg, 147 μmol) and 1-(2-methylpropyl)-4-[4-(4,4,5,5-tetramethyl-1,3,2-dioxaborolan-2-yl)phenyl]piperazine (Example 18A 62.8 mg, 97% purity, 177 μmol) were placed under argon in toluene/ethanol (820/820 μl). 2 M sodium carbonate solution (220 μl, 2.0 M, 440 μmol) and tetrakis(triphenylphosphine)palladium(0) (8.52 mg, 7.37 μmol) were added and the mixture was stirred at 100° C. overnight. The reaction mixture was diluted with ethyl acetate and 1 M hydrochloric acid was added. The aqueous phase was extracted three times with ethyl acetate. The organic phase was dried with sodium sulfate, filtered off and evaporated. The crude mixture was dissolved with THF/ethanol (2.0/0.2 ml), 1 M lithium hydroxide solution (1.5 ml, 1.5 mmol) was added and the mixture was stirred at room temperature overnight. A 1 M lithium hydroxide solution (740 μl, 740 μmol) was added again. After about 6 h the reaction mixture was evaporated at 50° C. The residue was dissolved in acetonitrile/water/0.25 ml trifluoroacetic acid and purified by preparative HPLC (RP18 column, acetonitrile/water gradient with the addition of 0.1% trifluoroacetic acid). The crude product was purified by means of thick layer chromatography (dichloromethane/methanol/formic acid: 10/1/0.1). The silica gel mixture was stirred with dichloromethane/1 M hydrochloric acid in dioxane (10/1) in ethanol, filtered off and carefully evaporated at 30° C. and lyophilized. 34 mg of the target compound (36% of theory, purity 95%) were is obtained.

LC-MS (Method 6): Rr=1.23 min; MS (ESIpos): m/z=572 $[M-HCl+H]^+$ $^1$H-NMR (600 MHz, DMSO-d6) δ[ppm]: 1.004 (15.87), 1.015 (16.00), 1.500 (0.51), 1.521 (0.57), 1.728 (0.73), 1.750 (0.61), 1.897 (0.57), 1.917 (0.62), 1.975 (0.79), 2.122 (0.42), 2.133 (0.84), 2.144 (1.02), 2.156 (0.79), 2.571 (0.47), 2.587 (0.91), 2.610 (0.52), 3.004 (0.84), 3.022 (2.01), 3.026 (2.20), 3.038 (3.72), 3.048 (2.50), 3.065 (0.75), 3.154 (2.66), 3.161 (2.75), 3.169 (2.36), 3.177 (1.88), 3.224 (0.84), 3.237 (0.70), 3.589 (1.41), 3.602 (1.80), 3.825 (1.02), 3.841 (0.78), 3.866 (1.05), 3.882 (0.75), 4.223 (2.57), 4.445 (0.68), 4.463 (0.97), 4.481 (0.57), 7.045 (0.55), 7.055 (3.63), 7.070 (3.72), 7.084 (2.72), 7.087 (3.09), 7.110 (1.47), 7.113 (1.11), 7.123 (2.19), 7.127 (2.02), 7.163 (3.67), 7.177 (2.19), 7.215 (0.46), 7.428 (0.83), 7.495 (4.24), 7.510 (4.02), 7.515 (2.07), 7.602 (0.82), 7.959 (4.79), 9.484 (0.54).

Example 2

1-[1-{4-Chloro-4'-[4-(2-methylpropyl)piperazin-1-yl][1,1'-biphenyl]-2-yl}piperidin-3-yl]-5-(difluoromethyl)-1H-pyrazole-4-carboxylic acid (Enantiomer 2)

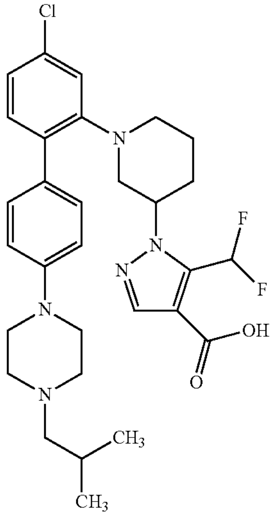 [SMILES: CC(C)CN1CCN(c2ccc(-c3ccc(Cl)cc3N3CCCC(n4ncc(C(=O)O)c4C(F)F)C3)cc2)CC1]

Method A

A solution of ethyl 1-[1-{4-chloro-4'-[4-(2-methylpropyl)piperazin-1-yl][1,1'-biphenyl]-2-yl}piperidin-3-yl]-5-(difluoromethyl)-1H-pyrazole-4-carboxylate (prepared in analogy to Example 17A, Enantiomer 2, 50.8 g, 84.6 mmol) in a THF/methanol mixture 9:1 (1.0 l) was treated with an aqueous solution of lithium hydroxide (850 ml, 1.0 M, 850 mmol) and stirred overnight at room temperature. The reaction mixture was concentrated, diluted with dichloromethane (1.5 l) and adjusted to pH=2 with an aqueous solution of hydrogen chloride (2N). The resulting suspension was stirred 45 minutes at room temperature. The solid was filtered, washed with water and dried under vacuum affording 43 g (90% yield) of the title compound.

LC-MS (Method 7): Rr=1.27 min; MS (ESIpos): m/z=572 $[M+H]^+$ $^1$H-NMR (600 MHz, DMSO-d6) δ[ppm]: 1.002 (15.68), 1.013 (16.00), 1.080 (0.57), 1.092 (1.18), 1.103 (0.63), 1.498 (0.74), 1.519 (0.83), 1.719 (1.03), 1.741 (0.88), 1.902 (0.78), 1.908 (0.74), 1.922 (0.88), 1.928 (0.83), 1.943 (0.45), 1.978 (1.13), 1.994 (0.74), 2.102 (0.71), 2.112 (0.85), 2.123 (0.70), 2.571 (1.40), 2.591 (0.77), 2.882 (1.10), 3.018 (1.27), 3.035 (3.01), 3.053 (2.14), 3.239 (2.40), 3.254 (2.32), 3.368 (1.13), 3.379 (1.40), 3.391 (1.33), 3.403 (0.92), 3.493 (0.76), 4.463 (0.65), 4.482 (1.12), 4.500 (0.62), 7.033 (4.22), 7.048

(4.45), 7.074 (3.47), 7.077 (4.04), 7.100 (1.85), 7.103 (1.52), 7.113 (2.53), 7.117 (2.34), 7.162 (4.18), 7.175 (2.71), 7.439 (1.03), 7.481 (4.88), 7.495 (4.57), 7.526 (2.04), 7.613 (0.91), 7.952 (5.28).

Method B

1-{1-[4-Chloro-4'-(4-isobutylpiperazin-1-yl)[biphenyl]-2-yl]piperidin-3-yl}-5-(difluoromethyl)-1H-pyrazole-4-carboxylic acid hydrochloride (prepared in analogy to Example 3, Enantiomer 2, 31.2 mg, 51.3 µmol) were dissolved in 17 ml of dichloromethane and 1 ml of methanol. The solution was shaken once with 1.5 ml of saturated, aqueous sodium bicarbonate solution. The phases were separated. 5 ml of dichloromethane and 3 ml of methanol were added to the organic phase. The organic phase was then dried over sodium sulfate, filtered, evaporated and purified by preparative HPLC (RP18 column, acetonitrile/water gradient, neutral without acid addition). Product fractions were combined and lyophilized. 22 mg of the target compound (74% of theory) were obtained.

LC-MS (Method 3): Rr=1.73 min; MS (ESIpos): m/z=572 $[M+H]^+$ $^1$H-NMR (600 MHz, DMSO-d6) δ[ppm]: 0.887 (15.60), 0.898 (16.00), 1.493 (0.64), 1.514 (0.70), 1.695 (0.89), 1.718 (0.74), 1.799 (0.48), 1.811 (0.88), 1.822 (1.12), 1.833 (0.92), 1.844 (0.48), 1.890 (0.68), 1.910 (0.74), 1.977 (0.93), 1.995 (0.62), 2.118 (3.91), 2.130 (3.66), 2.516 (5.14), 3.017 (1.09), 3.035 (2.76), 3.053 (1.94), 3.181 (5.03), 3.185 (5.02), 3.267 (1.53), 4.473 (0.55), 4.491 (0.96), 4.509 (0.54), 6.963 (3.96), 6.977 (4.06), 7.048 (3.13), 7.051 (3.31), 7.081 (1.60), 7.084 (1.26), 7.095 (2.21), 7.098 (1.89), 7.152 (3.52), 7.165 (2.42), 7.434 (4.45), 7.448 (4.50), 7.533 (1.51), 7.621 (0.67), 7.930 (4.14).

Example 3

1-{1-[4-Chloro-4'-(4-isobutylpiperazin-1-yl)[biphenyl]-2-yl]piperidin-3-yl}-5-(difluoromethyl)-1H-pyrazole-4-carboxylic acid hydrochloride (Enantiomer 2)

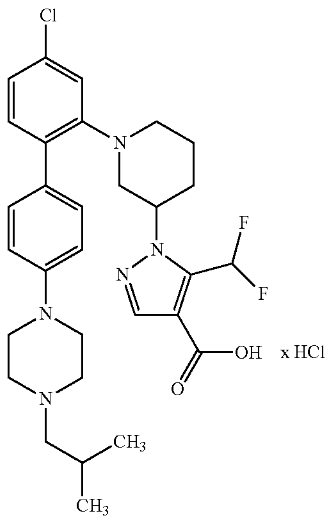 [SMILES: CC(C)CN1CCN(c2ccc(-c3ccc(Cl)cc3N3CCCC(n4ncc(C(=O)O)c4C(F)F)C3)cc2)CC1 ; "x HCl"]

Method A

A suspension of 1-[1-{4-chloro-4'-[4-(2-methylpropyl)piperazin-1-yl][1,1'-biphenyl]-2-yl}piperidin-3-yl]-5-(difluoromethyl)-1H-pyrazole-4-carboxylic acid (prepared in analogy to Example 2, Enantiomer 2, 43.5 g, 76.0 mmol) in diethyl ether (870 ml) was treated with a solution of hydrogen chloride in diethyl ether (84 ml, 1.0 M, 84 mmol). The resulting mixture was stirred overnight at room temperature and evaporated affording 46.1 g (quant.) of the title compound.

LC-MS (Method 3): $R_t$=1.72 min; MS (ESIpos): m/z=572 $[M+H]^+$ $^1$H-NMR (600 MHz, DMSO-d6) δ[ppm]: 1.026 (15.64), 1.037 (16.00), 1.497 (0.56), 1.519 (0.61), 1.722 (0.78), 1.743 (0.65), 1.903 (0.59), 1.910 (0.53), 1.924 (0.66), 1.930 (0.61), 1.978 (0.82), 1.994 (0.50), 2.142 (0.45), 2.154 (0.91), 2.165 (1.11), 2.176 (0.89), 2.187 (0.45), 2.557 (0.64), 2.577 (1.02), 2.594 (0.55), 2.992 (1.81), 3.002 (2.77), 3.012 (1.87), 3.018 (1.15), 3.036 (2.40), 3.054 (1.60), 3.133 (1.12), 3.148 (1.19), 3.168 (0.53), 3.237 (0.88), 3.250 (0.76), 3.338 (0.81), 3.360 (1.42), 3.379 (0.88), 3.580 (1.61), 3.791 (0.89), 3.819 (1.25), 3.844 (0.81), 4.463 (0.89), 4.474 (0.97), 4.481 (1.26), 4.488 (0.99), 4.499 (0.88), 7.051 (3.56), 7.065 (3.77), 7.077 (2.72), 7.080 (3.14), 7.103 (1.42), 7.106 (1.13), 7.116 (2.00), 7.120 (1.84), 7.165 (3.40), 7.178 (2.22), 7.443 (0.84), 7.489 (4.04), 7.504 (3.79), 7.531 (1.66), 7.618 (0.72), 7.954 (4.33), 10.519 (0.49).

Method B

Ethyl 1-[1-{5-chloro-2-[(trifluoromethanesulfonyl)oxy]phenyl}piperidin-3-yl]-5-(difluoromethyl)-1H-pyrazole-4-carboxylate (prepared in analogy to Example 14A, Enantiomer 2, 80.0 mg, 150 µmol) and 1-(2-methylpropyl)-4-[4-(4,4,5,5-tetramethyl-1,3,2-dioxaborolan-2-yl)phenyl]piperazine (Example 18A 64.1 mg, 97% purity, 180 µmol) were dissolved under argon in toluene/ethanol (0.83/0.83 ml). Tetrakis(triphenylphosphine)palladium(0) (8.69 mg, 7.52 µmol) and 2 M sodium carbonate solution (226 µl, 452 µmol) were added and the mixture was stirred at 100° C. overnight. The reaction mixture was diluted with ethyl acetate and water. The aqueous phase was acidified with 1 M hydrochloric acid. The phases were separated and the aqueous phase was extracted twice with ethyl acetate. The combined organic phases were dried over sodium sulfate, filtered and evaporated. The crude product was dissolved in THF/ethanol (3.9/0.39 ml), 1 M aqueous lithium hydroxide solution (1.5 ml, 1.5 mmol) was added and the mixture was stirred overnight at room temperature. The mixture was evaporated, the residue was dissolved in acetonitrile/TFA/water and purified using preparative HPLC (RP18 column, acetonitrile/water gradient with the addition of 0.1% TFA). The product fractions were combined and evaporated. The residue was mixed with 0.1 M hydrochloric acid in dioxane, carefully evaporated at 30° C. (twice) and then lyophilized. 53 mg of the target compound (55% of theory, purity 95%) were obtained.

LC-MS (Method 4): Rr=0.91 min; MS (ESIpos): m/z=572 $[M-HCl+H]^+$ $^1$H-NMR (400 MHz, DMSO-d6) δ[ppm]: 1.004 (15.46), 1.020 (16.00), 1.491 (0.44), 1.522 (0.50), 1.722 (0.68), 1.753 (0.55), 1.890 (0.47), 1.920 (0.55), 1.967 (0.84), 2.129 (0.76), 2.146 (0.96), 2.163 (0.76), 2.582 (0.91), 2.613 (0.48), 2.999 (0.86), 3.010 (1.71), 3.025 (3.88), 3.041 (2.30), 3.131 (0.88), 3.161 (1.25), 3.177 (2.08), 3.213 (1.75), 3.242 (1.16), 3.467 (1.06), 3.496 (0.84), 3.503 (0.60), 3.519 (0.54), 3.525 (0.50), 3.549 (0.75), 3.555 (0.84), 3.572 (1.57), 3.582 (1.48), 3.589 (1.38), 3.601 (2.78), 3.608 (1.89), 3.633 (0.44), 3.640 (0.41), 3.811 (0.94), 3.847 (1.32), 3.878 (0.71), 4.329 (0.49), 4.439 (0.46), 4.466 (0.73), 4.477 (0.52), 4.839 (0.49), 7.047 (3.30), 7.070 (3.64), 7.082 (2.61), 7.087 (3.29), 7.104 (1.46), 7.109 (0.86), 7.124 (2.34), 7.129 (2.03), 7.160 (3.99), 7.181

(1.96), 7.388 (0.88), 7.490 (4.02), 7.512 (3.81), 7.519 (2.20), 7.650 (0.72), 7.959 (3.78), 9.708 (0.41).

$[\alpha]_D^{20}$=−73.05°, c=0.465 g/100 $cm^3$, trichloromethane.

Example 3 Enantiomer 2 has an absolute configuration of R as shown in example 4 below.

1-{3(R)-1-[4-Chloro-4'-(4-isobutylpiperazin-1-yl)[biphenyl]-2-yl]piperidin-3-yl}-5-(difluoromethyl)-1H-pyrazole-4-carboxylic acid hydrochloride Example 4

1-{3(R)-1-[4-Chloro-4'-(4-isobutylpiperazin-1-yl)[biphenyl]-2-yl]piperidin-3-yl}-5-(difluoromethyl)-1H-pyrazole-4-carboxylic acid hydrochloride hemi-hydrate

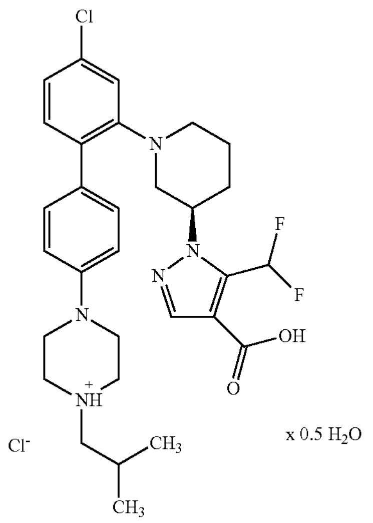 [SMILES: [Cl-] ; CC(C)CN1CCN(c2ccc(-c3ccc(Cl)cc3N3CCC[C@@H](n4ncc(C(=O)O)c4C(F)F)C3)cc2)CC1]

100 mg 1-{1-[4-Chloro-4'-(4-isobutylpiperazin-1-yl)[biphenyl]-2-yl]piperidin-3-yl}-5-(difluoromethyl)-1H-pyrazole-4-carboxylic acid hydrochloride (Enantiomer 2) (example 3) were solved at 60° C. in 3.5 ml 2-propanol, wherein the 2-propanol was dosed portionwise in 100 µl-portions at 60° C. until a clear solution was obtained. Afterwards the vessel was closed with a septum and placed into a slowly cooling sand bath from 60° C. to room temperature over the weekend→small amounts of solids were detected. Thereafter the septum was provided with a cannula, in order to slowly let the solvent evaporate. After 4 weeks crystals were collected and inspected under a microscope.

Single Crystal X-Ray Structure Analysis:

The Crystal structure determination was carried out using a Bruker diffractometer (QS-no.: 02506) equipped with an Apex II-CCD area detector, an IµS-microsource with CuKa radiation, mirrors as monochromator and a Cryostream low temperature device (T=110 K). Fullsphere data collection, omega and phi scans. Programs used: Data collection and reduction Apex II v2014.11.0 (Bruker AXS, 2014), absorption correction/scaling SADABS. Crystal structure solution was achieved using direct methods as implemented in SHELXTL Version 6.14 (Bruker AXS, 2003) and visualized using XP program. Missing atoms were subsequently located from difference Fourier synthesis and added to the atom list. Least-squares refinement on F2 using all measured intensities was carried out using the program SHELXTL Version 6.14 (Bruker AXS, 2003). All non hydrogen atoms were refined including anisotropic displacement parameters.

| Chirality Check* | Correct structure | Inverted structure |
|---|---|---|
| Flack Parameter (standard deviation) | 0.094 (0.009) | 0.906 (0.009) |
| wR2-value (with Flack Parameter) | 0.2357 | 0.2522 |
| Chirality | R(C22) | S(C22) |

*H. D. Flack, *Acta Cryst.*, 1983, A39, 876-881

H. D. Flack, G. Bernardinelli, *J. Appl. Cryst.*, 2000, 33, 1143-1148

S. Parsons, H. D. Flack, T. Wagner, *Acta Cryst.*, 2013, B69, 249-259.

TABLE 1

Crystal data and structure refinement for example 4

| | | |
|---|---|---|
| Identification code | example 4 | |
| Empirical formula | C60 H76 Cl4 F4 N10 O5 | |
| Formula weight | 1235.10 | |
| Temperature | 110 K | |
| Wavelength | 1.54178 Å | |
| Crystal system | Trigonal | |
| Space group | $P3_221$ | |
| Unit cell dimensions | a = 9.8693(5) Å | α = 90°. |
| | b = 9.8693(5) Å | β = 90°. |
| | c = 54.159(3) Å | γ = 120°. |
| Volume | 4568.5(5) $Å^3$ | |
| Z | 3 | |
| Density (calculated) | 1.347 $Mg/m^3$ | |
| Absorption coefficient | 2.341 $mm^{-1}$ | |
| F(000) | 1950 | |
| Crystal size | 0.14 × 0.10 × 0.06 $mm^3$ | |
| Theta range for data collection | 4.899 to 63.664°. | |
| Index ranges | −11 ≤ h ≤ 10, −10 ≤ k ≤ 11, −62 ≤ l ≤ 61 | |
| Reflections collected | 27868 | |
| Independent reflections | 4640 [R(int) = 0.0378] | |
| Completeness to theta = 63.664° | 95.9% | |
| Absorption correction | Semi-empirical from equivalents | |
| Max. and min. transmission | 0.87 and 0.74 | |
| Refinement method | Full-matrix least-squares on $F^2$ | |
| Data/restraints/parameters | 4640/11/593 | |
| Goodness-of-fit on $F^2$ | 1.047 | |
| Final R indices [I > 2sigma(I)] | R1 = 0.0848, wR2 = 0.2336 | |
| R indices (all data) | R1 = 0.0864, wR2 = 0.2357 | |
| Absolute structure parameter | 0.094(9) | |
| Extinction coefficient | n/a | |
| Largest diff. peak and hole | 0.601 and −0.650 e · $Å^{-3}$ | |

TABLE 2

Bond lengths [Å] and angles [°] for example 4.

| | | | |
|---|---|---|---|
| Cl(2)—C(3) | 1.767(13) | N(4)—C(26) | 1.30(3) |
| Cl(2')—C(3') | 1.772(13) | N(4)—N(5) | 1.32(3) |
| F(1)—C(30) | 1.341(7) | N(4)—C(22) | 1.47(2) |
| F(2)—C(30) | 1.339(7) | N(5)—C(28) | 1.37(2) |
| F(1')—C(30') | 1.339(7) | N(3')—C(1') | 1.38(3) |
| F(2')—C(30') | 1.38(2) | N(3')—C(21') | 1.44(4) |

TABLE 2-continued

Bond lengths [Å] and angles [°] for example 4.

| | | | |
|---|---|---|---|
| O(1)—C(29) | 1.22(2) | N(3')—C(25') | 1.46(2) |
| O(2)—C(29) | 1.30(2) | N(4')—N(5') | 1.38(3) |
| O(2)—H(2A) | 0.8400 | N(4')—C(26') | 1.42(3) |
| O(1')—C(29') | 1.17(2) | N(4')—C(22') | 1.46(2) |
| O(2')—C(29') | 1.36(2) | N(5')—C(28') | 1.32(2) |
| O(2')—H(2B) | 0.8400 | C(1)—C(6) | 1.35(3) |
| N(1)—C(10) | 1.416(9) | C(1)—C(2) | 1.42(4) |
| N(1)—C(16) | 1.434(12) | C(2)—C(3) | 1.37(3) |
| N(1)—C(13) | 1.470(10) | C(2)—H(2D) | 0.9500 |
| N(2)—C(14) | 1.497(9) | C(3)—C(4) | 1.33(2) |
| N(2)—C(15) | 1.498(9) | C(4)—C(5) | 1.390(19) |
| N(2)—C(17) | 1.512(8) | C(4)—H(4A) | 0.9500 |
| N(2)—H(2C) | 1.0000 | C(5)—C(6) | 1.41(2) |
| N(3)—C(25) | 1.46(2) | C(5)—H(5A) | 0.9500 |
| N(3)—C(21) | 1.46(5) | C(6)—C(7) | 1.506(17) |
| N(3)—C(1) | 1.47(3) | C(7)—C(8) | 1.36(2) |
| C(7)—C(12) | 1.382(19) | C(19)—H(19C) | 0.9800 |
| C(7)—C(6') | 1.58(2) | C(20)—H(20A) | 0.9800 |
| C(8)—C(9) | 1.378(13) | C(20)—H(20B) | 0.9800 |
| C(8)—H(8A) | 0.9500 | C(20)—H(20C) | 0.9800 |
| C(9)—C(10) | 1.390(15) | C(21)—C(22) | 1.541(7) |
| C(9)—H(9A) | 0.9500 | C(21)—H(21A) | 0.9900 |
| C(10)—C(11) | 1.390(16) | C(21)—H(21B) | 0.9900 |
| C(11)—C(12) | 1.391(11) | C(22)—C(23) | 1.56(2) |
| C(11)—H(11A) | 0.9500 | C(22)—H(22A) | 1.0000 |
| C(12)—H(12A) | 0.9500 | C(23)—C(24) | 1.52(3) |
| C(13)—C(14) | 1.524(10) | C(23)—H(23A) | 0.9900 |
| C(13)—H(13A) | 0.9900 | C(23)—H(23B) | 0.9900 |
| C(13)—H(13B) | 0.9900 | C(24)—C(25) | 1.52(2) |
| C(14)—H(14A) | 0.9900 | C(24)—H(24A) | 0.9900 |
| C(14)—H(14B) | 0.9900 | C(24)—H(24B) | 0.9900 |
| C(15)—C(16) | 1.519(10) | C(25)—H(25A) | 0.9900 |
| C(15)—H(15A) | 0.9900 | C(25)—H(25B) | 0.9900 |
| C(15)—H(15B) | 0.9900 | C(26)—C(27) | 1.42(2) |
| C(16)—H(16A) | 0.9900 | C(26)—C(30) | 1.500(7) |
| C(16)—H(16B) | 0.9900 | C(27)—C(28) | 1.34(3) |
| C(17)—C(18) | 1.499(10) | C(27)—C(29) | 1.50(3) |
| C(17)—H(17A) | 0.9900 | C(28)—H(28A) | 0.9500 |
| C(17)—H(17B) | 0.9900 | C(30)—H(30A) | 1.0000 |
| C(18)—C(20) | 1.509(11) | C(1')—C(2') | 1.39(3) |
| C(18)—C(19) | 1.538(10) | C(1')—C(6') | 1.42(2) |
| C(18)—H(18A) | 1.0000 | C(2')—C(3') | 1.39(3) |
| C(19)—H(19A) | 0.9800 | C(2')—H(2E) | 0.9500 |
| C(19)—H(19B) | 0.9800 | C(3')—C(4') | 1.36(2) |
| C(4')—C(5') | 1.392(19) | C(24')—H(24C) | 0.9900 |
| C(4')—H(4B) | 0.9500 | C(24')—H(24D) | 0.9900 |
| C(5')—C(6') | 1.40(2) | C(25')—H(25C) | 0.9900 |
| C(5')—H(5B) | 0.9500 | C(25')—H(25D) | 0.9900 |
| C(21')—C(22') | 1.59(2) | C(26')—C(27') | 1.35(3) |
| C(21')—H(21C) | 0.9900 | C(26')—C(30') | 1.46(3) |
| C(21')—H(21D) | 0.9900 | C(27')—C(28') | 1.41(2) |
| C(22')—C(23') | 1.52(2) | C(27')—C(29') | 1.50(3) |
| C(22')—H(22B) | 1.0000 | C(28')—H(28B) | 0.9500 |
| C(23')—C(24') | 1.52(2) | C(30')—H(30B) | 1.0000 |
| C(23')—H(23C) | 0.9900 | O(1W)—H(1W) | 0.9010 |
| C(23')—H(23D) | 0.9900 | O(1W)—H(1W)#1 | 0.9010 |
| C(24')—C(25') | 1.55(2) | | |
| C(29)—O(2)—H(2A) | 109.5 | C(26)—N(4)—N(5) | 113(2) |
| C(29)—O(2')—H(2B) | 109.5 | C(26)—N(4)—C(22) | 127(2) |
| C(10)—N(1)—C(16) | 117.9(8) | N(5)—N(4)—C(22) | 120(2) |
| C(10)—N(1)—C(13) | 113.5(6) | N(4)—N(5)—C(28) | 104(2) |
| C(16)—N(1)—C(13) | 109.6(5) | C(1')—N(3')—C(21') | 112.1(19) |
| C(14)—N(2)—C(15) | 109.2(5) | C(1')—N(3')—C(25') | 117.2(19) |
| C(14)—N(2)—C(17) | 108.8(5) | C(21')—N(3')—C(25') | 119.2(19) |
| C(15)—N(2)—C(17) | 113.0(5) | N(5')—N(4')—C(26') | 109(2) |
| C(14)—N(2)—H(2C) | 108.6 | N(5')—N(4')—C(22') | 118.1(15) |
| C(15)—N(2)—H(2C) | 108.6 | C(26')—N(4')—C(22') | 128(2) |
| C(17)—N(2)—H(2C) | 108.6 | C(28')—N(5')—N(4') | 106.9(15) |
| C(25)—N(3)—C(21) | 107(2) | C(6)—C(1)—C(2) | 119(2) |
| C(25)—N(3)—C(1) | 116.5(18) | C(6)—C(1)—N(3) | 120.5(18) |
| C(21)—N(3)—C(1) | 112.2(18) | C(2)—C(1)—N(3) | 120(2) |
| C(3)—C(2)—C(1) | 118.4(19) | C(11)—C(10)—N(1) | 120.9(9) |
| C(3)—C(2)—H(2D) | 120.8 | C(10)—C(11)—C(12) | 120.2(11) |
| C(1)—C(2)—H(2D) | 120.8 | C(10)—C(11)—H(11A) | 119.9 |
| C(4)—C(3)—C(2) | 123.8(15) | C(12)—C(11)—H(11A) | 119.9 |
| C(4)—C(3)—Cl(2) | 120.9(12) | C(7)—C(12)—C(11) | 123.0(13) |
| C(2)—C(3)—Cl(2) | 115.1(14) | C(7)—C(12)—H(12A) | 118.5 |
| C(3)—C(4)—C(5) | 117.5(14) | C(11)—C(12)—H(12A) | 118.5 |

TABLE 2-continued

| Bond lengths [Å] and angles [°] for example 4. | | | |
|---|---|---|---|
| C(3)—C(4)—H(4A) | 121.3 | N(1)—C(13)—C(14) | 110.8(6) |
| C(5)—C(4)—H(4A) | 121.3 | N(1)—C(13)—H(13A) | 109.5 |
| C(4)—C(5)—C(6) | 121.0(15) | C(14)—C(13)—H(13A) | 109.5 |
| C(4)—C(5)—H(5A) | 119.5 | N(1)—C(13)—H(13B) | 109.5 |
| C(6)—C(5)—H(5A) | 119.5 | C(14)—C(13)—H(13B) | 109.5 |
| C(1)—C(6)—C(5) | 119.5(15) | H(13A)—C(13)—H(13B) | 108.1 |
| C(1)—C(6)—C(7) | 112.0(17) | N(2)—C(14)—C(13) | 110.7(6) |
| C(5)—C(6)—C(7) | 128.4(16) | N(2)—C(14)—H(14A) | 109.5 |
| C(8)—C(7)—C(12) | 115.2(8) | C(13)—C(14)—H(14A) | 109.5 |
| C(8)—C(7)—C(6) | 109.3(13) | N(2)—C(14)—H(14B) | 109.5 |
| C(12)—C(7)—C(6) | 135.5(15) | C(13)—C(14)—H(14B) | 109.5 |
| C(8)—C(7)—C(6') | 136.3(13) | H(14A)—C(14)—H(14B) | 108.1 |
| C(12)—C(7)—C(6') | 108.4(14) | N(2)—C(15)—C(16) | 110.4(6) |
| C(7)—C(8)—C(9) | 124.1(12) | N(2)—C(15)—H(15A) | 109.6 |
| C(7)—C(8)—H(8A) | 118.0 | C(16)—C(15)—H(15A) | 109.6 |
| C(9)—C(8)—H(8A) | 118.0 | N(2)—C(15)—H(15B) | 109.6 |
| C(8)—C(9)—C(10) | 120.2(13) | C(16)—C(15)—H(15B) | 109.6 |
| C(8)—C(9)—H(9A) | 119.9 | H(15A)—C(15)—H(15B) | 108.1 |
| C(10)—C(9)—H(9A) | 119.9 | N(1)—C(16)—C(15) | 112.1(7) |
| C(9)—C(10)—C(11) | 117.3(8) | N(1)—C(16)—H(16A) | 109.2 |
| C(9)—C(10)—N(1) | 121.7(10) | C(15)—C(16)—H(16A) | 109.2 |
| N(1)—C(16)—H(16B) | 109.2 | N(3)—C(21)—H(21A) | 110.4 |
| C(15)—C(16)—H(16B) | 109.2 | C(22)—C(21)—H(21A) | 110.4 |
| H(16A)—C(16)—H(16B) | 107.9 | N(3)—C(21)—H(21B) | 110.4 |
| C(18)—C(17)—N(2) | 115.7(5) | C(22)—C(21)—H(21B) | 110.4 |
| C(18)—C(17)—H(17A) | 108.4 | H(21A)—C(21)—H(21B) | 108.6 |
| N(2)—C(17)—H(17A) | 108.4 | N(4)—C(22)—C(21) | 110(2) |
| C(18)—C(17)—H(17B) | 108.4 | N(4)—C(22)—C(23) | 106.8(16) |
| N(2)—C(17)—H(17B) | 108.4 | C(21)—C(22)—C(23) | 105(2) |
| H(17A)—C(17)—H(17B) | 107.4 | N(4)—C(22)—H(22A) | 111.7 |
| C(17)—C(18)—C(20) | 114.1(6) | C(21)—C(22)—H(22A) | 111.7 |
| C(17)—C(18)—C(19) | 108.2(6) | C(23)—C(22)—H(22A) | 111.7 |
| C(20)—C(18)—C(19) | 110.6(6) | C(24)—C(23)—C(22) | 108.9(13) |
| C(17)—C(18)—H(18A) | 107.9 | C(24)—C(23)—H(23A) | 109.9 |
| C(20)—C(18)—H(18A) | 107.9 | C(22)—C(23)—H(23A) | 109.9 |
| C(19)—C(18)—H(18A) | 107.9 | C(24)—C(23)—H(23B) | 109.9 |
| C(18)—C(19)—H(19A) | 109.5 | C(22)—C(23)—H(23B) | 109.9 |
| C(18)—C(19)—H(19B) | 109.5 | H(23A)—C(23)—H(23B) | 108.3 |
| H(19A)—C(19)—H(19B) | 109.5 | C(23)—C(24)—C(25) | 112.6(13) |
| C(18)—C(19)—H(19C) | 109.5 | C(23)—C(24)—H(24A) | 109.1 |
| H(19A)—C(19)—H(19C) | 109.5 | C(25)—C(24)—H(24A) | 109.1 |
| H(19B)—C(19)—H(19C) | 109.5 | C(23)—C(24)—H(24B) | 109.1 |
| C(18)—C(20)—H(20A) | 109.5 | C(25)—C(24)—H(24B) | 109.1 |
| C(18)—C(20)—H(20B) | 109.5 | H(24A)—C(24)—H(24B) | 107.8 |
| H(20A)—C(20)—H(20B) | 109.5 | N(3)—C(25)—C(24) | 107.3(15) |
| C(18)—C(20)—H(20C) | 109.5 | N(3)—C(25)—H(25A) | 110.3 |
| H(20A)—C(20)—H(20C) | 109.5 | C(24)—C(25)—H(25A) | 110.3 |
| H(20B)—C(20)—H(20C) | 109.5 | N(3)—C(25)—H(25B) | 110.3 |
| N(3)—C(21)—C(22) | 106(3) | C(24)—C(25)—H(25B) | 110.3 |
| H(25A)—C(25)—H(25B) | 108.5 | C(3')—C(4')—C(5') | 114.4(13) |
| N(4)—C(26)—C(27) | 107.8(18) | C(3')—C(4')—H(4B) | 122.8 |
| N(4)—C(26)—C(30) | 124(2) | C(5')—C(4')—H(4B) | 122.8 |
| C(27)—C(26)—C(30) | 127.8(16) | C(4')—C(5')—C(6') | 125.3(14) |
| C(28)—C(27)—C(26) | 102.7(18) | C(4')—C(5')—H(5B) | 117.3 |
| C(28)—C(27)—C(29) | 133(2) | C(6')—C(5')—H(5B) | 117.3 |
| C(26)—C(27)—C(29) | 124.0(19) | C(5')—C(6')—C(1') | 116.2(16) |
| C(27)—C(28)—N(5) | 112.9(19) | C(5')—C(6')—C(7) | 109.8(15) |
| C(27)—C(28)—H(28A) | 123.6 | C(1')—C(6')—C(7) | 131.7(15) |
| N(5)—C(28)—H(28A) | 123.6 | N(3')—C(21')—C(22') | 109(2) |
| O(1)—C(29)—O(2) | 123(2) | N(3')—C(21')—H(21C) | 109.9 |
| O(1)—C(29)—C(27) | 125.0(19) | C(22')—C(21')—H(21C) | 109.9 |
| O(2)—C(29)—C(27) | 112(2) | N(3')—C(21')—H(21D) | 109.9 |
| F(2)—C(30)—F(1) | 104.4(13) | C(22')—C(21')—H(21D) | 109.9 |
| F(2)—C(30)—C(26) | 112.1(18) | H(21C)—C(21')—H(21D) | 108.3 |
| F(1)—C(30)—C(26) | 110.6(17) | N(4')—C(22')—C(23') | 108.7(16) |
| F(2)—C(30)—H(30A) | 109.9 | N(4')—C(22')—C(21') | 111.0(16) |
| F(1)—C(30)—H(30A) | 109.9 | C(23')—C(22')—C(21') | 117.6(19) |
| C(26)—C(30)—H(30A) | 109.9 | N(4')—C(22')—H(22B) | 106.3 |
| N(3')—C(1')—C(2') | 119.2(17) | C(23')—C(22')—H(22B) | 106.3 |
| N(3')—C(1')—C(6') | 120.3(18) | C(21')—C(22')—H(22B) | 106.3 |
| C(2')—C(1')—C(6') | 120(2) | C(22')—C(23')—C(24') | 107.4(15) |
| C(1')—C(2')—C(3') | 118.4(18) | C(22')—C(23')—H(23C) | 110.2 |
| C(1')—C(2')—H(2E) | 120.8 | C(24')—C(23')—H(23C) | 110.2 |
| C(3')—C(2')—H(2E) | 120.8 | C(22')—C(23')—H(23D) | 110.2 |
| C(4')—C(3')—C(2') | 125.1(15) | C(24')—C(23')—H(23D) | 110.2 |
| C(4')—C(3')—Cl(2') | 118.0(12) | H(23C)—C(23')—H(23D) | 108.5 |
| C(2')—C(3')—Cl(2') | 116.8(12) | C(23')—C(24')—C(25') | 114.0(14) |
| C(23')—C(24')—H(24C) | 108.8 | C(28')—C(27')—C(29') | 123.1(17) |

TABLE 2-continued

| Bond lengths [Å] and angles [°] for example 4. | | | |
|---|---|---|---|
| C(25')—C(24')—H(24C) | 108.8 | N(5')—C(28')—C(27') | 110.3(16) |
| C(23')—C(24')—H(24D) | 108.8 | N(5')—C(28')—H(28B) | 124.8 |
| C(25')—C(24')—H(24D) | 108.8 | C(27')—C(28')—H(28B) | 124.8 |
| H(24C)—C(24')—H(24D) | 107.7 | O(1')—C(29')—O(2') | 126.1(19) |
| N(3')—C(25')—C(24') | 106.9(15) | O(1')—C(29')—C(27') | 124.4(16) |
| N(3')—C(25')—H(25C) | 110.3 | O(2')—C(29')—C(27') | 109.4(19) |
| C(24')—C(25')—H(25C) | 110.3 | F(1')—C(30')—F(2') | 107.3(18) |
| N(3')—C(25')—H(25D) | 110.3 | F(1')—C(30')—C(26') | 111.2(19) |
| C(24')—C(25')—H(25D) | 110.3 | F(2')—C(30')—C(26') | 112.0(17) |
| H(25C)—C(25')—H(25D) | 108.6 | F(1')—C(30')—H(30B) | 108.7 |
| C(27')—C(26')—N(4') | 105.4(19) | F(2')—C(30')—H(30B) | 108.7 |
| C(27')—C(26')—C(30') | 134.7(19) | C(26')—C(30')—H(30B) | 108.7 |
| N(4')—C(26')—C(30') | 120(3) | H(1W)—O(1W)—H(1W)#1 | 107.2 |
| C(26')—C(27')—C(28') | 108.0(15) | | |
| C(26')—C(27')—C(29') | 128.4(19) | | |

TABLE 3

| Torsion angles [°] for example 4 | | | |
|---|---|---|---|
| C(26)—N(4)—N(5)—C(28) | 4(2) | C(1)—C(2)—C(3)—C(4) | −7(3) |
| C(22)—N(4)—N(5)—C(28) | −173.4(17) | C(1)—C(2)—C(3)—C1(2) | 178.6(14) |
| C(26')—N(4')—N(5')—C(28') | 0(2) | C(2)—C(3)—C(4)—C(5) | 5(3) |
| C(22')—N(4')—N(5')—C(28') | −157.8(16) | Cl(2)—C(3)—C(4)—C(5) | 178.8(12) |
| C(25)—N(3)—C(1)—C(6) | 148.8(17) | C(3)—C(4)—C(5)—C(6) | −4(2) |
| C(21)—N(3)—C(1)—C(6) | −87(3) | C(2)—C(1)—C(6)—C(5) | −8(3) |
| C(25)—N(3)—C(1)—C(2) | −25(3) | N(3)—C(1)—C(6)—C(5) | 178.0(16) |
| C(21)—N(3)—C(1)—C(2) | 99(3) | C(2)—C(1)—C(6)—C(7) | 169.6(16) |
| C(6)—C(1)—C(2)—C(3) | 9(3) | N(3)—C(1)—C(6)—C(7) | −5(2) |
| N(3)—C(1)—C(2)—C(3) | −177.2(18) | C(4)—C(5)—C(6)—C(1) | 6(2) |
| C(4)—C(5)—C(6)—C(7) | −171.3(14) | C(17)—N(2)—C(15)—C(16) | 176.4(6) |
| C(1)—C(6)—C(7)—C(8) | 148.5(14) | C(10)—N(1)—C(16)—C(15) | −168.9(6) |
| C(5)—C(6)—C(7)—C(8) | −34.4(18) | C(13)—N(1)—C(16)—C(15) | 59.3(7) |
| C(1)—C(6)—C(7)—C(12) | −33.3(19) | N(2)—C(15)—C(16)—N(1) | −58.4(8) |
| C(5)—C(6)—C(7)—C(12) | 143.8(15) | C(14)—N(2)—C(17)—C(18) | 178.4(6) |
| C(12)—C(7)—C(8)—C(9) | 2.5(13) | C(15)—N(2)—C(17)—C(18) | 56.9(8) |
| C(6)—C(7)—C(8)—C(9) | −178.9(9) | N(2)—C(17)—C(18)—C(20) | 58.0(8) |
| C(6')—C(7)—C(8)—C(9) | 178.8(11) | N(2)—C(17)—C(18)—C(19) | −178.5(6) |
| C(7)—C(8)—C(9)—C(10) | −1.1(13) | C(25)—N(3)—C(21)—C(22) | −75(3) |
| C(8)—C(9)—C(10)—C(11) | −1.0(11) | C(1)—N(3)—C(21)—C(22) | 156(2) |
| C(8)—C(9)—C(10)—N(1) | −179.4(7) | C(26)—N(4)—C(22)—C(21) | 131(3) |
| C(16)—N(1)—C(10)—C(9) | −176.9(7) | N(5)—N(4)—C(22)—C(21) | −52(3) |
| C(13)—N(1)—C(10)—C(9) | −46.9(9) | C(26)—N(4)—C(22)—C(23) | −116(2) |
| C(16)—N(1)—C(10)—C(11) | 4.8(10) | N(5)—N(4)—C(22)—C(23) | 61(2) |
| | | N(3)—C(21)—C(22)—N(4) | −177(2) |
| C(13)—N(1)—C(10)—C(11) | 134.9(8) | N(3)—C(21)—C(22)—C(23) | 68(3) |
| C(9)—C(10)—C(11)—C(12) | 1.5(12) | N(4)—C(22)—C(23)—C(24) | −173.8(14) |
| N(1)—C(10)—C(11)—C(12) | 179.9(7) | C(21)—C(22)—C(23)—C(24) | −57(2) |
| C(8)—C(7)—C(12)—C(11) | −1.9(13) | C(22)—C(23)—C(24)—C(25) | 53.5(18) |
| C(6)—C(7)—C(12)—C(11) | 179.9(11) | C(21)—N(3)—C(25)—C(24) | 67(2) |
| C(6')—C(7)—C(12)—C(11) | −179.2(10) | C(1)—N(3)—C(25)—C(24) | −166.6(17) |
| C(10)—C(11)—C(12)—C(7) | 0.0(14) | | |
| C(10)—N(1)—C(13)—C(14) | 167.0(7) | C(23)—C(24)—C(25)—N(3) | −56.8(19) |
| C(16)—N(1)—C(13)—C(14) | −58.8(8) | N(5)—N(4)—C(26)—C(27) | −3(2) |
| C(15)—N(2)—C(14)—C(13) | −55.6(7) | C(22)—N(4)—C(26)—C(27) | 174.2(19) |
| C(17)—N(2)—C(14)—C(13) | −179.3(6) | N(5)—N(4)—C(26)—C(30) | 179.8(15) |
| N(1)—C(13)—C(14)—N(2) | 57.9(8) | C(22)—N(4)—C(26)—C(30) | −3(3) |

TABLE 3-continued

| Torsion angles [°] for example 4 | | | |
|---|---|---|---|
| C(14)—N(2)—C(15)—C(16) | 55.1(8) | N(4)—C(26)—C(27)—C(28) | 1(2) |
| C(30)—C(26)—C(27)—C(28) | 177.7(15) | C(2')—C(1')—C(6')—C(5') | −5(3) |
| N(4)—C(26)—C(27)—C(29) | −175.0(16) | N(3')—C(1')—C(6')—C(7) | 17(3) |
| C(30)—C(26)—C(27)—C(29) | 2(3) | C(2')—C(1')—C(6')—C(7) | −166.3(19) |
| C(26)—C(27)—C(28)—N(5) | 2(2) | C(8)—C(7)—C(6')—C(5') | −39.2(19) |
| C(29)—C(27)—C(28)—N(5) | 176.9(18) | C(12)—C(7)—C(6')—C(5') | 137.2(12) |
| N(4)—N(5)—C(28)—C(27) | −3.6(19) | C(8)—C(7)—C(6')—C(1') | 122.5(19) |
| C(28)—C(27)—C(29)—O(1) | 146.4(19) | C(12)—C(7)—C(6')—C(1') | −61(2) |
| C(26)—C(27)—C(29)—O(1) | −39(3) | C(1')—N(3')—C(21')—C(22') | 168.4(18) |
| C(28)—C(27)—C(29)—O(2) | −31(3) | C(25')—N(3')—C(21')—C(22') | −49(3) |
| C(26)—C(27)—C(29)—O(2) | 143(2) | N(5')—N(4')—C(22')—C(23') | 65(2) |
| N(4)—C(26)—C(30)—F(2) | 53(2) | C(26')—N(4')—C(22')—C(23') | −88(3) |
| C(27)—C(26)—C(30)—F(2) | −124(2) | N(5')—N(4')—C(22')—C(21') | −66(3) |
| N(4)—C(26)—C(30)—F(1) | −63(2) | C(26')—N(4')—C(22')—C(21') | 141(2) |
| C(27)—C(26)—C(30)—F(1) | 120(2) | N(3')—C(21')—C(22')—N(4') | 169.0(19) |
| C(21')—N(3')—C(1')—C(2') | 112(2) | N(3')—C(21')—C(22')—C(23') | 43(3) |
| C(25')—N(3')—C(1')—C(2') | −31(3) | N(4')—C(22')—C(23')—C(24') | −173.4(15) |
| C(21')—N(3')—C(1')—C(6') | −71(2) | C(21')—C(22')—C(23')—C(24') | −46(2) |
| C(25')—N(3')—C(1')—C(6') | 146.4(17) | C(22')—C(23')—C(24')—C(25') | 55(2) |
| N(3')—C(1')—C(2')—C(3') | 180.0(19) | C(1')—N(3')—C(25')—C(24') | −161.9(18) |
| C(6')—C(1')—C(2')—C(3') | 3(3) | C(21')—N(3')—C(25')—C(24') | 58(2) |
| C(1')—C(2')—C(3')—C(4') | 2(3) | C(23')—C(24')—C(25')—N(3') | −59(2) |
| C(1')—C(2')—C(3')—Cl(2') | 179.1(15) | N(5')—N(4')—C(26')—C(27') | −1(2) |
| C(2')—C(3')—C(4')—C(5') | −4(3) | C(22')—N(4')—C(26')—C(27') | 154(2) |
| Cl(2')—C(3')—C(4')—C(5') | 179.0(12) | N(5')—N(4')—C(26')—C(30') | −176.3(16) |
| C(3')—C(4')—C(5')—C(6') | 1(2) | C(22')—N(4')—C(26')—C(30') | −21(3) |
| C(4')—C(5')—C(6')—C(1') | 4(3) | N(4')—C(26')—C(27')—C(28') | 1.2(19) |
| C(4')—C(5')—C(6')—C(7) | 168.4(15) | C(30')—C(26')—C(27')—C(28') | 175.6(19) |
| N(3')—C(1')—C(6')—C(5') | 177.6(19) | N(4')—C(26')—C(27')—C(29') | −171.1(16) |
| C(30')—C(26')—C(27')—C(29') | 3(3) | C(26')—C(27')—C(29')—O(2') | −21(2) |
| N(4')—N(5')—C(28')—C(27') | 1(2) | C(28')—C(27')—C(29')—O(2') | 167.6(16) |
| C(26')—C(27')—C(28')—N(5') | −1(2) | C(27')—C(26')—C(30')—F(1') | 132(2) |
| C(29')—C(27')—C(28')—N(5') | 171.6(15) | N(4')—C(26')—C(30')—F(1') | −54(2) |
| C(26')—C(27')—C(29')—O(1') | 162.9(18) | C(27')—C(26')—C(30')—F(2') | −108(2) |
| C(28')—C(27')—C(29')—O(1') | −8(3) | N(4')—C(26')—C(30')—F(2') | 66(2) |

Symmetry transformation used to generate equivalent atoms: # 1 y − 1, x + 1, −z + 1

TABLE 4

Hydrogen bonds for example 4 [Å and °].

| D—H | d(D—H) | d(H . . . A) | <DHA | d(D . . . A) | A |
|---|---|---|---|---|---|
| O2^a—H2A^a | 0.840 | 2.268 | 171.52 | 3.102 | Cl1 [x + 1, y − 1, z] |
| O2'^b—H2B^b | 0.840 | 2.219 | 158.79 | 3.018 | Cl1 [x + 1, y − 1, z] |
| N2—H2C | 1.000 | 2.158 | 162.74 | 3.128 | Cl1 [y, x, −z + 1] |
| O1W—H1W | 0.901 | 2.448 | 164.20 | 3.324 | Cl1 |

The patent or application file contains at least one drawing executed in color. Copies of this patent or patent application publication with color drawing(s) will be provided by the Office upon request and payment of the necessary fee.

FIG. 1 shows an Ortep-Plot (50%) with labeling scheme (without disorder), as defined in example 4.

FIG. 2 shows independent molecules in the asymmetric unit (with disorder), as defined in example 4.

FIG. 3 shows the configuration of C22, as defined in example 4.

COMPARATIVE EXAMPLE 174 (WO2012/058132)

1-{1-[4-Chloro-4'-(4-cyclopropylmethylpiperazin-1-yl)[biphenyl]-2-yl]pyridin-3-yl}-5-(trifluoromethyl)-1H-pyrazole-4-carboxylic acid

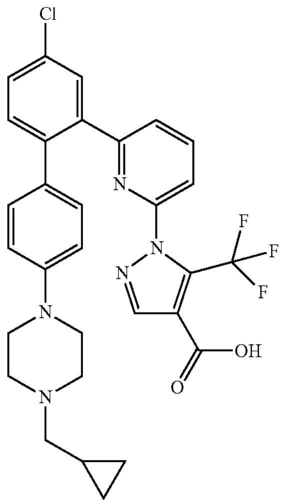 [SMILES: O=C(O)c1cnn(-c2cccc(-c3cc(Cl)ccc3-c3ccc(N4CCN(CC5CC5)CC4)cc3)n2)c1C(F)(F)F]

The compound was synthesized according to the procedures disclosed in WO 2012/058132 (experimental part, pages 58 to 84).

B. Assessment of Pharmacological Efficacy and Pharmacokinetic Profile

The following abbreviations are used:

ATP adenosine triphosphate

Brij35 polyoxyethylene(23) lauryl ether

BSA bovine serum albumin:

DTT dithiothreitol

TEA triethanolamine

Biological Investigations

The example testing experiments described herein serve to illustrate the present invention and the invention is not limited to the examples given.

The following assays can be used to illustrate the commercial utility of the compounds according to the present invention.

Examples were tested in selected biological assays one or more times. When tested more than once, data are is reported as either average values or as median values, wherein the average value, also referred to as the arithmetic mean value, represents the sum of the values obtained divided by the number of times tested, and the median value represents the middle number of the group of values when ranked in ascending or descending order. If the number of values in the data set is odd, the median is the middle value. If the number of values in the data set is even, the median is the arithmetic mean of the two middle values.

Examples were synthesized one or more times. When synthesized more than once, data from biological assays represent average values calculated utilizing data sets obtained from testing of one or more synthetic batch.

The in vitro activity of the compounds of the present invention can be demonstrated in the following assays.

The pharmacological action of the compounds of the invention can be demonstrated in the following assays:

B-1. Effect on a Recombinant Guanylate Cyclase Reporter Cell Line

The cellular activity of the compounds according to the invention was determined using a recombinant guanylate cyclase reporter cell line, as described in F. Wunder et al., *Anal. Biochem.* 339, 104-112 (2005).

Representative MEC values (MEC=minimum effective concentration) and $EC_{50}$ values (half maximal effective concentration) for the compounds of the invention are shown in the table below (in some cases as mean values from individual determinations):

TABLE 2

| Example | MEC [nM] | $EC_{50}$ [nM] |
|---|---|---|
| 1 | 2.3 | 9.2 |
| 2 | 1.0 | 8.6 |
| 3 | 0.6 | 2.7 |

B-2. Vasorelaxant Effect In Vitro

Rabbits were killed in deep anaesthesia and exsanguinated. The aorta was removed, freed from adhering tissue and divided into rings of width 1.5 mm, which were placed individually under prestress into 5 ml organ baths with carbogen-sparged Krebs-Henseleit solution at 37° C. having the following composition (each in mM): sodium chloride: 119; potassium chloride: 4.8; calcium chloride dihydrate: 1; magnesium sulfate heptahydrate: 1.4; potassium dihydrogenphosphate: 1.2; sodium bicarbonate: 25; glucose: 10. To generate a contraction, phenylephrine was added to the bath cumulatively in increasing concentration. After several control cycles, the substance to be studied was added in increasing dosage each time in every further run, and the magnitude of the contraction was compared with the magnitude of the contraction attained in the last preceding run. This was used to calculate the concentration needed to reduce the magnitude of the control value by 50% ($IC_{50}$ value). The standard administration volume was 5 μl; the DMSO content in the bath solution corresponds to 0.1%.

B-3. Blood Pressure Measurement on Anaesthetized Rats

Male Wistar rats having a body weight of 300-350 g were anaesthetized with thiopental (100 mg/kg i.p.).

After tracheotomy, a catheter was introduced into the femoral artery to measure the blood pressure. The substances to be tested were administered as solutions, either orally by means of a gavage or intravenously via the femoral vein (Stasch et al. Br. J. Pharmacol. 2002; 135: 344-355).

B-4. Radiotelemetry Measurement of Blood Pressure in Conscious, Spontaneously Hypertensive Rats A commercially available telemetry system from DATA SCIENCES INTERNATIONAL DSI, USA, was employed for the blood pressure measurement on conscious rats described below.

The system consists of 3 main components:

implantable transmitters (Physiotel® telemetry transmitter)

receivers (Physiotel® receiver) which are linked via a multiplexer (DSI Data Exchange Matrix 2.0) to a data acquisition computer.

The telemetry system makes it possible to continuously record blood pressure, heart rate and body motion of conscious animals in their usual habitat.

Animal Material

The studies were conducted on adult female spontaneously hypertensive rats (SHR Okamoto) with a body weight of >200 g. SHR/NCrl from the Okamoto Kyoto School of Medicine, 1963, were a cross of male Wistar Kyoto rats having greatly elevated blood pressure and female rats having slightly elevated blood pressure, and were handed over at F13 to the U.S. National Institutes of Health.

After transmitter implantation, the experimental animals were housed singly in type 3 Makrolon cages. They had free access to standard feed and water.

The day/night rhythm in the experimental laboratory was changed by the room lighting at 6:00 am and at 7:00 pm.

Transmitter Implantation

The HD S 10 telemetry transmitters used were surgically implanted under aseptic conditions in the experimental animals at least 14 days before the first experimental use. The animals instrumented in this way can be used repeatedly after the wound has healed and the implant has settled.

For the implantation, the fasted animals were anesthetized with isoflurane (Rimadyl analgesia) and shaved and disinfected over a large area of their abdomens. After the abdominal cavity had been opened along the linea alba, the liquid-filled measuring catheter of the system was inserted into the descending aorta in the cranial direction above the bifurcation and fixed with tissue glue (VetBonD™, 3M). The transmitter housing was fixed intraperitoneally to the abdominal wall muscle, and the wound was closed layer by layer.

An antibiotic (Ursocyclin 10% pro inj., Serumwerk, s.c.) was administered postoperatively for prophylaxis of infection.

Substances and solutions Unless stated otherwise, the substances to be studied were administered orally by gavage to a group of animals in each case (n=6). In accordance with an administration volume of 2 ml/kg of body weight, the test substances were dissolved in suitable solvent mixtures or suspended in 0.5% tylose.

A solvent-treated group of animals was used as control.

Experimental Procedure

The telemetry measuring unit present was configured for 24 animals. Each experiment was recorded under an experiment number (year month day).

Each of the instrumented rats living in the system was assigned a separate receiving antenna (RPC-1 Receiver, DSI).

The implanted transmitters can be activated externally by means of an incorporated magnetic switch. They were switched to transmission in the run-up to the experiment. The signals emitted could be detected online by a data acquisition system (Physio Tel HD, DSI) and processed accordingly. The data were stored in each case in a file created for this purpose and bearing the experiment number.

In the standard procedure, the following were measured for 10-second periods in each case:

systolic blood pressure (SBP)
diastolic blood pressure (DBP)
mean arterial pressure (MAP)
heart rate (HR)
activity (TEMP).

The acquisition of measurements was repeated under computer control at 5-minute intervals. The source data obtained as absolute values were corrected in the diagram with the currently measured barometric pressure (Ambient Pressure Reference Monitor; APR-1) and stored as individual data. Further technical details is given in the extensive documentation from the manufacturer company (DSI).

Unless indicated otherwise, the test substances were administered at 9:00 am on the day of the experiment.

Following the administration, the parameters described above were measured over 24 hours.

Evaluation

After the end of the experiment, the acquired individual data were sorted using the analysis software (Ponemah V 6.x). The blank value was assumed here to be the time 2 hours before administration, and so the selected data set encompasses the period from 7:00 am on the day of the experiment to 9:00 am on the following day.

The data were smoothed over a predefinable period by determination of the average (30-minute average) and transferred as an excel file to a storage medium. The measured values presorted and compressed in this way were transferred to Excel templates and tabulated. For each day of the experiment, the data obtained were stored in a dedicated file bearing the number of the experiment. Results and test protocols were stored in files in paper form sorted by numbers.

LITERATURE

Klaus Witte, Kai Hu, Johanna Swiatek, Claudia Müssig, Georg Ertl and Björn Lemmer: Experimental heart failure in rats: effects on cardiovascular circadian rhythms and on myocardial β-adrenergic signaling. Cardiovasc Res 47 (2): 203-405, 2000; Kozo Okamoto: Spontaneous hypertension in rats. Int Rev Exp Pathol 7: 227-270, 1969; Maarten van den Buuse: Circadian Rhythms of Blood Pressure, Heart Rate, and Locomotor Activity in Spontaneously Hypertensive Rats as Measured With Radio-Telemetry. Physiology & Behavior 55(4): 783-787, 1994.

B-5. Determination of Pharmacokinetic Parameters Following Intravenous and Oral Administration The pharmacokinetic parameters of the compounds according to the invention were determined in male Wistar rats and and/or in female beagles and/or in cynomolgus monkeys and/or in male CD-1 mice. Intravenous administration in the case of mice and rats was carried out by means of a species-specific plasma/DMSO formulation, and in the case of dogs and monkeys by means of a water/PEG400/ethanol formulation. In all species, oral administration of the dissolved substance was performed via gavage, based on a water/PEG400/ethanol formulation.

An internal standard (which may also be a chemically unrelated substance) was added to the samples of the compounds of the invention, calibration samples and qualifiers, and there followed protein precipitation by means of acetonitrile in excess. Addition of a buffer solution matched to the LC conditions, and subsequent vortexing, was followed by centrifugation at 1000 g. The supernatant was analysed by LC-MS/MS using C18 reversed-phase columns and variable mobile phase mixtures. The substances were quantified via the peak heights or areas from extracted ion chromatograms of specific selected ion monitoring experiments.

The plasma concentration/time plots determined were used to calculate the pharmacokinetic parameters such as AUC, $C_{max}$, $t_{1/2}$ (terminal half-life), F (bioavailability), MRT (mean residence time) and CL (clearance), by means of a validated pharmacokinetic calculation program.

Since the substance quantification was performed in plasma, it was necessary to determine the blood/plasma distribution of the substance in order to be able to adjust the pharmacokinetic parameters correspondingly.

For this purpose, a defined amount of substance was incubated in K3 EDTA whole blood of the species in question in a rocking roller mixer for 20 min. After centrifugation at 1000 g, the plasma concentration was measured (by means of LC-MS/MS; see above) and determined by calculating the ratio of the $C_{blood}/C_{plasma}$ value.

Table 3 shows data of representative compounds of the present invention following intravenous administration in rats:

TABLE 3

| Example | $AUC_{norm}$ [kg · h/L] | $CL_{plasma}$ [L/h/kg] | $t_{1/2}$ [h] | MRT [h] |
|---|---|---|---|---|
| 1 | 1.77 | 0.56 | 1.64 | 2.24 |
| 2 | 7.08 | 0.14 | 3.13 | 3.44 |
| 174 (WO2012/058132) | 0.77 | 1.30 | 2.33 | 2.78 |

Table 4 shows data of representative compounds of the present invention following oral administration (p.o.) in rats:

TABLE 4

| Example | $AUC_{norm}$ [kg · h/L] | $t_{1/2}$ [h] | MRT [h] | F [%] |
|---|---|---|---|---|
| 1 | 0.57 | 3.24 | 6.28 | 31.4 |
| 2 | 3.77 | 3.96 | 6.23 | 53.3 |
| 174 (WO2012/058132) | 0.63 | 3.60 | 8.40 | 81.8 |

Table 5 shows data of representative compounds of the present invention following intravenous administration in dogs:

TABLE 5

| Example | $AUC_{norm}$ [kg · h/L] | $CL_{plasma}$ [L/h/kg] | $t_{1/2}$ [h] | MRT [h] |
|---|---|---|---|---|
| 2 | 81.7 | 0.01 | 17.7 | 25.6 |
| 174 (WO2012/058132) | 5.00 | 0.20 | 10.8 | 7.23 |

Table 6 shows data of representative compounds of the present invention following oral administration (p.o.) in dogs:

TABLE 6

| Example | $AUC_{norm}$ [kg · h/L] | $t_{1/2}$ [h] | MRT [h] | F [%] |
|---|---|---|---|---|
| 2 | 67.7 | 14.0 | 21.3 | 82.8 |
| 174 (WO2012/058132) | 2.08 | 7.05 | 6.10 | 41.6 |

The compounds according to the present invention show superior pharmacokinetic (PK) properties in comparison to compounds disclosed in the prior art (WO 2012/058132) (see tables 3 to 6). For instance example 2 of the present invention shows a lower plasma clearance ($CL_{plasma}$) (up to 10 times) and therefore a much higher exposure in comparison to the prior art compound disclosed as example 174 in WO 2012/058132 in rats as well as in dogs. Example 2 shows also a long half-life and mean residence time (MRT) in all tested species after p.o. (per oral) application. Due to the significantly lower plasma clearance of example 2 and the resulting very high exposure ($AUC_{norm}$, exposure, area under curve normated) with good bioavailability after p.o. application in all tested species, we see a clear superiority of pharmacokinetic (PK) properties versus example 174 disclosed in WO 2012/058132.

B-6. Metabolic Study

To determine the metabolic profile of the inventive compounds, they were incubated with recombinant human cytochrome P450 (CYP) enzymes, liver microsomes or primary fresh hepatocytes from various animal species (e.g. rats, dogs), and also of human origin, in order to obtain and to compare information about a very substantially complete hepatic phase I and phase II metabolism, and about the enzymes involved in the metabolism.

The compounds of the invention were incubated with a concentration of about 0.1-10 μM. To this end, stock solutions of the compounds of the invention having a concentration of 0.01-1 mM in acetonitrile were prepared, and then pipetted with a 1:100 dilution into the incubation mixture. The liver microsomes and recombinant enzymes were incubated at 37° C. in 50 mM potassium phosphate buffer pH 7.4 with and without NADPH-generating system consisting of 1 mM $NADP^+$, 10 mM glucose-6-phosphate and 1 unit glucose-6-phosphate dehydrogenase. Primary hepatocytes were incubated in suspension in Williams E medium, likewise at 37° C. After an incubation time of 0-4 h, the incubation mixtures were stopped with acetonitrile (final concentration about 30%) and the protein was centrifuged off at about 15 000×g. The samples thus stopped were either analyzed directly or stored at −20° C. until analysis.

The analysis was carried out by high-performance liquid chromatography with ultraviolet and mass spectrometry detection (HPLC-UV-MS/MS). To this end, the supernatants of the incubation samples were chromatographed with suitable C18 reversed-phase columns and variable mobile phase mixtures of acetonitrile and 10 mM aqueous ammonium formate solution or 0.05% formic acid. The UV chromatograms in conjunction with mass spectrometry data serve for identification, structural elucidation and quantitative estimation of the metabolites, and for quantitative metabolic reduction of the compound of the invention in the incubation mixtures.

B-7. Caco-2 Permeability Test

The permeability of a test substance was determined with the aid of the Caco-2 cell line, an established in vitro model for permeability prediction at the gastrointestinal barrier (Artursson, P. and Karlsson, J. (1991). Correlation between oral drug absorption in humans and apparent drug permeability coefficients in human intestinal epithelial (Caco-2) cells. Biochem. Biophys. 175 (3), 880-885). The Caco-2 cells (ACC No. 169, DSMZ, Deutsche Sammlung von Mikroorganismen und Zellkulturen, Braunschweig, Germany) were sown in 24-well plates having an insert and cultivated for 14 to 16 days. For the permeability studies, the test substance was dissolved in DMSO and diluted to the final test concentration with transport buffer (Hanks Buffered Salt Solution, Gibco/Invitrogen, with 19.9 mM glucose and 9.8 mM HEPES). In order to determine the apical to basolateral permeability ($P_{app}$A-B) of the test substance, the solution comprising the test substance was applied to the apical side of the Caco-2 cell monolayer, and transport buffer to the basolateral side. In order to determine the basolateral to apical permeability ($P_{app}$B-A) of the test substance, the solution comprising the test substance was applied to the basolateral side of the Caco-2 cell monolayer, and transport buffer to the apical side. At the start of the experiment, samples were taken from the respective donor compartment in order to ensure the mass balance. After an incubation time of two hours at 37° C., samples were taken from the two compartments. The samples were analyzed by means of LC-MS/MS and the apparent permeability coefficients ($P_{app}$) were calculated. For each cell monolayer, the permeability of Lucifer Yellow was determined to ensure cell layer integrity. In each test run, the permeability of atenolol (marker for low permeability) and sulfasalazine (marker for active excretion) was also determined as quality control.

B-8. Solubility Determination of Substances in Buffer pH 6.5

2-4 mg of the test compound were dissolved in DMSO to reach a concentration of 50 g/L (solution A, 515 μg/l). To 10 μl of this solution 960 μl PBS buffer pH 6.5 were added; the mixture was shaken for 24 h at rt is in a 96 well plate. An aliquot was centrifuged at 42000 rpm for 30 min. The supernatant was diluted with ACN/water (8:2) 1:10 and 1:1000 resp. This diluted samples were analyzed by LC-MSMS.

Calibration: 10 μl of solution A were diluted with 823 μl DMSO (final concentration: 600 μg/ml), which was further diluted with ACN/water 8:2 by a factor of 100 (solution B).

The calibration curve was obtained from solution B by further diluting with ACN/water 8:2 with target concentrations of 1.2-12-60-600 ng/ml and injecting these four solutions for MS measurement.

MS Method Optimization:

Solution B was utilized for MS method optimization.

PBS-Puffer: 6.18 g sodium chloride and 3.96 g sodium dihydrogen phosphate were dissolved in 1 L aqua dist., the pH was adjusted to 6.5 with 1N sodium hydroxide.

Lc-Msms Optimization:

The following configurations were used for optimization

AB Sciex TRIPLE QUAD 4500, Agilent 1260 Infinity (G1312B), degasser (G4225A), column oven (G1316C or G1316A), CTC Analytics PAL injection system HTS-xt or HTC-xt.

Eluent A: 0.5 ml formic acid (50% ig)/L water, Eluent B: 0.5 ml formic acid (50% ig)/L acetonitrile

| time [min] | flow [μl/min] | % B |
|---|---|---|
| 0.00 | 200 | 70 |
| 0.08 | 200 | 70 |
| 0.09 | 25 | 70 |
| 0.60 | 25 | 70 |
| 0.65 | 200 | 70 |
| 1.10 | 200 | 70 |

Autosampler: without auto inject ahead setting
column: stainless steel capillary
oven temperature: 22° C.
flow rate: flow gradient
injected volume: 2 μl Water Quattro Micro MS, Agilent 1100 (G1312A), degasser (G1322A), column oven (G1316A), CTC Analytics PAL injection system HTS, eluents as above

| time [min] | flow [μl/min] | % B |
|---|---|---|
| 0.00 | 250 | 70 |
| 1.50 | 250 | 70 |

Autosampler: with auto inject ahead setting
column: stainless steel capillary
oven temperature: 22° C.
flow rate: flow gradient
injected volume: 5 μl
MS method: Flow Injection Analysis (FIA) for optimization ("MS-OPTI");

Ionization mode ABSciex-MS: ESI-pos/neg, Waters-MS: ESI-pos

HPLC Method for MSMS Quantification:

Eluent A, B as above

ABSciex-MS

| time [min] | % A | % B |
|---|---|---|
| 0 | 90 | 10 |
| 0.5 | 5 | 95 |
| 0.84 | 5 | 95 |
| 0.85 | 90 | 10 |
| 1.22 | 90 | 10 |

Autosampler: without auto inject ahead setting
column: Waters OASIS HLB, 2.1×20 mm, 25 g
column temperature: 30° C.
flow rate: 2.5 ml
injected volume: 2 μl
Splitter (before MS) 1:20
Waters-MS

| time [min] | % A | % B |
|---|---|---|
| 0 | 90 | 10 |
| 0.5 | 5 | 95 |
| 0.84 | 5 | 95 |
| 0.85 | 90 | 10 |
| 1.5 | 90 | 10 |

Autosampler: with auto inject ahead setting
column: Waters OASIS HLB, 2.1×20 mm, 25μ
column temperature: 30° C.
flow rate: 2.5 ml
injected volume: 5 μl
Splitter (before MS) 1:20
MS method: Multiple Reaction Monitoring (MRM)

B-9. Determination of Solubility from Solid

For each solvent, an Eppendorf plastic vial was charged with 0.5-1 mg of the test compound (exact weight), 2-3 μlass pearls (diameter 3 mm) and 1.0 ml of the respective solvent. The vial was closed and shaken at RT for 24 h (1400 rpm; Thermomixer, Eppendorf). Thereafter, 230 μl each of the solution/suspension was transferred into one or more centrifuge vials (Beckman Coulter) and were centrifuged at 42000 rpm for 30 min (Beckman Coulter Optima L90). At least 100 μl of the supernatant were withdrawn and further diluted with DMSO in two dilution strength: 1:5 and 1:50 (the latter obtained from the 1:5 dilution step by subsequent DMSO addition). This liquid handling was done either manually or with the help of a pipetting robot (Lissy, Zinsser Analytic).

For HPLC quantification, calibration solutions of the test compound in DMSO were prepared. Starting from an initial concentration of 600 μg/ml, three calibration solutions were prepared: 100 μg/ml, 20 μg/ml and 2.5 μg/ml (manually or via Lissy).

Both calibration solutions and the supernatant were analyzed by HPLC/UV-detection at an appropriate wave length. The solubility was determined using the linear calibration curve.

HPLC Systems:

Hewlett Packard/Agilent HPLC systems, G1311A+G1316A+G1315B as well as G1312A+G1316A+G1315A injector system: CTC-Analytik HTC PAL or with a Agilent UPLC Sy stem (G7117C, G7116B, G7167B and G7120)

oven temperature: 30° C., detection: 210 and/or 254 n, injected volume: 20 μl eluent A: 0.1% TFA in water, eluent B: 0.1% TFA in acetonitrile column: ZORBAX Extend-C18, 3.0x50 mm, 3.5 μm Gradient:

| time [min] | A [%] | B [%] | Flow rate: [ml/min] |
|---|---|---|---|
| 0.0 | 98 | 2 | 1.5 |
| 0.2 | 98 | 2 | 1.5 |
| 3.3 | 10 | 90 | 1.5 |
| 4.0 | 10 | 90 | 1.5 |
| 4.1 | 98 | 2 | 2.5 |
| 4.7 | 98 | 2 | 2.5 |
| 5.0 | 98 | 2 | 1.5 |

C. Working Examples of Pharmaceutical Compositions

The compounds of the invention can be converted to pharmaceutical preparations as follows:

Tablet:

Composition:

100 mg of the compound according to the invention, 50 mg of lactose (monohydrate), 50 mg of corn starch (native), 10 mg of polyvinylpyrrolidone (PVP 25) (from BASF, Ludwigshafen, Germany) and 2 mg of magnesium stearate.

Tablet weight 212 mg. Diameter 8 mm, radius of curvature 12 mm.

Production:

The mixture of compound of the invention, lactose and starch is granulated with a 5% solution (w/w) of the PVP in water. The granules are dried and then mixed with the magnesium stearate for 5 minutes. This mixture is compressed using a conventional tableting press (see above for format of the tablet). The guide value used for the pressing is a pressing force of 15 kN.

Suspension for Oral Administration:

Composition:

1000 mg of the compound of the invention, 1000 mg of ethanol (96%), 400 mg of Rhodigel® (xanthan gum from FMC, Pennsylvania, USA) and 99 g of water.

10 ml of oral suspension correspond to a single dose of 100 mg of the compound of the invention.

Production:

The Rhodigel is suspended in ethanol; the compound of the invention is added to the suspension. The water is added while stirring. The mixture is stirred for about 6 h until the swelling of the Rhodigel is complete.

Solution for Oral Administration:

Composition:

500 mg of the compound of the invention, 2.5 g of polysorbate and 97 g of polyethylene glycol 400. 20 g of oral solution correspond to a single dose of 100 mg of the compound of the invention.

Production:

The compound of the invention is suspended in the mixture of polyethylene glycol and polysorbate with stirring. The stirring process is continued until the compound according to the invention has completely dissolved.

i.v. Solution:

The compound according to the invention is dissolved in a concentration below the saturation solubility in a physiologically tolerated solvent (e.g. isotonic saline, 5% glucose solution and/or 30% PEG 400 solution). The solution is sterilized by filtration and used to fill sterile and pyrogen-free injection containers.

The invention claimed is:

1. A process for preparing a compound of the formula (I) or salts thereof, solvates thereof or solvates of the salts thereof, characterized in that in a first step [D] compounds of formula (VIII)

(VIII)

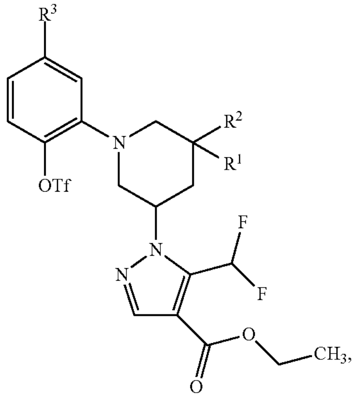

in which $R^1$ represents hydrogen or halogen, $R^2$ represents hydrogen or halogen, and $R^3$ represents chloro or trifluoromethyl, are reacted with compounds of formula (VII)

(VII)

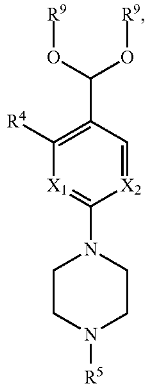

in which $R^4$ represents hydrogen or $C_1$-$C_4$-alkyl, $R^5$ represents $C_1$-$C_6$-alkyl, $R^9$ represents hydrogen, methyl or both or both $R^9$ groups combine to form via the adjacent oxygen atoms a 4,4,5,5-tetramethyl-1,3,2-dioxaborolan, $X_1$ represents nitrogen or carbon, and $X_2$ represents nitrogen or carbon, in the presence of a palladium source, a suitable ligand and a base to provide compounds of formula (II)

(II)

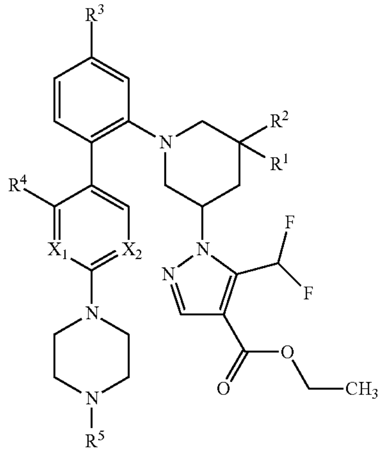

in which $R^1$, $R^2$, $R^3$, $R^4$, $R^5$ and $X_1$ and $X_2$ are defined as above and in a second step [A]

compounds of formula (II)

(II)

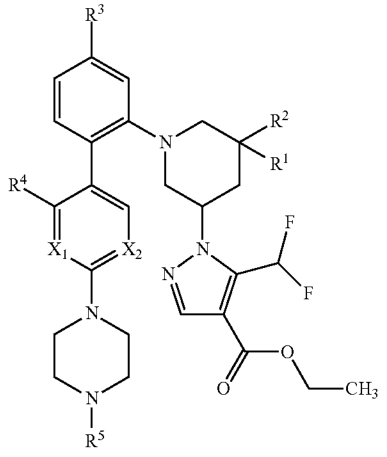

are reacted with a base in a suitable solvent to provide compounds of formula (I), (I)

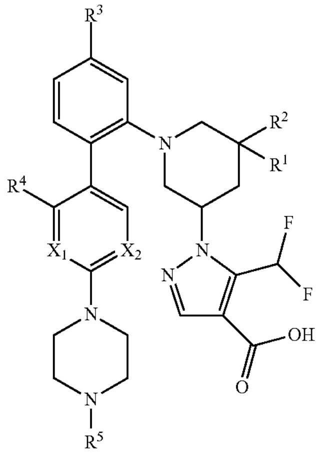

in which $R^1$, $R^2$, $R^3$, $R^4$, $R^5$ and $X_1$ and $X_2$ are defined as above, and optionally compounds of formula (I) are transferred in a third step [A] * into the corresponding salts of formula (Ia)

(Ia)

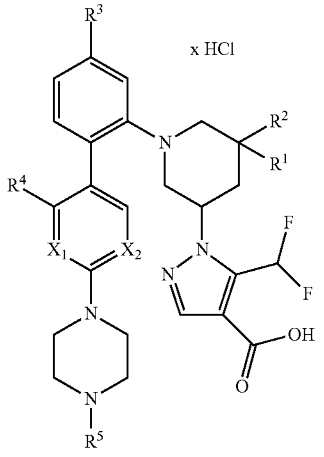

in the presence of a suitable acid in a suitable solvent.

2. A compound according to formula (I)

(I)

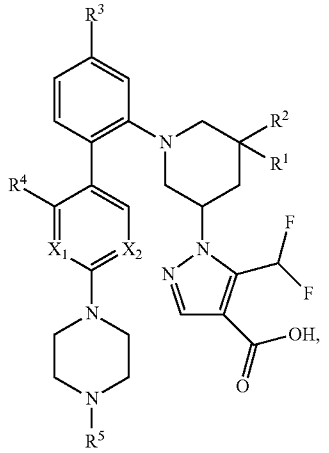

in which $R^1$ represents hydrogen or halogen, $R^2$ represents hydrogen or halogen, $R^3$ represents chloro or trifluoromethyl, $R^4$ represents hydrogen or $C_1$-$C_4$-alkyl, $R^5$ represents $C_1$-$C_6$-alkyl, $X_1$ represents nitrogen or carbon, and $X_2$ represents nitrogen or carbon, or a salt thereof, solvates thereof or solvates of the salts thereof for use in the treatment and/or prophylaxis of diseases.

3. A compound according to formula (I)

(I)

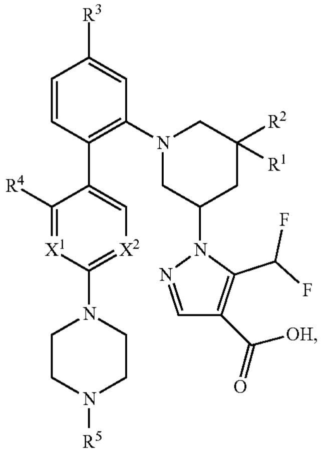

in which $R^1$ represents hydrogen or halogen, $R^2$ represents hydrogen or halogen, $R^3$ represents chloro or trifluoromethyl, $R^4$ represents hydrogen or $C_1$-$C_4$-alkyl, $R^5$ represents $C_1$-$C_6$-alkyl, $X_1$ represents nitrogen or carbon, and $X_2$ represents nitrogen or carbon, or a salt thereof, solvates thereof or solvates of the salts thereof for use in the treatment and/or prophylaxis of heart failure (HFrEF, HFmrEF and HFpEF), hypertension (HTN), chronic and diabetic kidney disease (CKD, DKD), pulmonary hypertension (PH), systemic sclerosis (SSc), sickle cell disease (SCD), neurodegenerative diseases and dementias, or diabetic foot ulcer (DFU).

4. A composition for use as a medication for the treatment and/or prophylaxis of disease comprising a compound according to formula (I)

(I)

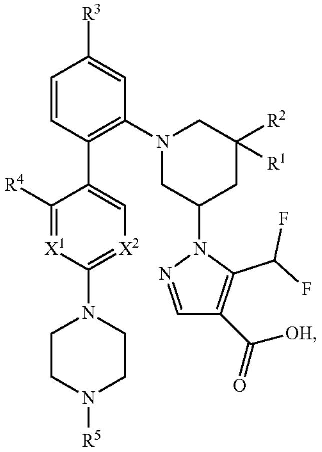

in which $R^1$ represents hydrogen or halogen, $R^2$ represents hydrogen or halogen, $R^3$ represents chloro or trifluoromethyl, $R^4$ represents hydrogen or $C_1$-$C_4$-alkyl, $R^5$ represents $C_1$-$C_6$-alkyl, $X_1$ represents nitrogen or carbon, and $X_2$ represents nitrogen or carbon, or a salt thereof, solvates thereof or solvates of the salts thereof.

5. A composition for use as a medication for the treatment and/or prophylaxis of disease comprising a compound according to formula (I)

(I)

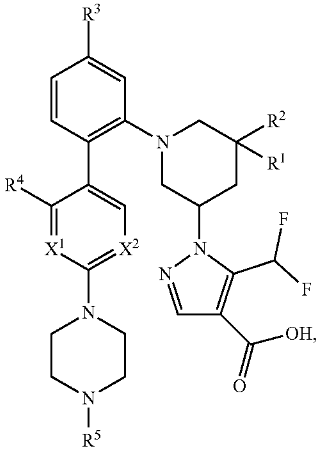

in which $R^1$ represents hydrogen or halogen, $R^2$ represents hydrogen or halogen, $R^3$ represents chloro or trifluoromethyl, $R^4$ represents hydrogen or $C_1$-$C_4$-alkyl, $R^5$ represents $C_1$-$C_6$-alkyl, $X_1$ represents nitrogen or carbon, and $X_2$ represents nitrogen or carbon, or a salt thereof, solvates thereof or solvates of the salts thereof, wherein the disease is selected from the group consisting of heart failure (HFrEF, HFmrEF and HFpEF), hypertension (HTN), chronic and diabetic kidney disease (CKD, DKD), pulmonary hypertension (PH), systemic sclerosis (SSc), sickle cell disease (SCD), neurodegenerative diseases and dementias, and diabetic foot ulcer (DFU).

6. A medicament containing a compound of formula (I) as in claim 3 for use in the treatment and/or prophylaxis of heart failure (HFrEF, HFmrEF and HFpEF), hypertension (HTN), chronic and diabetic kidney disease (CKD, DKD), pulmonary hypertension (PH), systemic sclerosis (SSc), sickle cell disease (SCD), neurodegenerative diseases and dementias, or diabetic foot ulcer (DFU).

* * * * *